United States Patent
Seymour et al.

(10) Patent No.: US 10,034,905 B2
(45) Date of Patent: *Jul. 31, 2018

(54) GROUP B ADENOVIRUS MODIFIED IN THE E4ORF4 REGION

(71) Applicant: PSIOXUS THERAPEUTICS LIMITED, Oxfordshire (GB)

(72) Inventors: Leonard Charles William Seymour, Oxford (GB); Alice Claire Noel Brown, Oxfordshire (GB); Brian Robert Champion, Oxfordshire (GB)

(73) Assignee: PSIOXUS THERAPEUTICS LIMITED, Oxfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/303,505

(22) PCT Filed: Apr. 13, 2015

(86) PCT No.: PCT/EP2015/057994
§ 371 (c)(1),
(2) Date: Oct. 11, 2016

(87) PCT Pub. No.: WO2015/155370
PCT Pub. Date: Oct. 15, 2015

(65) Prior Publication Data
US 2017/0035818 A1    Feb. 9, 2017

(30) Foreign Application Priority Data
Apr. 12, 2014 (GB) .................................. 1406608.8

(51) Int. Cl.
A61K 48/00 (2006.01)
A61K 35/761 (2015.01)
C12N 7/00 (2006.01)
A61K 39/00 (2006.01)

(52) U.S. Cl.
CPC .............. *A61K 35/761* (2013.01); *C12N 7/00* (2013.01); *A61K 2039/5256* (2013.01); *C12N 2710/10321* (2013.01); *C12N 2710/10332* (2013.01); *C12N 2710/10343* (2013.01)

(58) Field of Classification Search
None
See application file for complete search history.

(56) References Cited

U.S. PATENT DOCUMENTS

| | | | | |
|---|---|---|---|---|
| 7,510,868 | B2* | 3/2009 | Harden ................... | C12N 7/00 435/320.1 |
| 2004/0213764 | A1* | 10/2004 | Wold ..................... | A61K 35/76 424/93.2 |
| 2006/0292682 | A1* | 12/2006 | Hawkins ................ | C12N 15/86 435/235.1 |
| 2013/0243731 | A1* | 9/2013 | Dias ..................... | A61K 35/761 424/93.2 |

FOREIGN PATENT DOCUMENTS

| | | |
|---|---|---|
| CN | 102586327 A | 7/2012 |
| WO | WO 2005/118825 A2 | 12/2005 |
| WO | WO 2006/060314 A2 | 6/2006 |
| WO | WO 2015/059303 A1 | 4/2015 |
| WO | 2015077624 A1 | 5/2015 |
| WO | 2016174200 A1 | 11/2016 |

OTHER PUBLICATIONS

Ibrahimi, A. et al., "Highly Efficient Multicistronic Lentiviral Vectors with Peptide 2A sequences", Hum. Gene THer.,2009, vol. 20: pp. 845-860.*
The International Search Report and Written Opinion dated Jul. 31, 2015 in PCT/EP2015/057994.
Kuhn Irene et al., "Directed evolution generates a novel oncolytic virus for the treatment of colon cancer", PLOS ONE, 3(6), Jun. 18, 2008, pp. e2409/1-e2409/11.
Hermiston, T., "Gene Delivery from Replication-Selective Viruses: Arming Guided Missiles in the War Against Cancer", *Journal of Clinical Investigation*, 105(9), May 1, 2000, pp. 1169-1172.
Paul et al., "The combination of a chemokine, cytokine and TCR-based T cell stimulus for effective gene therapy of cancer", Cancer Immunol Immunother. Dec. 2002;51(11-12):645-54. Epub Oct. 9, 2002.
Choi, et al., "Concurrent delivery of GM-CSF and B7-1 using an oncolytic adenovirus elicits potent antitumor effect", Gene Ther. 13(13), 2006, 1010-1020.
Jin, et al., "Identification of novel insertion sites in the Ad5 genome that utilize the Ad splicing machinery for therapeutic gene expression", Mol Ther. 12(6), 2005, 1052-1063.
Lee, et al., "Enhanced antitumor effect of oncolytic adenovirus expressing interleukin-12 and B7-1 in an immunocompetent murine model", Clin Cancer Res. 12(19), 2006, 5859-5868.
Holterman, et al., "Novel replication-incompetent vector derived from adenovirus type 11 (Ad11) for vaccination and gene therapy: low seroprevalence and non-cross-reactivity with Ad5", J Virol. 78(23), 2004, 13207-13215.
Non-Final Office Action for U.S. Appl. No. 15/031,716, dated Dec. 13, 2017.
Stone, et al., "The complete nucleotide sequence, genome organization, and origin of human adenovirus type 11", Virology. 309(1), 2003, 152-165.

* cited by examiner

Primary Examiner — Michael D Burkhart
(74) Attorney, Agent, or Firm — Saul Ewing Arnstein & Lehr LLP; Debora Plehn-Dujowich

(57) ABSTRACT

The present disclosure relates to a type B adenovirus wherein E4orf4 is deleted or non-functional and generally having a DNA sequence in the E3 region, in particular viruses of formula (I), compositions containing the virus, for example pharmaceutical formulations of the virus, processes for making the viruses and the compositions and use of any one of the same in treatment, particularly in the treatment of cancer, such as colorectal cancer and ovarian cancer.

$$5'ITR-B_1-B_A-B_2-B_X-B_B-B_Y-B_3-3'ITR \qquad (I).$$

26 Claims, 4 Drawing Sheets

Figure 3    Shows the cytopathic effects of EnAd or NG-184
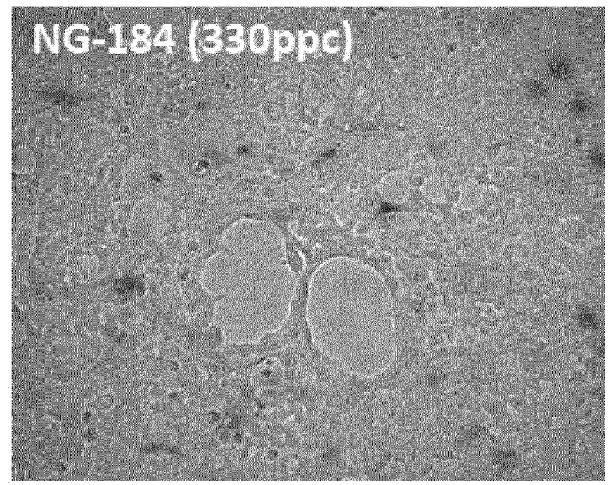
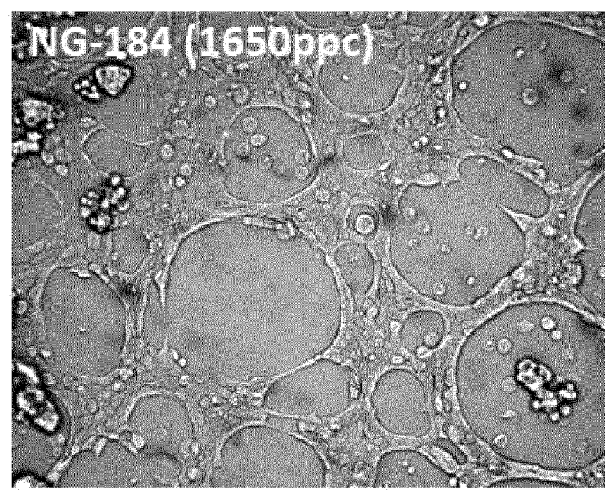
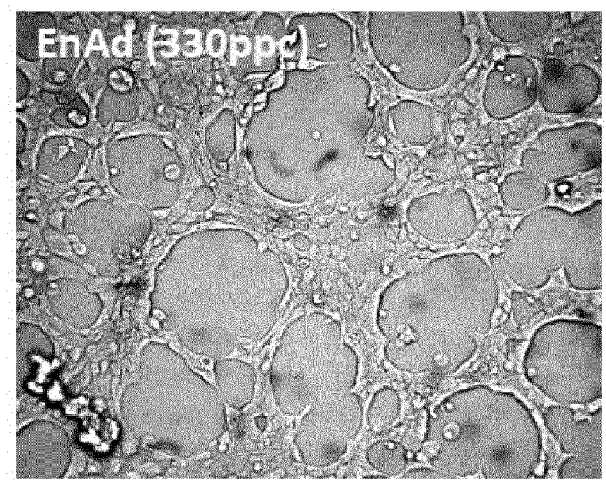

Figure 4 Various Cassette Designs
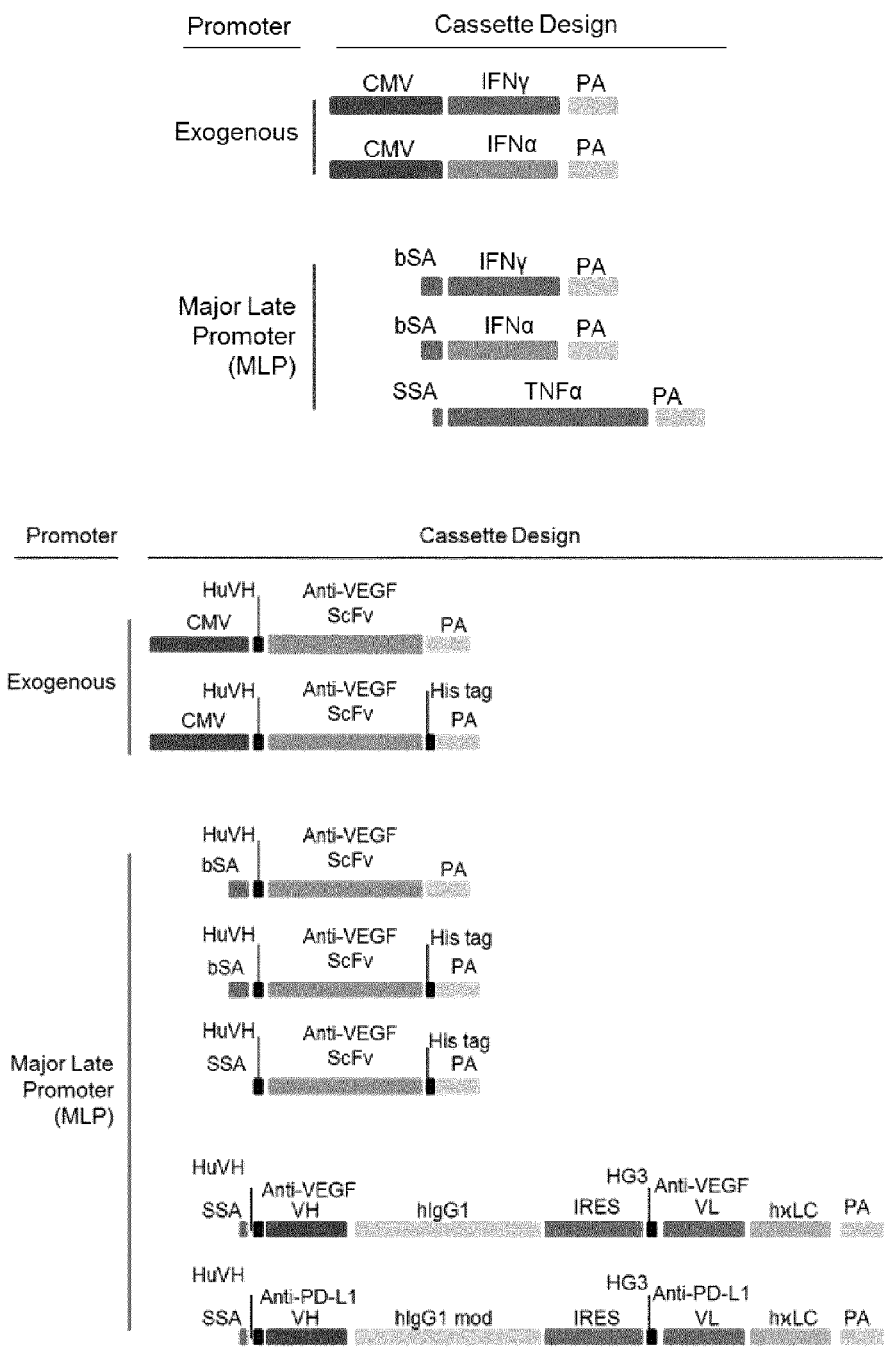

SEQUENCE LISTING

```
<160> NUMBER OF SEQ ID NOS: 31

<210> SEQ ID NO 1
<211> LENGTH: 32326
<212> TYPE: DNA
<213> ORGANISM: Artificial Sequence
<220> FEATURE:
<223> OTHER INFORMATION: EAd1

<400> SEQUENCE: 1
tctatctata taatatacct tatagatgga atggtgccaa tatgtaaatg aggtgatttt      60
aaaaagtgtg gatcgtgtgg tgattggctg tggggttaac ggctaaaagg ggcggtgcga     120
ccgtgggaaa atgacgtttt gtggggtgg agttttttg caagttgtcg cgggaaatgt      180
gacgcataaa aaggcttttt tctcacggaa ctacttagtt ttcccacggt atttaacagg     240
aaatgaggta gttttgaccg gatgcaagtg aaaattgttg attttcgcgc gaaaactgaa     300
tgaggaagtg ttttctgaa taatgtggta tttatggcag ggtggagtat ttgttcaggg     360
ccaggtagac tttgacccat tacgtggagg tttcgattac cgtgtttttt acctgaattt     420
ccgcgtaccg tgtcaaagtc ttctgttttt acgtaggtgt cagctgatcg ctagggtatt     480
tatacctcag ggtttgtgtc aagaggccac tcttgagtgc cagcgagaag agttttctcc     540
tctgcgccgg cagtttaata ataaaaaaat gagagatttg cgatttctgc ctcaggaaat     600
aatctctgct gagactggaa atgaaatatt ggagcttgtg gtgcacgccc tgatgggaga     660
cgatccggag ccacctgtgc agcttttga gcctcctacg cttcaggaac tgtatgattt     720
agaggtagag ggatcggagg attctaatga ggaagctgta aatggctttt ttaccgattc     780
```

```
tatgctttta gctgctaatg aagggttaga attagatccg cctttggaca cttttgatac      840 tccagggta attgtggaaa gcggtacagg tgtaagaaaa ttacctgatt tgagttccgt       900
ggactgtgat ttgcactgct atgaagacgg gtttcctccg agtgatgagg aggaccatga     960
aaaggagcag tccatgcaga ctgcagcggg tgagggagtg aaggctgcca atgttggttt    1020
tcagttggat tgcccggagc ttcctggaca tggctgtaag tcttgtgaat tcacaggaa     1080 aaatactgga gtaaaggaac tgttatgttc gctttgttat atgagaacgc actgccactt    1140
tatttacagt aagtgtgttt aagttaaaat ttaaaggaat atgctgtttt tcacatgtat    1200
attgagtgtg agttttgtgc ttcttattat aggtcctgtg tctgatgctg atgaatcacc    1260
atctcctgat tctactacct cacctcctga gattcaagca cctgttcctg tggacgtgcg    1320
caagcccatt cctgtgaagc ttaagcctgg gaaacgtcca gcagtggaaa aacttgagga    1380
cttgttacag ggtggggacg gacctttgga cttgagtaca cggaaacgtc caagacaata    1440
agtgttccat atccgtgttt acttaaggtg acgtcaatat ttgtgtgaca gtgcaatgta    1500
ataaaaatat gttaactgtt cactggtttt tattgctttt tgggcgggga ctcaggtata   1560
taagtagaag cagacctgtg tggttagctc ataggagctg gctttcatcc atggaggttt    1620
gggccatttt ggaagacctt aggaagacta ggcaactgtt agagaacgct tcggacggag    1680
tctccggttt ttggagattc tggttcgcta gtgaattagc tagggtagtt tttaggataa    1740
aacaggacta taaacaagaa tttgaaaagt tgttggtaga tgcccagga cttttgaag     1800 ctcttaattt gggccatcag gttcacttta agaaaaagt tttatcagtt ttagactttt     1860 caacccccagg tagaactgct gctgctgtgg ctttttcttac tttttatatta gataaatgga  1920 tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcta gtggtactga tgctagatct gagttggctt taagtttaat   2280
gagtcgcaga cgtcctgaaa ccatttggtg gcatgaggtt cagaaagagg aagggatga   2340 agtttctgta ttgcaggaga aatattcact ggaacaggtg aaaacatgtt ggttggagcc  2400
tgaggatgat tgggaggtgg ccattaaaaa ttatgccaag atagctttga ggcctgataa   2460
acagtataag attactagac ggattaatat ccggaatgct tgttacatat ctggaaatgg   2520
ggctgaggtg gtaatagata ctcaagacaa ggcagttatt agatgctgca tgatggatat   2580
gtggcctggg gtagtcggta tggaagcagt aacttttgta aatgttaagt ttagggggaga  2640 tggttataat ggaatagtgt ttatggccaa taccaaactt atattgcatg gttgtagctt   2700
ttttggtttc aacaatacct gtgtagatgc ctggggacag gttagtgtac ggggatgtag   2760
tttctatgcg tgttggattg ccacagctgg cagaaccaag agtcaattgt ctctgaagaa   2820
atgcatattt caaagatgta acctgggcat tctgaatgaa ggcgaagcaa gggtccgcca  2880
ctgcgcttct acagatactg gatgttttat tttgattaag ggaaatgcca gcgtaaagca   2940
taacatgatt tgcggtgctt ccgatgagag gccttatcaa atgctcactt tgtgctggtgg 3000 gcattgtaat atgctggcta ctgtgcatat tgtttcccat caacgcaaaa aatggcctgt  3060
ttttgatcac aatgtgatga cgaagtgtac catgcatgca ggtgggcgta gaggaatgtt   3120
tatgccttac cagtgtaaca tgaatcatgt gaaagtgttg ttggaaccag atgcctttc    3180
```

```
cagaatgagc ctaacaggaa tttttgacat gaacatgcaa atctggaaga tcctgaggta   3240
tgatgatacg agatcgaggg tacgcgcatg cgaatgcgga ggcaagcatg ccaggttcca   3300
gccggtgtgt gtagatgtga ctgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gttttttctg tcttgcagct   3480
gtcatgagtg gaaacgcttc ttttaagggg ggagtcttca gcccttatct gacagggcgt   3540
ctcccatcct gggcaggagt tcgtcagaat gttatgggat ctactgtgga tggaagaccc   3600
gtccaacccg ccaattcttc aacgctgacc tatgctactt taagttcttc acctttggac   3660
gcagctgcag ctgccgccgc cgcttctgtt gccgctaaca ctgtgcttgg aatgggttac   3720 tatgaagca tcatggctaa ttccacttcc tctaataacc cttctaccct gactcaggac   3780
aagttacttg tccttttggc ccagctggag gctttgaccc aacgtctggg tgaactttct   3840
cagcaggtgg tcgagttgcg agtacaaact gagtctgctg tcggcacggc aaagtctaaa   3900
taaaaaaatc ccagaatcaa tgaataaata acaagcttg ttgttgattt aaaatcaagt    3960
gtttttattt catttttcgc gcacggtatg ccctagacca ccgatctcta tcattgagaa   4020
ctcggtggat tttttccagg atcctataga ggtgggattg aatgtttaga tacatgggca   4080
ttaggccgtc tttggggtgg agatagctcc attgaaggga ttcatgctcc ggggtagtgt   4140
tgtaaatcac ccagtcataa caaggtcgca gtgcatggtg ttgcacaata tcttttagaa   4200
gtaggctgat tgccacagat aagcccttgg tgtaggtgtt tacaaaccgg ttgagctggg   4260
atgggtgcat tcggggtgaa attatgtgca ttttggattg gattttttaag ttggcaatat   4320 tgccgccaag atcccgtctt gggttcatgt tatgaaggac caccaagacg gtgtatccgg   4380
tacatttagg aaatttatcg tgcagcttgg atggaaaagc gtggaaaaat ttggagacac   4440
ccttgtgtcc tccaagattt tccatgcact catccatgat aatagcaatg gggccgtggg   4500
cagcggcgcg ggcaaacacg ttccgtgggt ctgacacatc atagttatgt tcctgagtta   4560
aatcatcata agccatttta atgaatttgg ggcggagagt accagattgg ggtatgaatg   4620
ttccttcggg ccccggagca tagttcccct cacagatttg catttcccaa gctttcagtt   4680
ccgagggtgg aatcatgtcc acctgggggg ctatgaaaaa caccgttcct ggggcggggg   4740
tgattaattg tgatgatagc aaatttctga gcaattgaga tttgccacat ccggtggggc   4800
cataaatgat tccgattacg ggttgcaggt ggtagtttag ggaacggcaa ctgccgtctt   4860
ctcgaagcaa gggggccacc tcgttcatca tttcccttac atgcatattt tcccgcacca   4920
aatccattag gaggcgctct cctcctagtg atagaagttc ttgtagtgag gaaaagtttt   4980
tcagcggttt cagaccgtca gccatgggca ttttggagag agtttgctgc aaaagttcta   5040
gtctgttcca cagttcagtg atgtgttcta tggcatctcg atccagcaga cctcctcgtt   5100
tcgcgggttt ggacggctcc tggaatanggg tatgagacga tgggcgtcca gcgctgccag   5160
ggttcggtcc ttccagggtc tcagtgttcg agtcagggtt gtttccgtca cagtgaaggg   5220
gtgtgcgcct gcttgggcgc ttgccagggt gcgcttcaga ctcatcctgc tggtcgaaaa   5280
cttctgtcgc ttggcgccct gtatgtcggc caagtagcag tttaccatga gttcgtagtt   5340
gagcgcctcg gctgcgtggc ctttggcgcg gagcttacct ttggaagttt tcttgcatac   5400
cgggcagtat aggcatttca gcgcatacaa cttgggcgca aggaaaacgg attctgggga   5460
gtatgcatct gcgccgcagg aggcgcaaac agtttcacat tccaccagcc aggttaaatc   5520
```

```
cggttcattg gggtcaaaaa caagttttcc gccatatttt ttgatgcgtt tcttaccttt   5580
ggtctccatg agttcgtgtc ctcgttgagt gacaaacagg ctgtccgtgt ccccgtagac   5640
tgattttaca ggcctcttct ccagtggagt gcctcggtct tcttcgtaca ggaactctga   5700
ccactctgat acaaaggcgc gcgtccaggc cagcacaaag gaggctatgt gggaggggta   5760
gcgatcgttg tcaaccaggg ggtccacctt ttccaaagta tgcaaacaca tgtcaccctc   5820
ttcaacatcc aggaatgtga ttggcttgta ggtgtatttc acgtgacctg ggtccccgc    5880 tgggggggta taaaaggggg cggttctttg ctcttcctca ctgtcttccg gatcgctgtc   5940
caggaacgtc agctgttggg gtaggtattc cctctcgaag gcgggcatga cctctgcact   6000
caggttgtca gtttctaaga acgaggagga tttgatattg acagtgccgg ttgagatgcc   6060
tttcatgagg ttttcgtcca tctggtcaga aaacacaatt ttttttattgt caagtttggt   6120 ggcaaatgat ccatacaggg cgttggataa agtttggca atggatcgca tggtttggtt    6180
cttttccttg tccgcgcgct ctttggcggc gatgttgagt tggacatact cgcgtgccag   6240
gcacttccat tcggggaaga tagttgttaa ttcatctggc acgattctca cttgccaccc   6300
tcgattatgc aaggtaatta aatccacact ggtggccacc tcgcctcgaa ggggttcatt   6360
ggtccaacag agcctacctc ctttcctaga acagaaaggg ggaagtgggt ctagcataag   6420
ttcatcggga gggtctgcat ccatggtaaa gattcccgga agtaaatcct tatcaaaata   6480
gctgatggga gtggggtcat ctaaggccat ttgccattct cgagctgcca gtgcgcgctc   6540
atatgggtta aggggactgc cccatggcat gggatgggtg agtgcagagg catacatgcc   6600
acagatgtca tagacgtaga tgggatcctc aaagatgcct atgtaggttg atagcatcg    6660 ccccccctctg atacttgctc gcacatagtc atatagttca tgtgatggcg ctagcagccc   6720
cggacccaag ttggtgcgat tgggttttt tgttctgtag acgatctggc gaaagatggc    6780
gtgagaattg gaagagatgg tgggtctttg aaaaatgttg aaatgggcat gaggtagacc   6840
tacagagtct ctgacaaagt gggcataaga ttcttgaagc ttggttacca gttcggcggt   6900
gacaagtacg tctagggcgc agtagtcaag tgtttcttga atgatgtcat aacctggttg   6960
gttttctctt tcccacagtt cgcggttgag aaggtattct tcgcgatcct tccagtactc   7020
ttctagcgga aacccgtctt tgtctgcacg gtaagatcct agcatgtaga actgattaac   7080
tgccttgtaa gggcagcagc ccttctctac gggtagagag tatgcttgag cagcttttcg   7140
tagcgaagcg tgagtaaggg caaaggtgtc tctgaccatg actttgagga attggtatttt  7200 gaagtcgatg tcgtcacagg ctccctgttc ccagagttgg aagtctaccc gtttcttgta   7260
ggcggggttg ggcaaagcga agtaacatc attgaagaga atcttgccgg ccctgggcat    7320
gaaattgcga gtgatgcgaa aaggctgtgg tacttccgct cggttattga taacctgggc   7380
agctaggacg atctcgtcga aaccgttgat gttgtgtcct acgatgtata attctatgaa   7440
acgcggcgtg cctctgacgt gaggtagctt actgagctca tcaaaggtta ggtctgtggg   7500
gtcagataag gcgtagtgtt cgagagccca ttcgtgcagg tgaggattcg ctttaaggaa   7560
ggaggaccag aggtccactg ccagtgctgt ttgtaactgg tcccggtact gacgaaaatg   7620
ccgtccgact gccatttttt ctggggtgac gcaatagaag gtttgggggt cctgccgcca   7680
gcgatcccac ttgagtttta tggcgaggtc ataggcgatg ttgacgagcc gctggtctcc   7740
agagagtttc atgaccagca tgaagggat tagctgcttg ccaaaggacc ccatccaggt    7800 gtaggttttcc acatcgtagg tgagaaagag ccttctctgtg cgaggatgag agccaatcgg  7860
gaagaactgg atctcctgcc accagttgga ggaatggctg ttgatgtgat ggaagtagaa   7920
```

```
ctccctgcga cgcgccgagc attcatgctt gtgcttgtac agacggccgc agtagtcgca    7980
gcgttgcacg ggttgtatct cgtgaatgag ttgtacctgg cttcccttga cgagaaattt    8040
cagtgggaag ccgaggcctg gcgattgtat ctcgtgcttt actatgttgt ctgcatcggc    8100
ctgttcatct tctgtctcga tggtggtcat gctgacgagc cctcgcggga ggcaagtcca    8160
gacctcggcg cggcaggggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
cattttggac ggcggtggct ctgttgcttc ttgcatgttt agaagcggtg tcgagggcgc    8460
gcaccgggcg gcaggggcgg ctcgggaccc ggcggcatgg ctggcagtgg tacgtcggcg    8520
ccgcgcgcgg gtaggttctg gtactgcgcc ctgagaagac tcgcatgcgc gacgacgcgg    8580
cggttgacat cctggatctg acgcctctgg gtgaaagcta ccggcccgt gagcttgaac     8640
ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacgtgg ccgcgaggtc gttggagatg     8820
cgcccaatga gttgagagaa tgcattcatg cccgcctcgt tccagacgcg gctgtagacc    8880
acggccccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgg caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tctcttcttc ttccactaac    9240
atctcttcct cttcaggtgg ggctgcagga ggaggggaa cgcggcgacg ccggcggcgc     9300
acgggcagac ggtcgatgaa tctttcaatg acctctccgc ggcggcggcg catggtttca    9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcggaa     9660
ggtgagacga tgctgctggt gatgaaatta agtaggcag ttctaagacg gcggatggtg     9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt tcggcgagga tggcttgctg tacttgggta    9960
agggtggctt gaaagtcatc aaaatccaca aagcggtggt aagctcctgt attaatggtg    10020
taagcacagt tggccatgac tgaccagtta actgtctggt gaccagggcg cacgagctcg    10080
gtgtatttaa ggcgcgaata ggcgcgggtg tcaaagatgt aatcgttgca ggtgcgcacc    10140
agatactggt accctataag aaaatgcggc ggtggttggc ggtagagagg ccatcgttct    10200
gtagctggag cgccaggggc gaggtcttcc aacataaggc ggtgatagcc gtagatgtac    10260
```

```
ctggacatcc aggtgattcc tgcggcggta gtagaagccc aggaaactc gcgtacgcgg    10320 ttccaaatgt tgcgtagcgg catgaagtag ttcattgtag gcacggtttg accagtgagg    10380
cgcgcgcagt cattgatgct ctatagacac ggagaaaatg aaagcgttca gcgactcgac    10440
tccgtagcct ggaggaacgt gaacgggttg ggtcgcggtg tacccggtt cgagacttgt    10500 actcgagccg gccggagccg cggctaacgt ggtattggca ctcccgtctc gacccagcct    10560
acaaaaatcc aggatacgga atcgagtcgt tttgctggtt tccgaatggc agggaagtga    10620
gtcctatttt ttttttttgc cgctcagatg catcccgtgc tgcgacagat gcgccccaa    10680 caacagcccc cctcgcagca gcagcagcag caatcacaaa aggctgtccc tgcaactact    10740
gcaactgccg ccgtgagcgg tgcgggacag cccgcctatg atctggactt ggaagagggc    10800
gaaggactgg cacgtctagg tgcgccttca cccgagcggc atccgcgagt tcaactgaaa    10860
aaagattctc gcgaggcgta tgtgccccaa cagaacctat ttagagacag aagcggcgag    10920
gagccggagg agatgcgagc ttcccgcttt aacgcgggtc gtgagctgcg tcacggtttg    10980
gaccgaagac gagtgttgcg ggacgaggat ttcgaagttg atgaaatgac agggatcagt    11040
cctgccaggg cacacgtggc tgcagccaac cttgtatcgg cttacgagca gacagtaaag    11100
gaagagcgta acttccaaaa gtcttttaat aatcatgtgc gaaccctgat tgcccgcgaa    11160
gaagttaccc ttggtttgat gcatttgtgg gatttgatgg aagctatcat tcagaaccct    11220
actagcaaac ctctgaccgc ccagctgttt ctggtggtgc aacacagcag agacaatgag    11280
gctttcagag aggcgctgct gaacatcacc gaacccgagg ggagatggtt gtatgatctt    11340
atcaacattc tacagagtat catagtgcag gagcggagcc tgggcctggc cgagaaggtg    11400
gctgccatca attactcggt tttgagcttg ggaaaatatt acgctcgcaa aatctacaag    11460
actccatacg ttcccataga caaggagtg aagatagatg ggttctacat gcgcatgacg    11520
ctcaaggtct tgaccctgag cgatgatctt ggggtgtatc gcaatgacag aatgcatcgc    11580
gcggttagcg ccagcaggag gcgcgagtta agcgacaggg aactgatgca cagtttgcaa    11640
agagctctga ctggagctgg aaccgagggt gagaattact tcgacatggg agctgacttg    11700
cagtggcagc ctagtcgcag ggctctgagc gccgcgacgg caggatgtga gcttccttac    11760
atagaagagg cggatgaagg cgaggaggaa gagggcgagt acttggaaga ctgatggcac    11820
aacccgtgtt ttttgctaga tggaacagca agcaccggat cccgcaatgc gggcggcgct    11880
gcagagccag ccgtccggca ttaactcctc ggacgattgg acccaggcca tgcaacgtat    11940
catggcgttg acgactcgca accccgaagc ctttagacag caaccccagg ccaaccgtct    12000
atcggccatc atggaagctg tagtgccttc ccgctctaat cccactcatg agaaggtcct    12060
ggccatcgtg aacgcgttgg tggagaacaa agctattcgt ccagatgagg ccggactggt    12120
atacaacgct ctcttagaac gcgtggctcg ctacaacagt agcaatgtgc aaaccaattt    12180
ggaccgtatg ataacagatg tacgcgaagc cgtgtctcag cgcgaaaggt tccagcgtga    12240
tgccaacctg ggttcgctgg tggcgttaaa tgctttcttg agtactcagc ctgctaatgt    12300
gccgcgtggt caacaggatt atactaactt tttaagtgct ttgagactga tggtatcaga    12360
agtacctcag agcgaagtgt atcagtccgg tcctgattac ttctttcaga ctagcagaca    12420
gggcttgcag acggtaaatc tgagccaagc ttttaaaaac cttaaaggtt tgtggggagt    12480
gcatgccccg gtaggagaaa gagcaaccgt gtctagcttg ttaactccga actcccgcct    12540
attattactg ttggtagctc cttttcaccga cagcggtagc atcgaccgta attcctattt    12600
gggttaccta ctaaacctgt atcgcgaagc catagggcaa agtcaggtgg acgagcagac    12660
```

```
ctatcaagaa attacccaag tcagtcgcgc tttgggacag gaagacactg gcagtttgga    12720
agccactctg aacttcttgc ttaccaatcg gtctcaaaag atccctcctc aatatgctct    12780
tactgcggag gaggagagga tccttagata tgtgcagcag agcgtgggat tgtttctgat    12840
gcaagagggg gcaactccga ctgcagcact ggacatgaca gcgcgaaata tggagcccag    12900
catgtatgcc agtaaccgac cttt cattaa caaactgctg gactacttgc acagagctgc    12960
cgctatgaac tctgattatt tcaccaatgc catcttaaac ccgcactggc tgcccccacc    13020
tggtttctac acgggcgaat atgacatgcc cgaccctaat gacggatttc tgtgggacga    13080
cgtggacagc gatgtttttt cacctctttc tgatcatcgc acgtggaaaa aggaaggcgg    13140
cgatagaatg cattcttctg catcgctgtc cggggtcatg ggtgctaccg cggctgagcc    13200
cgagtctgca agtccttttc ctagtctacc cttttctcta cacagtgtac gtagcagcga    13260
agtgggtaga ataagtcgcc cgagtttaat gggcgaagag gagtatctaa acgattcctt    13320
gctcagaccg gcaagagaaa aaaatttccc aaacaatgga atagaaagtt tggtggataa    13380
aatgagtaga tggaagactt atgctcagga tcacagagac gagcctggga tcatggggat    13440
tacaagtaga gcgagccgta gacgccagcg ccatgacaga cagaggggtc ttgtgtggga    13500
cgatgaggat tcggccgatg atagcagcgt gctggacttg ggtgggagag aaggggcaa    13560 cccgtttgct catttgcgcc ctcgcttggg tggtatgttg taaaaaaaaa taaaaaaaaa    13620
actcaccaag gccatggcga cgagcgtacg ttcgttcttc tttattatct gtgtctagta    13680
taatgaggcg agtcgtgcta ggcggagcgg tggtgtatcc ggagggtcct cctccttcgt    13740
acgagagcgt gatgcagcag cagcaggcga cggcggtgat gcaatcccca ctggaggctc    13800
cctttgtgcc tccgcgatac ctggcaccta cggagggcag aaacagcatt cgttattcgg    13860
aactggcacc tcagtacgat accaccaggt tgtatctggt ggacaacaag tcggcggaca    13920
ttgcttctct gaactatcag aatgaccaca gcaacttctt gaccacggtg gtgcaaaaca    13980
atgactttac ccctacggaa gccagcaccc agaccattaa ctttgatgaa cgatcgcggt    14040
ggggcggtca gctaaagacc atcatgcata ctaacatgcc aaacgtgaac gagtatatgt    14100
ttagtaacaa gttcaaagcg cgtgtgatgg tgtccagaaa acctcccgac ggtgctgcag    14160
ttggggatac ttatgatcac aagcaggata ttttgaaata tgagtggttc gagtttactt    14220
tgccagaagg caacttttca gttactatga ctattgattt tgatgaacaat gccatcatag    14280 ataattactt gaaagtgggt agacagaatg gagtgcttga agtgacattg ggtgttaagt    14340
tcgacaccag gaacttcaag ctgggatggg atcccgaaac caagttgatc atgcctggag    14400
tgtatacgta tgaagccttc catcctgaca ttgtcttact gcctggctgc ggagtggatt    14460
ttaccgagag tcgtttgagc aaccttcttg gtatcagaaa aaaacagcca tttcaagagg    14520
gttttaagat tttgtatgaa gatttagaag gtggtaatat tccggccctc ttggatgtag    14580
atgcctatga gaacagtaag aaagaacaaa aagccaaaat agaagctgct acagctgctg    14640
cagaagctaa ggcaaacata gttgccagcg actctacaag ggttgctaac gctggagagg    14700
tcagaggaga caattttgcg ccaacacctg ttccgactgc agaatcatta ttggccgatg    14760
tgtctgaagg aacggacgtg aaactcacta ttcaacctgt agaaaagat agtaagaata    14820 gaagctataa tgtgttggaa gacaaaatca acacagccta tcgcagttgg tatctttcgt    14880
acaattatgg cgatcccgaa aaaggagtgc gttcctggac attgctcacc acctcagatg    14940
tcacctgcgg agcagagcag gtctactggt cgcttccaga catgatgaag gatcctgtca    15000
```

```
ctttccgctc cactagacaa gtcagtaact accctgtggt gggtgcagag cttatgcccg    15060
tcttctcaaa gagcttctac aacgaacaag ctgtgtactc ccagcagctc cgccagtcca    15120
cctcgcttac gcacgtcttc aaccgctttc ctgagaacca gattttaatc cgtccgccgg    15180
cgcccaccat taccaccgtc agtgaaaacg ttcctgctct cacagatcac gggaccctgc    15240
cgttgcgcag cagtatccgg ggagtccaac gtgtgaccgt tactgacgcc agacgccgca    15300
cctgtcccta cgtgtacaag gcactgggca tagtcgcacc gcgcgtcctt tcaagccgca    15360
ctttctaaaa aaaaaaaaaa tgtccattct tatctcgccc agtaataaca ccggttgggg    15420
tctgcgcgct ccaagcaaga tgtacggagg cgcacgcaaa cgttctaccc aacatcctgt    15480
ccgtgttcgc ggacattttc gcgctccatg gggcgccctc aagggccgca ctcgcgttcg    15540
aaccaccgtc gatgatgtaa tcgatcaggt ggttgccgac gcccgtaatt atactcctac    15600
tgcgcctaca tctactgtgg atgcagttat tgacagtgta gtggctgacg ctcgcaacta    15660
tgctcgacgt aagagccggc gaaggcgcat tgccagacgc caccgagcta ccactgccat    15720
gcgagccgca agagctctgc tacgaagagc tagacgcgtg gggcgaagag ccatgcttag    15780
ggcggccaga cgtgcagctt cgggcgccag cgccggcagg tcccgcaggc aagcagccgc    15840
tgtcgcagcg gcgactattg ccgacatggc ccaatcgcga agaggcaatg tatactgggt    15900
gcgtgacgct gccaccggtc aacgtgtacc cgtgcgcacc cgtcccccctc gcacttagaa    15960 gatactgagc agtctccgat gttgtgtccc agcggcgagg atgtccaagc gcaaatacaa    16020
ggaagaaatg ctgcaggtta tcgcacctga agtctacggc caaccgttga aggatgaaaa    16080 aaaacccgc aaaatcaagc gggttaaaaa ggacaaaaaa gaagaggaag atggcgatga    16140
tgggctggcg gagtttgtgc gcgagtttgc cccacggcga cgcgtgcaat ggcgtgggcg    16200
caaagttcga catgtgttga gacctggaac ttcggtggtc tttacacccg gcgagcgttc    16260
aagcgctact tttaagcgtt cctatgatga ggtgtacggg gatgatgata ttcttgagca    16320
ggcggctgac cgattaggcg agtttgctta tggcaagcgt agtagaataa cttccaagga    16380
tgagacagtg tcgataccct tggatcatgg aaatcccacc cctagtctta aaccggtcac    16440
tttgcagcaa gtgttacccg taactccgcg aacaggtgtt aaacgcgaag gtgaagattt    16500
gtatcccact atgcaactga tggtacccaa acgccagaag ttggaggacg ttttggagaa    16560
agtaaaagtg gatccagata ttcaacctga ggttaaagtg agacccatta agcaggtagc    16620
gcctggtctg ggggtacaaa ctgtagacat taagattccc actgaaagta tggaagtgca    16680
aactgaaccc gcaaagccta ctgccaccctc cactgaagtg caaacggatc catggatgcc    16740
catgcctatt acaactgacg ccgccggtcc cactcgaaga tcccgacgaa agtacggtcc    16800
agcaagtctg ttgatgccca attatgttgt acacccatct attattccta ctcctggtta    16860
ccgaggcact cgctactatc gcagccgaaa cagtacctcc cgccgtcgcc gcaagacacc    16920
tgcaaatcgc agtcgtcgcc gtagacgcac aagcaaaccg actcccggcg ccctggtgcg    16980
gcaagtgtac cgcaatggta gtgcggaacc tttgacactg ccgcgtgcgc gttaccatcc    17040
gagtatcatc acttaatcaa tgttgccgct gcctccttgc agatatggcc ctcacttgtc    17100
gccttcgcgt tccatcact ggttaccgag gaagaaactc gcgccgtaga agagggatgt    17160
tgggacgcgg aatgcgacgc tacaggcgac ggcgtgctat ccgcaagcaa ttgcggggtg    17220
gttttttacc agccttaatt ccaattatcg ctgctgcaat tggcgcgata ccaggcatag    17280
cttccgtggc ggttcaggcc tcgcaacgac attgacattg gaaaaaaacg tataaataaa    17340
aaaaaaaaaa tacaatggac tctgacactc ctggtcctgt gactatgttt tcttagagat    17400
```

```
ggaagacatc aattttcat ccttggctcc gcgacacggc acgaagccgt acatgggcac   17460
ctggagcgac atcggcacga gccaactgaa cgggggcgcc ttcaattgga gcagtatctg   17520
gagcgggctt aaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaacccca ggtgaaatgc aagtggagga   17760
agaaattcct ccgccagaaa acgaggcga caagcgtccg cgtcccgatt tggaagagac   17820
gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttggatttgc cccctccccc tgctgctact gctgtacccg cttctaagcc   18000
tgtcgctgcc ccgaaaccag tcgccgtagc caggtcacgt cccggggggcg ctcctcgtcc   18060
aaatgcgcac tggcaaaata ctctgaacag catcgtgggt ctaggcgtgc aaagtgtaaa   18120
acgccgtcgc tgcttttaat taaatatgga gtagcgctta acttgcctat ctgtgtatat   18180
gtgtcattac acgccgtcac agcagcagag gaaaaaagga agaggtcgtg cgtcgacgct   18240
gagttacttt caagatggcc accccatcga tgctgcccca atgggcatac atgcacatcg   18300
ccggacagga tgcttcggag tacctgagtc cgggtctggt gcagttcgcc cgcgccacag   18360
acacctactt caatctggga aataagttta gaaatccac cgtagcgccg acccacgatg   18420
tgaccaccga ccgtagccag cggctcatgt tgcgcttcgt gcccgttgac cgggaggaca   18480
atacatactc ttacaaagtg cggtacaccc tggccgtggg cgacaacaga gtgctggata   18540
tggccagcac gttctttgac attaggggtg tgttggacag aggtcccagt ttcaaaccct   18600
attctggtac ggcttacaac tccctggctc ctaaaggcgc tccaaataca tctcagtgga   18660
ttgcagaagg tgtaaaaaat acaactggtg aggaacacgt aacagaagag gaaaccaata   18720
ctactactta cacttttggc aatgctcctg taaaagctga agctgaaatt acaaaagaag   18780
gactcccagt aggtttggaa gtttcagatg aagaaagtaa accgattat gctgataaaa   18840
catatcagcc agaacctcag ctgggagatg aaacttggac tgaccttgat ggaaaaaccg   18900
aaaagtatgg aggcagggct ctcaaacccg atactaagat gaaaccatgc tacgggtcct   18960
ttgccaaacc tactaatgtg aaaggcggtc aggcaaaaca aaaaacaacg gagcagccaa   19020
atcagaaagt cgaatatgat atcgacatgg agtttttga tgcggcatcg cagaaaacaa   19080
acttaagtcc taaaattgtc atgtatgcag aaaatgtaaa tttggaaact ccagacactc   19140
atgtagtgta caaacctgga acagaagaca caagttccga agctaatttg ggacaacaat   19200
ctatgcccaa cagacccaac tacattggct tcagagataa cttttattgga cttatgtact   19260
ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atactttagc atgtggaatc aggctgtgga cagttatgat cctgatgtac   19440
gtgttattga aaatcatggt gtggaagatg aacttcccaa ctactgtttt ccactggacg   19500
gcataggtgt tccaacaacc agttacaaat caatagttcc aaatgagac aatgcgccta   19560
attggaagga acctgaagta aatggaacaa gtgagatcgg acagggtaat ttgtttgcca   19620
tggaaattaa ccttcaagcc aatctatggc gaagtttcct ttattccaat gtggctctat   19680
atctcccaga ctcgtacaaa tacaccccgt ccaatgtcac tcttccagaa aacaaaaaca   19740
```

```
cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg aactttagg aaggatgtga acatggttct acagagttcc ctcggtaacg    20040
acctgcgggt agatggcgcc agcatcagtt tcacgagcat caacctctat gctacttttt   20100
tccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccatttcc attccttctc gcaactgggc ggctttcaga ggctggtcat   20280
ttaccagact gaaaaccaaa gaaactccct ctttggggtc tggatttgac ccctactttg   20340
tctattctgg ttctattccc tacctggatg gtaccttcta cctgaaccac acttttaaga   20400
aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc attttttcaga aacttccagc   20640 ccatgagcag gcaggtggtt gatgaggtca attacaaaga cttcaaggcc gtcgccatac   20700
cctaccaaca caacaactct ggcttttgtgg gttacatggc tccgaccatg cgccaaggtc   20760
aaccctatcc cgctaactat ccctatccac tcattggaac aactgccgta aatagtgtta   20820
cgcagaaaaa gttcttgtgt gacagaacca tgtggcgcat accgttctcg agcaacttca   20880
tgtctatggg ggcccttaca gacttgggac agaatatgct ctatgccaac tcagctcatg   20940
ctctggacat gaccttgag gtggatccca tggatgagcc caccctgctt tatcttctct    21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
aaatagcagc tgcaaccatg gcctgcggat cccaaaacgg ctccagcgag caagagctca   21180
gagccattgt ccaagacctg ggttgcggac cctattttt gggaacctac gataagcgct   21240
tcccggggtt catggccccc gataagctcg cctgtgccat tgtaaatacg gccggacgtg   21300 agacggggg agagcactgg ttggctttcg gttggaaccc acgttctaac acctgctacc   21360 ttttttgatcc ttttggattc tcggatgatc gtctcaaaca gatttaccag tttgaatatg   21420
agggtctcct gcgccgcagc gctcttgcta ccaaggaccg ctgtattacg ctggaaaaat   21480
ctacccagac cgtgcagggt cccgttctg ccgcctgcgg acttttctgc tgcatgttcc    21540
ttcacgcctt tgtgcactgg cctgaccgtc ccatggacgg aaaccccacc atgaaattgc   21600
taactggagt gccaaacaac atgcttcatt ctcctaaagt ccagcccacc ctgtgtgaca   21660
atcaaaaagc actctaccat tttcttaata cccattcgcc ttattttcgc tcccatcgta   21720
cacacatcga aagggccact cgttcgacc gtatggatgt caataatga ctcatgtaaa    21780 caacgtgttc aataaacatc actttatttt tttacatgta tcaaggctct gcattactta   21840
tttatttaca agtcgaatgg gttctgacga gaatcagaat gacccgcagg cagtgatacg   21900
ttgcggaact gatacttggg ttgccacttg aattcgggaa tcaccaactt gggaaccggt   21960
atatcgggca ggatgtcact ccacagcttt ctggtcagct gcaaagctcc aagcaggtca   22020
ggagccgaaa tcttgaaatc acaattagga ccagtgcttt gagcgcgaga gttgcggtac   22080
accggattgc agcactgaaa caccatcagc gacggatgtc tcacgcttgc cagcacgtg    22140
```

```
ggatctgcaa tcatgcccac atccagatct tcagcattgg caatgctgaa cggggtcatc   22200
ttgcaggtct gcctacccat ggcgggcacc caattaggct tgtggttgca atcgcagtgc   22260 aggggatca gtatcatctt ggcctgatcc tgtctgattc ctggatacac ggctctcatg    22320
aaagcatcat attgcttgaa agcctgctgg gctttactac cctcggtata aacatcccg    22380 caggacctgc tcgaaaactg gttagctgca cagccggcat cattcacaca gcagcgggcg   22440
tcattgttag ctatttgcac cacacttctg ccccagcggt tttgggtgat tttggttcgc   22500
tcgggattct cctttaaggc tcgttgtccg ttctcgctgg ccacatccat ctcgataatc   22560
tgctccttct gaatcataat attgccatgc aggcacttca gcttgccctc ataatcattg   22620
cagccatgag gccacaacgc acagcctgta cattcccaat tatggtgggc gatctgagaa   22680
aaagaatgta tcattccctg cagaaatctt cccatcatcg tgctcagtgt cttgtgacta   22740
gtgaaagtta actggatgcc tcggtgctcc tcgtttacgt actggtgaca gatgcgcttg   22800
tattgttcgt gttgctcagg cattagttta aagagggttc taagttcgtt atccagcctg   22860
tacttctcca tcagcagaca catcacttcc atgcctttct cccaagcaga caccaggggc   22920
aagctaatcg gattcttaac agtgcaggca gcagctcctt tagccagagg gtcatcttta   22980
gcgatcttct caatgcttct tttgccatcc ttctcaacga tgcgcacggg cgggtagctg   23040
aaacccactg ctacaagttg cgcctcttct ctttcttctt cgctgtcttg actgatgtct   23100
tgcatgggga tatgtttggt cttccttggc ttcttttttgg ggggtatcgg aggaggagga   23160
ctgtcgctcc gttccggaga cagggaggat tgtgacgttt cgctcaccat taccaactga   23220
ctgtcggtag aagaacctga ccccacacgg cgacaggtgt ttctcttcgg gggcagaggt   23280
ggaggcgatt gcgaagggct gcggtccgac ctggaaggcg gatgactggc agaaccccctt  23340 ccgcgttcgg gggtgtgctc cctgtggcgg tcgcttaact gatttccttc gcggctggcc   23400
attgtgttct cctaggcaga gaaacaacag acatggaaac tcagccattg ctgtcaacat   23460
cgccacgagt gccatcacat ctcgtcctca gcgacgagga aaaggagcag agcttaagca   23520
ttccaccgcc cagtcctgcc accacctcta ccctagaaga taaggaggtc gacgcatctc   23580
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct catagggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tccccccaaa cgtcagccaa   23940
acggcacctg cgagccaaat cctcgcttaa acttttatcc agcttttgct gtgccagaag   24000
tactggctac ctatcacatc ttttttaaaa atcaaaaaat tccagtctcc tgccgcgcta   24060
atcgcacccg cgccgatgcc ctactcaatc tgggacctgg ttcacgctta cctgatatag   24120
cttccttgga agaggttcca aagatcttcg agggtctggg caataatgag actcgggccg   24180
caaatgctct gcaaaaggga gaaaatggca tggatgagca tcacagcgtt ctggtggaat   24240
tggaaggcga taatgccaga ctcgcagtac tcaagcgaag catcgaggtc acacacttcg   24300
catatcccgc tgtcaacctg cccctaaag tcatgacggc ggtcatggac cagttactca   24360
ttaagcgcgc aagtcccctt tcagaagaca tgcatgaccc agatgcctgt gatgagggta   24420
aaccagtggt cagtgatgag cagctaaccc gatggctggg caccgactct cccagggatt   24480
```

-continued

```
tggaagagcg tcgcaagctt atgatggccg tggtgctggt taccgtagaa ctagagtgtc    24540
tccgacgttt ctttaccgat tcagaaacct tgcgcaaact cgaagagaat ctgcactaca    24600
cttttagaca cggctttgtg cggcaggcat gcaagatatc taacgtggaa ctcaccaacc    24660
tggtttccta catgggtatt ctgcatgaga atcgcctagg acaaagcgtg ctgcacagca    24720
ccctgaaggg ggaagcccgc cgtgattaca tccgcgattg tgtctatctg tacctgtgcc    24780
acacgtggca aaccggcatg ggtgtatggc agcaatgttt agaagaacag aacttgaaag    24840
agcttgacaa gctcttacag aaatctctta aggttctgtg gacagggttc gacgagcgca    24900
ccgtcgcttc cgacctggca gacctcatct cccagagcg tctcagggtt actttgcgaa    24960
acggattgcc tgactttatg agccagagca tgcttaacaa ttttcgctct ttcatcctgg    25020
aacgctccgg tatcctgccc gccacctgct gcgcactgcc ctccgacttt gtgcctctca    25080
cctaccgcga gtgcccccg ccgctatgga gtcactgcta cctgttccgt ctggccaact    25140
atctctccta ccactcggat gtgatcgagg atgtgagcgg agacggcttg ctggagtgtc    25200
actgccgctg caatctgtgc acgccccacc ggtccctagc ttgcaacccc cagttgatga    25260
gcgaaaccca gataataggc acctttgaat tgcaaggccc cagcagccaa ggcgatgggt    25320
cttctcctgg gcaaagttta aaactgaccc cgggactgtg gacctccgcc tacttgcgca    25380
agtttgctcc ggaagattac caccctatg aaatcaagtt ctatgaggac caatcacagc    25440
ctccaaaggc cgaactttcg gcctgcgtca tcacccaggg ggcaattctg cccaattgc    25500
aagccatcca aaaatcccgc caagaatttc tactgaaaaa gggtaagggg gtctaccttg    25560
accccagac cggcgaggaa ctcaacacaa ggttccctca ggatgtccca acgacgagaa    25620
aacaagaagt tgaaggtgca gccgccgccc cagaagata tggaggaaga ttgggacagt    25680
caggcagagg aggcggagga ggacagtctg gaggacagtc tggaggaaga cagttttgag    25740
gaggaaaacg aggaggcaga ggaggtggaa gaagtaaccg ccgacaaaca gttatcctcg    25800
gctgcggaga caagcaacag cgctaccatc tccgctccga gtcgaggaac ccggcggcgt    25860
cccagcagta gatgggacga gaccggacgc ttcccgaacc caaccagcgc ttccaagacc    25920
ggtaagaagg atcggcaggg gatacaagtcc tggcgggggc ataagaatgc catcatctcc    25980
tgcttgcatg agtgcggggg caacatatcc ttcacgcggc gctacttgct attccaccat    26040
ggggtgaact ttccgcgcaa tgttttgcat tactaccgtc acctccacag cccctactat    26100
agccagcaaa tcccggcagt ctcgacagat aaagacagcg gcggcgacct ccaacagaaa    26160
accagcagcg gcagttagaa aatacacaac aagtgcagca acaggaggat taaagattac    26220
agccaacgag ccagcgcaaa cccgagagtt aagaaatcgg atctttccaa ccctgtatgc    26280
catcttccag cagagtcggg gtcaagagca ggaactgaaa ataaaaaacc gatctctgcg    26340
ttcgctcacc agaagttgtt tgtatcacaa gagcgaagat caacttcagc gcactctcga    26400
ggacgccgag gctctcttca acaagtactg cgcgctgact cttaaagagt aggcagcgac    26460
cgcgcttatt caaaaaaggc gggaattaca tcatcctcga catgagtaaa gaaattccca    26520
cgccttacat gtggagttat caaccccaaa tgggattggc ggcaggcgcc tcccaggact    26580
actccacccg catgaattgg ctcagcgccg ggccttctat gatttctcga gttaatgata    26640
tacgcgccta ccgaaaccaa atactttggg aacagtcagc tcttaccacc acgccccgcc    26700
aacaccttaa tccagaaaat tggcccgccg ccctagtgta ccaggaaagt cccgctccca    26760
ccactgtatt acttcctcga gacgcccagg ccgaagtcca aatgactaat gcaggtgcgc    26820
agttagctgg cggctccacc ctatgtcgtc acaggcctcg gcataatata aaacgcctga    26880
```

```
tgatcagagg ccgaggtatc cagctcaacg acgagtcggt gagctctccg cttggtctac   26940
gaccagacgg aatctttcag attgccggct gcgggagatc ttccttcacc cctcgtcagg   27000
ctgttctgac tttggaaagt tcgtcttcgc aaccccgctc gggcggaatc gggaccgttc   27060
aatttgtgga ggagtttact ccctctgtct acttcaaccc cttctccgga tctcctgggc   27120
attacccgga cgagttcata ccgaacttcg acgcgattag cgagtcagtg gacggctacg   27180
attgatgtct ggtgacgcgg ctgagctatc tcggctgcga catctagacc actgccgccg   27240 cttttcgctgc tttgcccggg aactcattga gttcatctac ttcgaactcc caaggatca   27300 ccctcaaggt ccgccccacg gagtgcggat ttctatcgaa ggcaaaatag actctcgcct   27360
gcaacgaatt ttctcccagc ggcccgtgct gatcgagcga gaccagggaa acaccacggt   27420
ttccatctac tgcatttgta atcaccccgg attgcatgaa agcctttgct gtcttatgtg   27480
tactgagttt aataaaaact gaattaagac tctcctacgg actgccgctt cttcaacccg   27540
gattttacaa ccagaagaac gaaacttttc ctgtcgtcca ggactctgtt aacttcacct   27600
ttcctactca caaactagaa gctcaacgac tacaccgctt ttccagaagc attttcccta   27660
ctaatactac tttcaaaacc ggaggtgagc tccaaggtct tcctacagaa aacccttggg   27720
tggaagcggg ccttgtagtg ctaggaattc ttgcgggtgg gcttgtgatt attctttgct   27780
acctatacac accttgcttc actttcttag tggtgttgtg gtattggttt aaaaaatggg   27840
gcccatacta gtcttgcttg ttttactttc gcttttggaa ccgggttctg ccaattacga   27900
tccatgtcta gacttcgacc cagaaaactg cacacttact tttgcacccg acacaagccg   27960
catctgtgga gttcatcgcc tctcttacga acttggcccc caacgacaaa aatttacctg   28020
catggtggga atcaaccccca tagttatcac ccagcaaagt ggagatacta agggttgcat   28080
tcactgctcc tgcgattcca tcgagtgcac ctacaccctg ctgaagaccc tatgcggcct   28140
aagagacctg ctaccaatga attaaaaaat gattaataaa aaatcactta cttgaaatca   28200
gcaataaggt ctctgttgaa attttctccc agcagcacct cacttccctc ttcccaactc   28260
tggtattcta aaccccgttc agcggcatac tttctccata cttttaaggg gatgtcaaat   28320
tttagctcct ctcctgtacc cacaatcttc atgtctttct tcccagatga ccaagagagt   28380
ccggctcagt gactccttca accctgtcta cccctatgaa gatgaaagca cctcccaaca   28440
cccctttata aacccagggt ttatttcccc aaatggcttc acacaaagcc caaacggagt   28500
tcttacttta aaatgtttaa ccccactaac aaccacaggc ggatctctac agctaaaagt   28560 gggagggggga cttacagtgg atgacaccaa cggttttttg aaagaaaaca taagtgccac   28620
cacaccactc gttaagactg gtcactctat aggtttacca ctaggagccg gattgggaac   28680
gaatgaaaat aaactttgta tcaaattagg acaaggactt acattcaatt caacaacat   28740 ttgcattgat gacaatatta acaccttatg gacaggagtc aaccccaccg aagccaactg   28800
tcaaatcatg aactccagtg aatctaatga ttgcaaatta attctaacac tagttaaaac   28860
tggagcacta gtcactgcat tgtttatgt tataggagta tctaacaatt ttaatatgct   28920
aactacacac agaaatataa attttactgc agagctgttt ttcgattcta ctggtaattt   28980
actaactaga ctctcatccc tcaaaactcc acttaatcat aaatcaggac aaaacatggc   29040
tactggtgcc attactaatg ctaaaggttt catgcccagc acgactgcct atccttttcaa   29100 tgataattct agagaaaaag aaaactacat ttacggaact tgttactaca cagctagtga   29160
tcgcactgct tttcccattg acatatctgt catgcttaac cgaagagcaa taatgacga   29220
```

```
gacatcatat tgtattcgta taacttggtc ctggaacaca ggagatgccc cagaggtgca   29280
aacctctgct acaaccctag tcacctcccc atttaccttt tactacatca gagaagacga   29340
ctgacaaata aagtttaact tgtttatttg aaaatcaatt cacaaaatcc gagtagttat   29400
tttgcctccc ccttcccatt taacagaata caccaatctc tccccacgca cagctttaaa   29460
catttggata ccattagata tagacatggt tttagattcc acattccaaa cagtttcaga   29520
gcgagccaat ctggggtcag tgatagataa aaatccatcg ggatagtctt ttaaagcgct   29580
ttcacagtcc aactgctgcg gatgcgactc cggagtctgg atcacggtca tctggaagaa   29640
gaacgatggg aatcataatc cgaaaacggt atcggacgat tgtgtctcat caaacccaca   29700
agcagccgct gtctgcgtcg ctccgtgcga ctgctgttta tgggatcagg gtccacagtg   29760
tcctgaagca tgattttaat agcccttaac atcaactttc tggtgcgatg cgcgcagcaa   29820
cgcattctga tttcactcaa atctttgcag taggtacaac acattattac aatattgttt   29880
aataaaccat aattaaaagc gctccagcca aaactcatat ctgatataat cgcccctgca   29940
tgaccatcat accaaagttt aatataaatt aaatgacgtt ccctcaaaaa cacactaccc   30000
acatacatga tctcttttgg catgtgcata ttaacaatct gtctgtacca tggacaacgt   30060
tggttaatca tgcaacccaa tataaccttc cggaaccaca ctgccaacac cgctccccca   30120
gccatgcatt gaagtgaacc ctgctgatta caatgacaat gaagaaccca attctctcga   30180
ccgtgaatca cttgagaatg aaaaatatct atagtggcac aacatagaca taaatgcatg   30240
catcttctca taattttaa ctcctcagga tttagaaaca tatcccaggg aataggaagc   30300
tcttgcagaa cagtaaagct ggcagaacaa ggaagaccac gaacacaact tacactatgc   30360
atagtcatag tatcacaatc tggcaacagc gggtggtctt cagtcataga agctcgggtt   30420 tcatttcct cacaacgtgg taactgggct ctggtgtaag ggtgatgtct ggcgcatgat   30480
gtcgagcgtg cgcgcaacct tgtcataatg gagttgcttc ctgacattct cgtatttgt   30540 atagcaaaac gcggccctgg cagaacacac tcttcttcgc cttctatcct gccgcttagc   30600
gtgttccgtg tgatagttca agtacaacca cactcttaag ttggtcaaaa gaatgctggc   30660
ttcagttgta atcaaaactc catcgcatct aatcgttctg aggaaatcat ccaagcaatg   30720
caactggatt gtgtttcaag caggagagga gagggaagag acggaagaac catgttaatt   30780
tttattccaa acgatctcgc agtacttcaa attgtagatc gcgcagatgg catctctcgc   30840
ccccactgtg ttggtgaaaa agcacagcta gatcaaaaga aatgcgattt tcaaggtgct   30900
caacggtggc ttccagcaaa gcctccacgc gcacatccaa gaacaaaaga ataccaaaag   30960
aaggagcatt ttctaactcc tcaatcatca tattacattc ctgcaccatt cccagataat   31020
tttcagcttt ccagccttga attattcgtg tcagttcttg tggtaaatcc aatccacaca   31080
ttacaaacag gtcccggagg gcgccctcca ccaccattct taaacacacc ctcataatga   31140
caaaatatct tgctcctgtg tcacctgtag cgaattgaga atggcaacat caattgacat   31200
gcccttggct ctaagttctt ctttaagttc tagttgtaaa aactctctca tattatcacc   31260
aaactgctta gccagaagcc cccgggaac aagagcaggg gacgctacag tgcagtacaa   31320
gcgcagacct cccaattgg ctccagcaaa aacaagattg gaataagcat attgggaacc   31380
gccagtaata tcatcgaagt tgctggaaat ataatcaggc agagtttctt gtaaaaattg   31440
aataaaagaa aaatttgcca aaaaacatt caaaacctct gggatgcaaa tgcaataggt   31500
taccgcgctg cgctccaaca ttgttagttt tgaattagtc tgcaaaaata aaaaaaaaa   31560 caagcgtcat atcatagtag cctgacgaac agatggataa atcagtcttt ccatcacaag   31620
```

```
acaagccaca gggtctccag ctcgaccctc gtaaaacctg tcatcatgat taaacaacag    31680
caccgaaagt tcctcgcggt gaccagcatg aataattctt gatgaagcat acaatccaga    31740
catgttagca tcagttaacg agaaaaaaca gccaacatag cctttgggta taattatgct    31800
taatcgtaag tatagcaaag ccacccctcg cggatacaaa gtaaaaggca caggagaata    31860
aaaaatataa ttatttctct gctgctgttc aggcaacgtc gccccggtc cctctaaata     31920 cacatacaaa gcctcatcag ccatggctta ccagacaaag tacagcgggc acacaaagca    31980
caagctctaa agtgactctc caacctctcc acaatatata tatacacaag ccctaaactg    32040
acgtaatggg agtaaagtgt aaaaaatccc gccaaaccca acacacaccc cgaaactgcg    32100
tcaccaggga aaagtacagt ttcacttccg caatcccaac aggcgtaact tcctctttct    32160
cacggtacgt gatatcccac taacttgcaa cgtcattttc ccacggtcgc accgcccctt    32220
ttagccgtta accccacagc caatcaccac acgatccaca ctttttaaaa tcacctcatt    32280
tacatattgg caccattcca tctataaggt atattatata gataga                   32326
```

```
<210> SEQ ID NO 2
<211> LENGTH: 201
<212> TYPE: DNA
<213> ORGANISM: Artificial Sequence
<220> FEATURE:
<223> OTHER INFORMATION: A non-coding sequence suitable for inclusion
      into BX

<400> SEQUENCE: 2
aaaatgatta ataaaaaatc acttacttga aatcagcaat aaggtctctg ttgaaatttt    60
ctcccagcag cacctcactt ccctcttccc aactctggta ttctaaaccc cgttcagcgg   120
catactttct ccatacttta aaggggatgt caaattttag ctcctctcct gtacccacaa   180
tcttcatgtc tttcttccca g                                             201

<210> SEQ ID NO 3
<211> LENGTH: 34
<212> TYPE: DNA
<213> ORGANISM: Artificial Sequence
<220> FEATURE:
<223> OTHER INFORMATION: A non-coding sequence suitable for inclusion
      into BY

<400> SEQUENCE: 3
caaataaagt ttaacttgtt tatttgaaaa tcaa                                34

<210> SEQ ID NO 4
<211> LENGTH: 19
<212> TYPE: DNA
<213> ORGANISM: Artificial Sequence
<220> FEATURE:
<223> OTHER INFORMATION: A restriction site insert

<400> SEQUENCE: 4
gcgatcgcta ccctgcagg                                                 19

<210> SEQ ID NO 5
<211> LENGTH: 19
<212> TYPE: DNA
<213> ORGANISM: Artificial Sequence
<220> FEATURE:
<223> OTHER INFORMATION: A restriction site insert

<400> SEQUENCE: 5
```

```
gcggccgcta tggccggcc                                                  19

<210> SEQ ID NO 6
<211> LENGTH: 192
<212> TYPE: DNA
<213> ORGANISM: Artificial Sequence
<220> FEATURE:
<223> OTHER INFORMATION: A polyadenylation sequence

<400> SEQUENCE: 6
cagacatgat aagatacatt gatgagtttg gacaaaccac aactagaatg cagtgaaaaa    60
aatgctttat ttgtgaaatt tgtgatgcta ttgctttatt tgtaaccatt ataagctgca   120
ataaacaagt taacaacaac aattgcattc attttatgtt tcaggttcag ggggaggtgt   180
gggaggtttt tt                                                       192

<210> SEQ ID NO 7
<211> LENGTH: 981
<212> TYPE: DNA
<213> ORGANISM: Artificial Sequence
<220> FEATURE:
<223> OTHER INFORMATION: E3 region from EnAd

<400> SEQUENCE: 7
atgtctggtg acgcggctga gctatctcgg ctgcgacatc tagaccactg ccgccgcttt    60
cgctgctttg cccgggaact cattgagttc atctacttcg aactccccaa ggatcaccct   120
caaggtccgg cccacggagt gcggatttct atcgaaggca aaatagactc tcgcctgcaa   180
cgaattttct cccagcggcc cgtgctgatc gagcgagacc agggaaacac cacggtttcc   240
atctactgca tttgtaatca ccccggattg catgaaagcc tttgctgtct tatgtgtact   300 gagttttaata aaaactgaat taagactctc ctacggactg ccgcttcttc aacccggatt   360
ttacaaccag aagaacgaaa cttttcctgt cgtccaggac tctgttaact tcacctttcc   420
tactcacaaa ctagaagctc aacgactaca ccgcttttcc agaagcattt tccctactaa   480
tactactttc aaaaccggag gtgagctcca aggtcttcct acagaaaacc cttgggtgga   540
agcgggcctt gtagtgctag gaattcttgc gggtgggctt tgattattc tttgctacct   600 atacacacct tgcttcactt tcttagtggt gttgtggtat tggtttaaaa aatggggccc   660
atactagtct tgcttgtttt actttcgctt tggaaccggg ttctgccaa ttacgatcca   720 tgtctagact tcgacccaga aaactgcaca cttacttttg caccccgacac aagccgcatc   780 tgtggagttc atcgcctctc ttacgaactt ggccccaac gacaaaaatt tacctgcatg   840
gtgggaatca accccatagt tatcacccag caaagtggag atactaaggg ttgcattcac   900
tgctcctgcg attccatcga gtgcacctac accctgctga gaccctatg cggcctaaga   960 gacctgctac caatgaatta a                                             981

<210> SEQ ID NO 8
<211> LENGTH: 5287
<212> TYPE: DNA
<213> ORGANISM: Artificial Sequence
<220> FEATURE:
<223> OTHER INFORMATION: E2B region from EnAd

<400> SEQUENCE: 8
ctatggcatc tcgatccagc agacctcctc gtttcgcggg tttggacggc tcctggaata    60
gggtatgaga cgatgggcgt ccagcgctgc cagggttcgg tccttccagg gtctcagtgt   120
tcgagtcagg gttgtttccg tcacagtgaa ggggtgtgcg cctgcttggg cgcttgccag   180
```

```
ggtgcgcttc agactcatcc tgctggtcga aaacttctgt cgcttggcgc cctgtatgtc    240
ggccaagtag cagtttacca tgagttcgta gttgagcgcc tcggctgcgt ggcctttggc    300
gcggagctta cctttggaag ttttcttgca taccgggcag tataggcatt tcagcgcata    360
caacttgggc gcaaggaaaa cggattctgg ggagtatgca tctgcgccgc aggaggcgca    420
aacagtttca cattccacca gccaggttaa atccggttca ttggggtcaa aaacaagttt    480
tccgccatat tttttgatgc gtttcttacc tttggtctcc atgagttcgt gtcctcgttg    540
agtgacaaac aggctgtccg tgtccccgta gactgatttt acaggcctct tctccagtgg    600
agtgcctcgg tcttcttcgt acaggaactc tgaccactct gatacaaagg cgcgcgtcca    660
ggccagcaca aaggaggcta tgtgggaggg gtagcgatcg ttgtcaacca ggggggtccac   720 cttttccaaa gtatgcaaac acatgtcacc ctcttcaaca tccaggaatg tgattggctt    780
gtaggtgtat ttcacgtgac ctggggtccc cgctgggggg gtataaaagg gggcggttct    840
ttgctcttcc tcactgtctt ccggatcgct gtccaggaac gtcagctgtt ggggtaggta    900
ttccctctcg aaggcgggca tgacctctgc actcaggttg tcagtttcta agaacgagga    960
ggatttgata ttgacagtgc cggttgagat gcctttcatg aggttttcgt ccatctggtc   1020
agaaaacaca atttttttat tgtcaagttt ggtggcaaat gatccataca gggcgttgga   1080
taaaagtttg gcaatggatc gcatggtttg gttcttttcc ttgtccgcgc gctctttggc   1140
ggcgatgttg agttggacat actcgcgtgc caggcacttc cattcgggga agatagttgt   1200
taattcatct ggcacgattc tcacttgcca ccctcgatta tgcaaggtaa ttaaatccac   1260
actggtggcc acctcgcctc gaaggggttc attggtccaa cagagcctac ctcctttcct   1320
agaacagaaa gggggaagtg ggtctagcat aagttcatcg ggagggtctg catccatggt   1380
aaagattccc ggaagtaaat ccttatcaaa atagctgatg ggagtggggt catctaaggc   1440
catttgccat tctcgagctg ccagtgcgcg ctcatatggg ttaaggggac tgccccatgg   1500
catgggatgg gtgagtgcag aggcatacat gccacagatg tcatagacgt agatgggatc   1560
ctcaaagatg cctatgtagg ttggatagca tcgccccccct ctgatacttg ctcgcacata   1620
gtcatatagt tcatgtgatg cgctagcag ccccggaccc aagttggtgc gattgggttt     1680
ttctgttctg tagacgatct ggcgaaagat ggcgtgagaa ttggaagaga tggtgggtct   1740
ttgaaaaatg ttgaaatggg catgaggtag acctacagag tctctgacaa agtgggcata   1800
agattcttga agcttggtta ccagttcggc ggtgacaagt acgtctaggg cgcagtagtc   1860
aagtgtttct tgaatgatgt cataacctgg ttggttttttc ttttcccaca gttcgcggtt   1920
gagaaggtat tcttcgcgat ccttccagta ctcttctagc ggaaacccgt ctttgtctgc   1980
acggtaagat cctagcatgt agaactgatt aactgccttg taaggcagc agcccttctc    2040 tacgggtaga gagtatgctt gagcagcttt tcgtagcgaa gcgtgagtaa gggcaaaggt   2100
gtctctgacc atgactttga ggaattggta tttgaagtcg atgtcgtcac aggctccctg   2160
ttcccagagt tggaagtcta cccgtttctt gtaggcgggg ttgggcaaag cgaaagtaac   2220
atcattgaag agaatcttgc cggccctggg catgaaattg cgagtgatgc gaaaaggctg   2280
tggtacttcc gctcggttat tgataacctg ggcagctagg acgatctcgt cgaaaccgtt   2340
gatgttgtgt cctacgatgt ataattctat gaaacgcggc gtgcctctga cgtgaggtag   2400
cttactgagc tcatcaaagg ttaggtctgt ggggtcagat aaggcgtagt gttcgagagc   2460
ccattcgtgc aggtgaggat tcgctttaag gaaggaggac cagaggtcca ctgccagtgc   2520
```

```
tgtttgtaac tggtcccggt actgacgaaa atgccgtccg actgccattt tttctggggt   2580
gacgcaatag aaggtttggg ggtcctgccg ccagcgatcc cacttgagtt ttatggcgag   2640
gtcataggcg atgttgacga gccgctggtc tccagagagt ttcatgacca gcatgaaggg   2700
gattagctgc ttgccaaagg accccatcca ggtgtaggtt tccacatcgt aggtgagaaa   2760
gagcctttct gtgcgaggat gagagccaat cgggaagaac tggatctcct gccaccagtt   2820
ggaggaatgg ctgttgatgt gatggaagta gaactccctg cgacgcgccg agcattcatg   2880
cttgtgcttg tacagacggc cgcagtagtc gcagcgttgc acgggttgta tctcgtgaat   2940
gagttgtacc tggcttccct tgacgagaaa tttcagtggg aagccgaggc ctggcgattg   3000
tatctcgtgc tttactatgt tgtctgcatc ggcctgttca tcttctgtct cgatggtggt   3060
catgctgacg agccctcgcg ggaggcaagt ccagacctcg gcgcggcagg gcggagctc    3120 gaggacgaga gcgcgcaggc tggagctgtc cagggtcctg agacgctgcg gactcaggtt   3180
agtaggcagt gtcaggagat taacttgcat gatcttttgg agggcgtgcg ggaggttcag   3240
atagtacttg atctcaacgg gtccgttggt ggagatgtcg atggcttgca gggttccgtg   3300
tcccttgggc gctaccaccg tgcccttgtt tttcattttg gacggcggtg gctctgttgc   3360
ttcttgcatg tttagaagcg gtgtcgaggg cgcgcaccgg gcggcagggg cggctcggga   3420
cccggcggca tggctggcag tggtacgtcg gcgccgcgcg cgggtaggtt ctggtactgc   3480
gccctgagaa gactcgcatg cgcgacgacg cggcggttga catcctggat ctgacgcctc   3540
tgggtgaaag ctaccggccc cgtgagcttg aacctgaaag agagttcaac agaatcaatc   3600
tcggtatcgt tgacgcggc  ttgcctaagg atttcttgca cgtcaccaga gttgtcctgg   3660
taggcgatct ccgccatgaa ctgctcgatc tcttcctctt gaagatctcc gcggcccgct   3720
ctctcgacgg tggccgcgag gtcgttggag atgcgcccaa tgagttgaga gaatgcattc   3780
atgcccgcct cgttccagac gcggctgtag accacggccc ccacgggatc tctcgcgcgc   3840
atgaccacct gggcgaggtt gagctccacg tggcgggtga agaccgcata gttgcatagg   3900
cgctggaaaa ggtagttgag tgtggtggcg atgtgctcgg tgacgaagaa atacatgatc   3960
catcgtctca gcggcatctc gctgacatcg cccagagctt ccaagcgctc catggcctcg   4020
tagaagtcca cggcaaaatt aaaaaactgg gagtttcgcg cggacacggt caactcctct   4080
tccagaagac ggataagttc ggcgatggtg gtgcgcacct cgcgctcgaa agccctgggg   4140
atttcttcct caatctcttc ttcttccact aacatctctt cctcttcagg tggggctgca   4200
ggaggagggg gaacgcggcg acgccggcgg cgcacgggca gacggtcgat gaatctttca   4260
atgacctctc cgcggcggcg gcgcatggtt tcagtgacgg cgcggccgtt ctcgcgcggt   4320
cgcagagtaa aaacaccgcc gcgcatctcc ttaaagtggt gactgggagg ttctccgttt   4380
ggagggagag ggcgctgatt atacatttta ttaattggcc cgtagggact gcacgcagag   4440
atctgatcgt gtcaagatcc acgggatctg aaaacctttc gacgaaagcg tctaaccagt   4500
cacagtcaca aggtaggctg agtacggctt cttgtgggcg ggggtggtta tgtgttcggt   4560
ctgggtcttc tgtttcttct tcatctcggg aaggtgagac gatgctgctg gtgatgaaat   4620
taaagtaggc agttctaaga cggcggatgg tggcgaggag caccaggtct ttgggtccgg   4680
cttgctggat acgcaggcga ttggccattc cccaagcatt atcctgacat ctagcaagat   4740
ctttgtagta gtcttgcatg agccgttcta cgggcacttc ttcctcaccc gttctgccat   4800
gcatacgtgt gagtccaaat ccgcgcattg gttgtaccag tgccaagtca gctacgactc   4860
tttcggcgag gatggcttgc tgtacttggg taagggtggc ttgaaagtca tcaaaatcca   4920
```

```
caaagcggtg gtaagctcct gtattaatgg tgtaagcaca gttggccatg actgaccagt    4980
taactgtctg gtgaccaggg cgcacgagct cggtgtattt aaggcgcgaa taggcgcggg    5040
tgtcaaagat gtaatcgttg caggtgcgca ccagatactg gtaccctata agaaaatgcg    5100
gcggtggttg gcggtagaga ggccatcgtt ctgtagctgg agcgccaggg gcgaggtctt    5160
ccaacataag gcggtgatag ccgtagatgt acctggacat ccaggtgatt cctgcggcgg    5220
tagtagaagc ccgaggaaac tcgcgtacgc ggttccaaat gttgcgtagc ggcatgaagt    5280
agttcat                                                              5287
```

<210> SEQ ID NO 9
<211> LENGTH: 123
<212> TYPE: PRT
<213> ORGANISM: Artificial Sequence
<220> FEATURE:
<223> OTHER INFORMATION: anti-VEGF ab VH chain amino acid sequence

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 10
<211> LENGTH: 118
<212> TYPE: PRT
<213> ORGANISM: Artificial Sequence
<220> FEATURE:
<223> OTHER INFORMATION: anti-PD-L1 antibody VH chain amino acid
      sequence

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
```

```
                 100             105             110

Leu Val Thr Val Ser Ala
            115

<210> SEQ ID NO 11
<211> LENGTH: 108
<212> TYPE: PRT
<213> ORGANISM: Artificial Sequence
<220> FEATURE:
<223> OTHER INFORMATION: anti-VEGF ab VL chain amino acid sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 12
<211> LENGTH: 108
<212> TYPE: PRT
<213> ORGANISM: Artificial Sequence
<220> FEATURE:
<223> OTHER INFORMATION: anti-PD-L1 antibody VL chain amino acid
      sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 13
<211> LENGTH: 330
<212> TYPE: PRT
<213> ORGANISM: Artificial Sequence
<220> FEATURE:
<223> OTHER INFORMATION: human IgG1 constant heavy chain amino acid
      sequence

<400> SEQUENCE: 13
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 330
<212> TYPE: PRT
<213> ORGANISM: Artificial Sequence
<220> FEATURE:
<223> OTHER INFORMATION: human IgG1 modified constant heavy chain amino
      acid sequence

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 105
<212> TYPE: PRT
<213> ORGANISM: Artificial Sequence
<220> FEATURE:
<223> OTHER INFORMATION: human kappa constant light chain amino acid
      sequence

<400> SEQUENCE: 15

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
```

```
                50                  55                  60
Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu Cys
            100                 105

<210> SEQ ID NO 16
<211> LENGTH: 264
<212> TYPE: PRT
<213> ORGANISM: Artificial Sequence
<220> FEATURE:
<223> OTHER INFORMATION: anti-VEGF ScFv amino acid sequence

<400> SEQUENCE: 16

Met Gly Trp Ser Cys Ile Ile Leu Phe Leu Val Ala Thr Ala Thr Gly
  1               5                  10                  15

Val His Ser Glu Val Gln Leu Val Glu Ser Gly Gly Gly Leu Val Pro
                 20                  25                  30

Gly Gly Ser Leu Arg Leu Ser Cys Ala Ala Ser Gly Tyr Thr Phe Thr
             35                  40                  45

Asn Tyr Gly Met Asn Trp Val Arg Gln Ala Pro Gly Lys Gly Leu Glu
         50                  55                  60

Trp Val Gly Trp Ile Asn Thr Tyr Thr Gly Glu Pro Thr Tyr Ala Ala
 65                  70                  75                  80

Asp Phe Lys Arg Arg Phe Thr Phe Ser Leu Asp Thr Ser Lys Ser Thr
                 85                  90                  95

Ala Tyr Leu Gln Met Asn Ser Leu Arg Ala Glu Asp Thr Ala Val Tyr
            100                 105                 110

Tyr Cys Ala Lys Tyr Pro His Tyr Tyr Gly Ser Ser His Trp Tyr Phe
        115                 120                 125

Asp Val Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Thr Cys Ser Ala Ser Gln Asp Ile Ser Asn Tyr Leu Asn Trp Tyr
            180                 185                 190

Gln Gln Lys Pro Gly Lys Ala Pro Lys Val Leu Ile Tyr Phe Thr Ser
        195                 200                 205

Ser Leu His Ser Gly Val Pro Ser Arg Phe Ser Gly Ser Gly Ser Gly
    210                 215                 220

Thr Asp Phe Thr Leu Thr Ile Ser Ser Leu Gln Pro Glu Asp Phe Ala
225                 230                 235                 240

Thr Tyr Tyr Cys Gln Gln Tyr Ser Thr Val Pro Trp Thr Phe Gly Gln
                245                 250                 255

Gly Thr Lys Val Glu Ile Lys Arg
            260

<210> SEQ ID NO 17
<211> LENGTH: 260
<212> TYPE: PRT
<213> ORGANISM: Artificial Sequence
<220> FEATURE:
<223> OTHER INFORMATION: anti-PD-L1 ScFv amino acid sequence
```

<400> SEQUENCE: 17

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asp Ser Trp Ile His Trp Val Arg Gln Ala Pro Gly Lys Gly Leu
    50                  55                  60

Glu Trp Val Ala Trp Ile Ser Pro Tyr Gly Gly Ser Thr Tyr Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Arg His Trp Pro Gly Gly Phe Asp Tyr Trp Gly
        115                 120                 125

Gln Gly Thr Leu Val Thr Val Ser Ala Gly Gly Gly Ser Gly Gly
130                 135                 140

Gly Gly Ser Gly Gly Gly Ser Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Asp Val Ser Thr Ala Val Ala Trp Tyr Gln Gln Lys Pro
            180                 185                 190

Gly Lys Ala Pro Lys Leu Leu Ile Tyr Ser Ala Ser Phe Leu Tyr Ser
        195                 200                 205

Gly Val Pro Ser Arg Phe Ser Gly Ser Gly Ser Gly Thr Asp Phe Thr
    210                 215                 220

Leu Thr Ile Ser Ser Leu Gln Pro Glu Asp Phe Ala Thr Tyr Tyr Cys
225                 230                 235                 240

Gln Gln Tyr Leu Tyr His Pro Ala Thr Phe Gly Gln Gly Thr Lys Val
                245                 250                 255

Glu Ile Lys Arg
            260
```

<210> SEQ ID NO 18
<211> LENGTH: 239
<212> TYPE: PRT
<213> ORGANISM: Artificial Sequence
<220> FEATURE:
<223> OTHER INFORMATION: Green fluorescent protein amino acid sequence

<400> SEQUENCE: 18

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80
```

Gln His Asp Phe Phe Lys Ser Ala Met Pro Glu Gly Tyr Val Gln Glu
            85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 19
<211> LENGTH: 550
<212> TYPE: PRT
<213> ORGANISM: Artificial Sequence
<220> FEATURE:
<223> OTHER INFORMATION: Luciferase amino acid sequence

<400> SEQUENCE: 19

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
            35                  40                  45

Val Asp Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
            85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
            130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

```
Ala Leu Pro His Arg Thr Ala Cys Val Arg Phe Ser His Ala Arg Asp
    210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
    290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
    370                 375                 380
Asn Gln Arg Gly Glu Leu Cys Val Arg Gly Pro Met Ile Met Ser Gly
385                 390                 395                 400
Tyr Val Asn Asn Pro Glu Ala Thr Asn Ala Leu Ile Asp Lys Asp Gly
                405                 410                 415
Trp Leu His Ser Gly Asp Ile Ala Tyr Trp Asp Glu Asp Glu His Phe
            420                 425                 430
Phe Ile Val Asp Arg Leu Lys Ser Leu Ile Lys Tyr Lys Gly Tyr Gln
        435                 440                 445
Val Ala Pro Ala Glu Leu Glu Ser Ile Leu Leu Gln His Pro Asn Ile
    450                 455                 460
Phe Asp Ala Gly Val Ala Gly Leu Pro Asp Asp Asp Ala Gly Glu Leu
465                 470                 475                 480
Pro Ala Ala Val Val Val Leu Glu His Gly Lys Thr Met Thr Glu Lys
                485                 490                 495
Glu Ile Val Asp Tyr Val Ala Ser Gln Val Thr Thr Ala Lys Lys Leu
            500                 505                 510
Arg Gly Gly Val Val Phe Val Asp Glu Val Pro Lys Gly Leu Thr Gly
        515                 520                 525
Lys Leu Asp Ala Arg Lys Ile Arg Glu Ile Leu Ile Lys Ala Lys Lys
    530                 535                 540
Gly Gly Lys Ile Ala Val
545                 550

<210> SEQ ID NO 20
<211> LENGTH: 233
<212> TYPE: PRT
<213> ORGANISM: Artificial Sequence
<220> FEATURE:
<223> OTHER INFORMATION: Human Tumour necrosis factor alpha amino acid
      sequence

<400> SEQUENCE: 20

Met Ser Thr Glu Ser Met Ile Arg Asp Val Glu Leu Ala Glu Glu Ala
1               5                   10                  15
```

```
Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 21
<211> LENGTH: 166
<212> TYPE: PRT
<213> ORGANISM: Artificial Sequence
<220> FEATURE:
<223> OTHER INFORMATION: Human Interferon gamma amino acid sequence

<400> SEQUENCE: 21

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140
```

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 22
<211> LENGTH: 188
<212> TYPE: PRT
<213> ORGANISM: Artificial Sequence
<220> FEATURE:
<223> OTHER INFORMATION: Human Interferon alpha amino acid sequence

<400> SEQUENCE: 22

Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 23
<211> LENGTH: 180
<212> TYPE: PRT
<213> ORGANISM: Artificial Sequence
<220> FEATURE:
<223> OTHER INFORMATION: human cancer/testis angtigen 1 (NY-ESO-1) amino
      acid sequence

<400> SEQUENCE: 23

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                    85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 24
<211> LENGTH: 1255
<212> TYPE: PRT
<213> ORGANISM: Artificial Sequence
<220> FEATURE:
<223> OTHER INFORMATION: Human MUC-1 amino acid sequence

<400> SEQUENCE: 24

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
        50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
            115                 120                 125

Gly Ser Thr Ala Pro Pro Ala His Gly Val Thr Ser Ala Pro Asp Thr
            130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
            195                 200                 205

Gly Ser Thr Ala Pro Pro Ala His Gly Val Thr Ser Ala Pro Asp Thr
            210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

```
Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
```

-continued

```
                    675                 680                 685
Gly Ser Thr Ala Pro Pro Ala His Gly Val Thr Ser Ala Pro Asp Thr
            690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
            770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
            820                 825                 830
Pro Pro Ala His Gly Val Thr Ser Ala Pro Asp Thr Arg Pro Ala Pro
            835                 840                 845
Gly Ser Thr Ala Pro Pro Ala His Gly Val Thr Ser Ala Pro Asp Thr
            850                 855                 860
Arg Pro Ala Pro Gly Ser Thr Ala Pro Pro Ala His Gly Val Thr Ser
865                 870                 875                 880
Ala Pro Asp Thr Arg Pro Ala Pro Gly Ser Thr Ala Pro Pro Ala His
                885                 890                 895
Gly Val Thr Ser Ala Pro Asp Thr Arg Pro Ala Pro Gly Ser Thr Ala
            900                 905                 910
Pro Pro Ala His Gly Val Thr Ser Ala Pro Asp Thr Arg Pro Ala Pro
            915                 920                 925
Gly Ser Thr Ala Pro Pro Ala His Gly Val Thr Ser Ala Pro Asp Asn
            930                 935                 940
Arg Pro Ala Leu Gly Ser Thr Ala Pro Pro Val His Asn Val Thr Ser
945                 950                 955                 960
Ala Ser Gly Ser Ala Ser Gly Ser Ala Ser Thr Leu Val His Asn Gly
                965                 970                 975
Thr Ser Ala Arg Ala Thr Thr Thr Pro Ala Ser Lys Ser Thr Pro Phe
            980                 985                 990
Ser Ile Pro Ser His His Ser Asp Thr Pro Thr Thr Leu Ala Ser His
            995                 1000                1005
Ser Thr Lys Thr Asp Ala Ser Ser Thr His His Ser Ser Val Pro
            1010                1015                1020
Pro Leu Thr Ser Ser Asn His Ser Thr Ser Pro Gln Leu Ser Thr
            1025                1030                1035
Gly Val Ser Phe Phe Phe Leu Ser Phe His Ile Ser Asn Leu Gln
            1040                1045                1050
Phe Asn Ser Ser Leu Glu Asp Pro Ser Thr Asp Tyr Tyr Gln Glu
            1055                1060                1065
Leu Gln Arg Asp Ile Ser Glu Met Phe Leu Gln Ile Tyr Lys Gln
            1070                1075                1080
Gly Gly Phe Leu Gly Leu Ser Asn Ile Lys Phe Arg Pro Gly Ser
            1085                1090                1095
```

```
Val Val Val Gln Leu Thr Leu Ala Phe Arg Glu Gly Thr Ile Asn
    1100            1105               1110

Val His Asp Val Glu Thr Gln Phe Asn Gln Tyr Lys Thr Glu Ala
    1115            1120               1125

Ala Ser Arg Tyr Asn Leu Thr Ile Ser Asp Val Ser Val Ser Asp
    1130            1135               1140

Val Pro Phe Pro Phe Ser Ala Gln Ser Gly Ala Gly Val Pro Gly
    1145            1150               1155

Trp Gly Ile Ala Leu Leu Val Leu Val Cys Val Leu Val Ala Leu
    1160            1165               1170

Ala Ile Val Tyr Leu Ile Ala Leu Ala Val Cys Gln Cys Arg Arg
    1175            1180               1185

Lys Asn Tyr Gly Gln Leu Asp Ile Phe Pro Ala Arg Asp Thr Tyr
    1190            1195               1200

His Pro Met Ser Glu Tyr Pro Thr Tyr His Thr His Gly Arg Tyr
    1205            1210               1215

Val Pro Pro Ser Ser Thr Asp Arg Ser Pro Tyr Glu Lys Val Ser
    1220            1225               1230

Ala Gly Asn Gly Gly Ser Ser Leu Ser Tyr Thr Asn Pro Ala Val
    1235            1240               1245

Ala Ala Thr Ser Ala Asn Leu
    1250            1255

<210> SEQ ID NO 25
<211> LENGTH: 643
<212> TYPE: PRT
<213> ORGANISM: Artificial Sequence
<220> FEATURE:
<223> OTHER INFORMATION: Sodium Iodide symporter (NIS) amino acid
      sequence

<400> SEQUENCE: 25

Met Glu Ala Val Glu Thr Gly Glu Arg Pro Thr Phe Gly Ala Trp Asp
1               5                   10                  15

Tyr Gly Val Phe Ala Leu Met Leu Leu Val Ser Thr Gly Ile Gly Leu
                20                  25                  30

Trp Val Gly Leu Ala Arg Gly Gly Gln Arg Ser Ala Glu Asp Phe Phe
            35                  40                  45

Thr Gly Gly Arg Arg Leu Ala Ala Leu Pro Val Gly Leu Ser Leu Ser
    50                  55                  60

Ala Ser Phe Met Ser Ala Val Gln Val Leu Gly Val Pro Ser Glu Ala
65                  70                  75                  80

Tyr Arg Tyr Gly Leu Lys Phe Leu Trp Met Cys Leu Gly Gln Leu Leu
                85                  90                  95

Asn Ser Val Leu Thr Ala Leu Leu Phe Met Pro Val Phe Tyr Arg Leu
                100                 105                 110

Gly Leu Thr Ser Thr Tyr Glu Tyr Leu Glu Met Arg Phe Ser Arg Ala
            115                 120                 125

Val Arg Leu Cys Gly Thr Leu Gln Tyr Ile Val Ala Thr Met Leu Tyr
    130                 135                 140

Thr Gly Ile Val Ile Tyr Ala Pro Ala Leu Ile Leu Asn Gln Val Thr
145                 150                 155                 160

Gly Leu Asp Ile Trp Ala Ser Leu Leu Ser Thr Gly Ile Ile Cys Thr
                165                 170                 175

Phe Tyr Thr Ala Val Gly Gly Met Lys Ala Val Val Trp Thr Asp Val
```

```
                180             185             190
Phe Gln Val Val Val Met Leu Ser Gly Phe Trp Val Leu Ala Arg
            195             200             205
Gly Val Met Leu Val Gly Gly Pro Arg Gln Val Leu Thr Leu Ala Gln
            210             215             220
Asn His Ser Arg Ile Asn Leu Met Asp Phe Asn Pro Asp Pro Arg Ser
225             230             235             240
Arg Tyr Thr Phe Trp Thr Phe Val Val Gly Thr Leu Val Trp Leu
            245             250             255
Ser Met Tyr Gly Val Asn Gln Ala Gln Val Gln Arg Tyr Val Ala Cys
            260             265             270
Arg Thr Glu Lys Gln Ala Lys Leu Ala Leu Leu Ile Asn Gln Val Gly
            275             280             285
Leu Phe Leu Ile Val Ser Ala Ala Cys Cys Gly Ile Val Met Phe
            290             295             300
Val Phe Tyr Thr Asp Cys Asp Pro Leu Leu Leu Gly Arg Ile Ser Ala
305             310             315             320
Pro Asp Gln Tyr Met Pro Leu Val Leu Asp Ile Phe Glu Asp Leu
            325             330             335
Pro Gly Val Pro Gly Leu Phe Leu Ala Cys Ala Tyr Ser Gly Thr Leu
            340             345             350
Ser Thr Ala Ser Thr Ser Ile Asn Ala Met Ala Ala Val Thr Val Glu
            355             360             365
Asp Leu Ile Lys Pro Arg Leu Arg Ser Leu Ala Pro Arg Lys Leu Val
            370             375             380
Ile Ile Ser Lys Gly Leu Ser Leu Ile Tyr Gly Ser Ala Cys Leu Thr
385             390             395             400
Val Ala Ala Leu Ser Ser Leu Leu Gly Gly Val Leu Gln Gly Ser
            405             410             415
Phe Thr Val Met Gly Val Ile Ser Gly Pro Leu Leu Gly Ala Phe Ile
            420             425             430
Leu Gly Met Phe Leu Pro Ala Cys Asn Thr Pro Gly Val Leu Ala Gly
            435             440             445
Leu Gly Ala Gly Leu Ala Leu Ser Leu Trp Val Ala Leu Gly Ala Thr
            450             455             460
Leu Tyr Pro Pro Ser Glu Gln Thr Met Arg Val Leu Pro Ser Ser Ala
465             470             475             480
Ala Arg Cys Val Ala Leu Ser Val Asn Ala Ser Gly Leu Leu Asp Pro
            485             490             495
Ala Leu Leu Pro Ala Asn Asp Ser Ser Arg Ala Pro Ser Ser Gly Met
            500             505             510
Asp Ala Ser Arg Pro Ala Leu Ala Asp Ser Phe Tyr Ala Ile Ser Tyr
            515             520             525
Leu Tyr Tyr Gly Ala Leu Gly Thr Leu Thr Thr Val Leu Cys Gly Ala
            530             535             540
Leu Ile Ser Cys Leu Thr Gly Pro Thr Lys Arg Ser Thr Leu Ala Pro
545             550             555             560
Gly Leu Leu Trp Trp Asp Leu Ala Arg Gln Thr Ala Ser Val Ala Pro
            565             570             575
Lys Glu Glu Val Ala Ile Leu Asp Asp Asn Leu Val Lys Gly Pro Glu
            580             585             590
Glu Leu Pro Thr Gly Asn Lys Lys Pro Pro Gly Phe Leu Pro Thr Asn
            595             600             605
```

```
Glu Asp Arg Leu Phe Phe Leu Gly Gln Lys Glu Leu Glu Gly Ala Gly
    610                 615                 620

Ser Trp Thr Pro Cys Val Gly His Asp Gly Arg Asp Gln Gln Glu
625                 630                 635                 640

Thr Asn Leu

<210> SEQ ID NO 26
<211> LENGTH: 125
<212> TYPE: PRT
<213> ORGANISM: Artificial Sequence
<220> FEATURE:
<223> OTHER INFORMATION: anti-CTLA-4 VH chain amino acid sequence

<400> SEQUENCE: 26

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser
        115                 120                 125

<210> SEQ ID NO 27
<211> LENGTH: 108
<212> TYPE: PRT
<213> ORGANISM: Artificial Sequence
<220> FEATURE:
<223> OTHER INFORMATION: anti-CTLA-4 VL chain amino acid sequence

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
                85                  90                  95

Thr Phe Gly Pro Gly Thr Lys Val Glu Ile Lys Arg
            100                 105

<210> SEQ ID NO 28
<211> LENGTH: 32351
<212> TYPE: DNA
<213> ORGANISM: Artificial Sequence
```

<220> FEATURE:
<223> OTHER INFORMATION: NG-184 Genome Sequence (EnAd genome with Ad11p E4 orf 4)

<400> SEQUENCE: 28

```
tctatctata taatatacct tatagatgga atggtgccaa tatgtaaatg aggtgatttt      60
aaaaagtgtg gatcgtgtgg tgattggctg tggggttaac ggctaaaagg ggcggtgcga     120
ccgtgggaaa atgacgtttt gtgggggtgg agttttttg caagttgtcg cgggaaatgt      180
gacgcataaa aaggcttttt tctcacggaa ctacttagtt ttcccacggt atttaacagg     240
aaatgaggta gttttgaccg gatgcaagtg aaaattgttg attttcgcgc gaaaactgaa     300
tgaggaagtg tttttctgaa taatgtggta tttatggcag ggtggagtat ttgttcaggg     360
ccaggtagac tttgacccat tacgtggagg tttcgattac cgtgtttttt acctgaattt     420
ccgcgtaccg tgtcaaagtc ttctgttttt acgtaggtgt cagctgatcg ctagggtatt     480
tatacctcag ggtttgtgtc aagaggccac tcttgagtgc cagcgagaag agttttctcc     540
tctgcgccgg cagtttaata ataaaaaaat gagagatttg cgattctgc ctcaggaaat      600
aatctctgct gagactggaa atgaaatatt ggagcttgtg gtgcacgccc tgatgggaga     660
cgatccggag ccacctgtgc agcttttga gcctcctacg cttcaggaac tgtatgattt      720
agaggtagag ggatcggagg attctaatga ggaagctgta aatggctttt ttaccgattc     780
tatgctttta gctgctaatg aagggttaga attagatccg cctttggaca cttttgatac     840
tccaggggta attgtggaaa gcggtacagg tgtaagaaaa ttacctgatt tgagttccgt     900
ggactgtgat ttgcactgct atgaagacgg gtttcctccg agtgatgagg aggaccatga     960
aaaggagcag tccatgcaga ctgcagcggg tgagggagtg aaggctgcca atgttggttt    1020
tcagttggat tgcccggagc ttcctggaca tggctgtaag tcttgtgaat ttcacaggaa    1080
aaatactgga gtaaaggaac tgttatgttc gctttgttat atgagaacgc actgccactt    1140
tatttacagt aagtgtgttt aagttaaaat ttaaaggaat atgctgtttt tcacatgtat    1200
attgagtgtg agttttgtgc ttcttattat aggtcctgtg tctgatgctg atgaatcacc    1260
atctcctgat tctactacct cacctcctga gattcaagca cctgttcctg tggacgtgcg    1320
caagcccatt cctgtgaagc ttaagcctgg gaaacgtcca gcagtggaaa aacttgagga    1380
cttgttacag ggtggggacg gacctttgga cttgagtaca cggaaacgtc caagacaata    1440
agtgttccat atccgtgttt acttaaggtg acgtcaatat ttgtgtgaca gtgcaatgta    1500
ataaaaatat gttaactgtt cactggtttt tattgctttt tgggcgggga ctcaggtata    1560
taagtagaag cagacctgtg tggttagctc ataggagctg gctttcatcc atggaggttt    1620
gggccatttt ggaagacctt aggaagacta ggcaactgtt agagaacgct tcggacggag    1680
tctccggttt ttggagattc tggttcgcta gtgaattagc tagggtagtt tttaggataa    1740
aacaggacta taaacaagaa tttgaaaagt tgttggtaga ttgcccagga ctttttgaag    1800
ctcttaattt gggccatcag gttcacttta aagaaaaagt tttatcagtt ttagactttt    1860
caacccccagg tagaactgct gctgctgtgg ctttctttac ttttatatta gataaatgga    1920
tcccgcagac tcatttcagc aggggatacg ttttggattt catagccaca gcattgtgga    1980
gaacatggaa ggttcgcaag atgaggacaa tcttaggtta ctggccagtg cagcctttgg    2040
gtgtagcggg aatcctgagg catccaccgg tcatgccagc ggttctggag gaggaacagc    2100
aagaggacaa cccgagagcc ggcctggacc ctccagtgga ggaggcggag tagctgactt    2160
gtctcctgaa ctgcaacggg tgcttactgg atctacgtcc actggacggg ataggggcgt    2220
```

```
taagagggag agggcatcta gtggtactga tgctagatct gagttggctt taagtttaat    2280
gagtcgcaga cgtcctgaaa ccatttggtg gcatgaggtt cagaaagagg gaagggatga    2340
agtttctgta ttgcaggaga aatattcact ggaacaggtg aaaacatgtt ggttggagcc    2400
tgaggatgat tgggaggtgg ccattaaaaa ttatgccaag atagctttga ggcctgataa    2460
acagtataag attactagac ggattaatat ccggaatgct tgttacatat ctggaaatgg    2520
ggctgaggtg gtaatagata ctcaagacaa ggcagttatt agatgctgca tgatggatat    2580
gtggcctggg gtagtcggta tggaagcagt aacttttgta aatgttaagt ttaggggaga    2640
tggttataat ggaatagtgt ttatggccaa taccaaactt atattgcatg ttgtagctt     2700
tttttggtttc aacaatacct gtgtagatgc ctggggacag gttagtgtac ggggatgtag   2760
tttctatgcg tgttggattg ccacagctgg cagaaccaag agtcaattgt ctctgaagaa    2820
atgcatattt caaagatgta acctgggcat tctgaatgaa ggcgaagcaa gggtccgcca    2880
ctgcgcttct acagatactg gatgttttat tttgattaag ggaaatgcca gcgtaaagca    2940
taacatgatt tgcggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgatga cgaagtgtac catgcatgca ggtgggcgta gaggaatgtt    3120
tatgccttac cagtgtaaca tgaatcatgt gaaagtgttg ttggaaccag atgcctttc     3180
cagaatgagc ctaacaggaa ttttttgacat gaacatgcaa atctggaaga tcctgaggta   3240
tgatgatacg agatcgaggg tacgcgcatg cgaatgcgga ggcaagcatg ccaggttcca    3300
gccggtgtgt gtagatgtga ctgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gtcatgagtg gaaacgcttc ttttaagggg ggagtcttca gcccttatct gacagggcgt    3540
ctcccatcct gggcaggagt tcgtcagaat gttatgggat ctactgtgga tggaagaccc    3600
gtccaacccg ccaattcttc aacgctgacc tatgctactt taagttcttc acctttggac    3660
gcagctgcag ctgccgccgc cgcttctgtt gccgctaaca ctgtgcttgg aatgggttac    3720
tatgaaagca tcatggctaa ttccacttcc tctaataacc cttctaccct gactcaggac    3780
aagttacttg tccttttggc ccagctggag gctttgaccc aacgtctggg tgaactttct    3840
cagcaggtgg tcgagttgcg agtacaaact gagtctgctg tcggcacggc aaagtctaaa    3900
taaaaaaatc ccagaatcaa tgaataaata acaagcttg ttgttgattt aaaatcaagt     3960
gtttttattt catttttcgc gcacggtatg ccctagacca ccgatctcta tcattgagaa    4020
ctcggtggat ttttccagg atcctataga ggtgggattt aatgtttaga tacatgggca    4080
ttaggccgtc tttggggtgg agatagctcc attgaaggga ttcatgctcc ggggtagtgt    4140
tgtaaatcac ccagtcataa caaggtcgca gtgcatggtg ttgcacaata tcttttagaa    4200
gtaggctgat tgccacagat aagcccttgg tgtaggtgtt tacaaaccgg ttgagctggg    4260
atgggtgcat tcggggtgaa attatgtgca ttttggattg gattttttaag ttggcaatat   4320
tgccgccaag atcccgtctt gggttcatgt tatgaaggac caccaagacg gtgtatccgg    4380
tacatttagg aaatttatcg tgcagcttgg atggaaaagc gtggaaaaat tggagacac     4440
ccttgtgtcc tccaagattt tccatgcact catccatgat aatagcaatg gggccgtggg    4500
cagcggcgcg ggcaaacacg ttccgtgggt ctgacacatc atagttatgt tcctgagtta    4560
```

```
aatcatcata agccatttta atgaatttgg ggcggagagt accagattgg ggtatgaatg    4620
ttccttcggg ccccggagca tagttcccct cacagatttg catttcccaa gctttcagtt    4680
ccgagggtgg aatcatgtcc acctgggggg ctatgaaaaa caccgtttct ggggcggggg    4740
tgattaattg tgatgatagc aaatttctga gcaattgaga tttgccacat ccggtggggc    4800
cataaatgat tccgattacg ggttgcaggt ggtagtttag ggaacggcaa ctgccgtctt    4860
ctcgaagcaa gggggccacc tcgttcatca tttcccttac atgcatattt tcccgcacca    4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
gtctgttcca cagttcagtg atgtgttcta tggcatctcg atccagcaga cctcctcgtt    5100
tcgcgggttt ggacggctcc tggaataggg tatgagacga tgggcgtcca gcgctgccag    5160
ggttcggtcc ttccagggtc tcagtgttcg agtcagggtt gtttccgtca cagtgaaggg    5220
gtgtgcgcct gcttgggcgc ttgccagggt gcgcttcaga ctcatcctgc tggtcgaaaa    5280
cttctgtcgc ttggcgccct gtatgtcggc caagtagcag tttaccatga gttcgtagtt    5340
gagcgcctcg gctgcgtggc ctttggcgcg gagcttacct ttggaagttt tcttgcatac    5400
cgggcagtat aggcatttca gcgcatacaa cttgggcgca aggaaaacgg attctgggga    5460
gtatgcatct gcgccgcagg aggcgcaaac agtttcacat tccaccagcc aggttaaatc    5520
cggttcattg gggtcaaaaa caagttttcc gccatatttt ttgatgcgtt cttacccttt    5580
ggtctccatg agttcgtgtc ctcgttgagt gacaaacagg ctgtccgtgt ccccgtagac    5640
tgattttaca ggcctcttct ccagtggagt gcctcggtct tcttcgtaca ggaactctga    5700
ccactctgat acaaaggcgc gcgtccaggc cagcacaaag gaggctatgt gggaggggta    5760
gcgatcgttg tcaaccaggg ggtccacctt ttccaaagta tgcaaacaca tgtcaccctc    5820
ttcaacatcc aggaatgtga ttggcttgta ggtgtatttc acgtgacctg ggtcccccgc    5880
tgggggggta taaaagggg cggttctttg ctcttcctca ctgtcttccg gatcgctgtc    5940
caggaacgtc agctgttggg gtaggtattc cctctcgaag gcgggcatga cctctgcact    6000
caggttgtca gtttctaaga acgaggagga tttgatattg acagtgccgg ttgagatgcc    6060
tttcatgagg ttttcgtcca tctggtcaga aaacacaatt ttttttattgt caagtttggt    6120 ggcaaatgat ccatacaggg cgttggataa aagtttggca atggatcgca tggtttggtt    6180
cttttccttg tccgcgcgct ctttggcggc gatgttgagt tggacatact cgcgtgccag    6240
gcacttccat tcggggaaga tagttgttaa ttcatctggc acgattctca cttgccaccc    6300
tcgattatgc aaggtaatta aatccacact ggtggccacc tcgcctcgaa ggggttcatt    6360
ggtccaacag agcctacctc ctttcctaga acagaaaggg ggaagtgggt ctagcataag    6420
ttcatcggga gggtctgcat ccatggtaaa gattcccgga agtaaatcct tatcaaaata    6480
gctgatggga gtgggtcat ctaaggccat ttgccattct cgagctgcca gtgcgcgctc    6540
atatgggtta aggggactgc cccatggcat gggatgggtg agtgcagagg catacatgcc    6600
acagatgtca tagacgtaga tgggatcctc aaagatgcct atgtaggttg gatagcatcg    6660
cccccctctg atacttgctc gcacatagtc atatagttca tgtgatggcg ctagcagccc    6720
cggacccaag ttggtgcgat tgggttttc tgttctgtag acgatctggc gaaagatggc    6780
gtgagaattg gaagagatgg tgggtctttg aaaaatgttg aaatgggcat gaggtagacc    6840
tacagagtct ctgacaaagt gggcataaga ttccttgaagc ttggttacca gttcggcggt    6900
gacaagtacg tctagggcgc agtagtcaag tgtttcttga atgatgtcat aacctggttg    6960
```

```
gtttttcttt tcccacagtt cgcggttgag aaggtattct tcgcgatcct tccagtactc    7020
ttctagcgga aacccgtctt tgtctgcacg gtaagatcct agcatgtaga actgattaac    7080
tgccttgtaa gggcagcagc ccttctctac gggtagagag tatgcttgag cagcttttcg    7140
tagcgaagcg tgagtaaggg caaaggtgtc tctgaccatg actttgagga attggtattt    7200
gaagtcgatg tcgtcacagg ctccctgttc ccagagttgg aagtctaccc gtttcttgta    7260
ggcggggttg ggcaaagcga aagtaacatc attgaagaga atcttgccgg ccctgggcat    7320
gaaattgcga gtgatgcgaa aaggctgtgg tacttccgct cggttattga taacctgggc    7380
agctaggacg atctcgtcga aaccgttgat gttgtgtcct acgatgtata attctatgaa    7440
acgcggcgtg cctctgacgt gaggtagctt actgagctca tcaaaggtta ggtctgtggg    7500
gtcagataag gcgtagtgtt cgagagccca ttcgtgcagg tgaggattcg ctttaaggaa    7560
ggaggaccag aggtccactg ccagtgctgt ttgtaactgg tcccggtact gacgaaaatg    7620
ccgtccgact gccattttt ctggggtgac gcaatagaag gtttgggggt cctgccgcca    7680
gcgatcccac ttgagtttta tggcgaggtc ataggcgatg ttgacgagcc gctggtctcc    7740
agagagtttc atgaccagca tgaaggggat tagctgcttg ccaaaggacc ccatccaggt    7800
gtaggtttcc acatcgtagg tgagaaagag cctttctgtg cgaggatgag agccaatcgg    7860
gaagaactgg atctcctgcc accagttgga ggaatggctg ttgatgtgat ggaagtagaa    7920
ctccctgcga cgcgccgagc attcatgctt gtgcttgtac agacggccgc agtagtcgca    7980 gcgttcacg ggttgtatct cgtgaatgag ttgtacctgg cttcccttga cgagaaattt    8040
cagtgggaag ccgaggcctg gcgattgtat ctcgtgcttt actatgttgt ctgcatcggc    8100
ctgttcatct tctgtctcga tggtggtcat gctgacgagc cctcgcggga ggcaagtcca    8160
gacctcggcg cggcagggc ggagctcgag gacgagagcg cgcaggctgg agctgtccag    8220
ggtcctgaga cgctgcggac tcaggttagt aggcagtgtc aggagattaa cttgcatgat    8280
cttttggagg gcgtgcggga ggttcagata gtacttgatc tcaacgggtc cgttggtgga    8340
gatgtcgatg gcttgcaggg ttccgtgtcc cttgggcgct accaccgtgc ccttgttttt    8400
cattttggac ggcggtggct ctgttgcttc ttgcatgttt agaagcggtg tcgagggcgc    8460
gcaccgggcg gcaggggcgg ctcgggaccc ggcggcatgg ctggcagtgg tacgtcggcg    8520
ccgcgcgcgt gtaggttctg gtactgcgcc ctgagaagac tcgcatgcgc gacgacgcgg    8580
cggttgacat cctggatctg acgcctctgg gtgaaagcta ccggccccgt gagcttgaac    8640
ctgaaagaga gttcaacaga atcaatctcg gtatcgttga cggcggcttg cctaaggatt    8700
tcttgcacgt caccagagtt gtcctggtag gcgatctccg ccatgaactg ctcgatctct    8760
tcctcttgaa gatctccgcg gcccgctctc tcgacggtgg ccgcgaggtc gttggagatg    8820
cgcccaatga gttgagagaa tgcattcatg cccgcctcgt tccagacgcg gctgtagacc    8880
acggccccca cgggatctct cgcgcgcatg accacctggg cgaggttgag ctccacgtgg    8940
cgggtgaaga ccgcatagtt gcataggcgc tggaaaaggt agttgagtgt ggtggcgatg    9000
tgctcggtga cgaagaaata catgatccat cgtctcagcg gcatctcgct gacatcgccc    9060
agagcttcca agcgctccat ggcctcgtag aagtccacgc caaaattaaa aaactgggag    9120
tttcgcgcgg acacggtcaa ctcctcttcc agaagacgga taagttcggc gatggtggtg    9180
cgcacctcgc gctcgaaagc ccctgggatt tcttcctcaa tcttcttcttc ttccactaac    9240 atctcttcct cttcaggtgg ggctgcagga ggaggggaa cgcggcgacg ccggcggcgc    9300
```

```
acgggcagac ggtcgatgaa tctttcaatg acctctccgc ggcggcggcg catggtttca    9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcgggaa    9660
ggtgagacga tgctgctggt gatgaaatta aagtaggcag ttctaagacg gcggatggtg    9720
gcgaggagca ccaggtcttt gggtccggct tgctggatac gcaggcgatt ggccattccc    9780
caagcattat cctgacatct agcaagatct ttgtagtagt cttgcatgag ccgttctacg    9840
ggcacttctt cctcacccgt tctgccatgc atacgtgtga gtccaaatcc gcgcattggt    9900
tgtaccagtg ccaagtcagc tacgactctt tcggcgagga tggcttgctg tacttgggta    9960
agggtggctt gaaagtcatc aaaatccaca aagcggtggt aagctcctgt attaatggtg   10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccaggggc gaggtcttcc aacataaggc ggtgatagcc gtagatgtac   10260
ctggacatcc aggtgattcc tgcggcggta gtagaagccc gaggaaactc gcgtacgcgg   10320
ttccaaatgt tgcgtagcgg catgaagtag ttcattgtag gcacggtttg accagtgagg   10380
cgcgcgcagt cattgatgct ctatagacac ggagaaaatg aaagcgttca gcgactcgac   10440
tccgtagcct ggaggaacgt gaacgggttg ggtcgcggtg taccccggtt cgagacttgt   10500
actcgagccg gccggagccg cggctaacgt ggtattggca ctcccgtctc gacccagcct   10560
acaaaaatcc aggatacgga atcgagtcgt tttgctggtt tccgaatggc agggaagtga   10620
gtcctatttt ttttttttgc cgctcagatg catcccgtgc tgcgacagat gcgccccaa    10680
caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt caactgaaa    10860
aaagattctc gcgaggcgta tgtgccccaa cagaacctat ttagagacag aagcggcgag   10920
gagccggagg agatgcgagc ttcccgcttt aacgcgggtc gtgagctgcg tcacggtttg   10980
gaccgaagac gagtgttgcg ggacgaggat ttcgaagttg atgaaatgac agggatcagt   11040
cctgccaggg cacacgtggc tgcagccaac cttgtatcgg cttacgagca gacagtaaag   11100
gaagagcgta acttccaaaa gtcttttaat aatcatgtgc gaaccctgat tgcccgcgaa   11160
gaagttaccc ttggtttgat gcatttgtgg gatttgatgg aagctatcat tcagaaccct   11220
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg ggaaaatatt acgctcgcaa aatctacaag   11460
actccatacg ttcccataga caaggaggtg aagatagatg ggttctacat gcgcatgacg   11520
ctcaaggtct tgaccctgag cgatgatctt ggggtgtatc gcaatgacag aatgcatcgc   11580
gcggttagcg ccagcaggag gcgcgagtta agcgacaggg aactgatgca cagttttcaa   11640
agagctctga ctggagctgg aaccgagggt gagaattact tcgacatggg agctgacttg   11700
```

```
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940
catggcgttg acgactcgca accccgaagc ctttagacag caaccccagg ccaaccgtct   12000
atcggccatc atggaagctg tagtgccttc ccgctctaat cccactcatg agaaggtcct   12060
ggccatcgtg aacgcgttgg tggagaacaa agctattcgt ccagatgagg ccggactggt   12120
atacaacgct ctcttagaac gcgtggctcg ctacaacagt agcaatgtgc aaaccaattt   12180
ggaccgtatg ataacagatg tacgcgaagc cgtgtctcag cgcgaaaggt tccagcgtga   12240
tgccaacctg ggttcgctgg tggcgttaaa tgctttcttg agtactcagc ctgctaatgt   12300
gccgcgtggt caacaggatt atactaactt tttaagtgct ttgagactga tggtatcaga   12360
agtacctcag agcgaagtgt atcagtccgg tcctgattac ttctttcaga ctagcagaca   12420
gggcttgcag acggtaaatc tgagccaagc ttttaaaaac cttaaaggtt tgtggggagt   12480
gcatgccccg gtaggagaaa gagcaaccgt gtctagcttg ttaactccga actcccgcct   12540
attattactg ttggtagctc cttttaccga cagcggtagc atcgaccgta attcctattt   12600
gggttaccta ctaaacctgt atcgcgaagc catagggcaa agtcaggtgg acgagcagac   12660
ctatcaagaa attacccaag tcagtcgcgc tttgggacag gaagacactg gcagtttgga   12720
agccactctg aacttcttgc ttaccaatcg gtctcaaaag atccctcctc aatatgctct   12780
tactgcggag gaggagagga tccttagata tgtgcagcag agcgtgggat tgtttctgat   12840
gcaagagggg gcaactccga ctgcagcact ggacatgaca gcgcgaaata tggagcccag   12900
catgtatgcc agtaaccgac cttcattaa caaactgctg gactacttgc acagagctgc   12960
cgctatgaac tctgattatt tcaccaatgc catcttaaac ccgcactggc tgcccccacc   13020
tggtttctac acgggcgaat atgacatgcc cgaccctaat gacggatttc tgtgggacga   13080
cgtggacagc gatgtttttt cacctctttc tgatcatcgc acgtggaaaa aggaaggcgg   13140
cgatagaatg cattcttctg catcgctgtc cggggtcatg ggtgctaccg cggctgagcc   13200
cgagtctgca gtcctttttc ctagtctacc cttttctcta cacagtgtac gtagcagcga   13260
agtgggtaga ataagtcgcc cgagtttaat gggcgaagag gagtatctaa cgattcctt   13320 gctcagaccg gcaagagaaa aaaatttccc aaacaatgga atagaaagtt tggtggataa   13380
aatgagtaga tggaagactt atgctcagga tcacagagac gagcctggga tcatgggat   13440 tacaagtaga gcgagccgta gacgccagcg ccatgacaga cagaggggtc ttgtgtggga   13500
cgatgaggat tcgccgatg atagcagcgt gctggacttg ggtgggagag gaaggggcaa   13560
cccgtttgct catttgcgcc ctcgcttggg tggtatgttg taaaaaaaaa taaaaaaaaa   13620
actcaccaag gccatggcga cgagcgtacg ttcgttcttc tttattatct gtgtctagta   13680
taatgaggcg agtcgtgcta ggcggagcgg tggtgtatcc ggagggtcct cctccttcgt   13740
acgagagcgt gatgcagcag cagcaggcga cggcggtgat gcaatcccca ctggaggctc   13800
cctttgtgcc tccgcgatac ctggcaccta cggagggcag aaacagcatt cgttattcgg   13860
aactggcacc tcagtacgat accaccaggt tgtatctggt ggacaacaag tcggcggaca   13920
ttgcttctct gaactatcag aatgaccaca gcaacttctt gaccacggtg gtgcaaaaca   13980
atgactttac ccctacggaa gccagcaccc agaccattaa ctttgatgaa cgatcgcggt   14040
```

```
ggggcggtca gctaaagacc atcatgcata ctaacatgcc aaacgtgaac gagtatatgt    14100
ttagtaacaa gttcaaagcg cgtgtgatgg tgtccagaaa acctcccgac ggtgctgcag    14160
ttggggatac ttatgatcac aagcaggata ttttgaaata tgagtggttc gagtttactt    14220
tgccagaagg caacttttca gttactatga ctattgattt tgatgaacaat gccatcatag    14280 ataattactt gaaagtgggt agacagaatg gagtgcttga aagtgacatt ggtgttaagt    14340
tcgacaccag gaacttcaag ctgggatggg atcccgaaac caagttgatc atgcctggag    14400
tgtatacgta tgaagccttc catcctgaca ttgtcttact gcctggctgc ggagtggatt    14460
ttaccgagag tcgtttgagc aaccttcttg gtatcagaaa aaaacagcca tttcaagagg    14520
gttttaagat tttgtatgaa gatttagaag gtggtaatat tccggccctc ttggatgtag    14580
atgcctatga gaacagtaag aaagaacaaa aagccaaaat agaagctgct acagctgctg    14640
cagaagctaa ggcaaacata gttgccagcg actctacaag ggttgctaac gctggagagg    14700
tcagaggaga caattttgcg ccaacacctg ttccgactgc agaatcatta ttggccgatg    14760
tgtctgaagg aacggacgtg aaactcacta ttcaacctgt agaaaaagat agtaagaata    14820
gaagctataa tgtgttggaa gacaaaatca acacagccta tcgcagttgg tatctttcgt    14880
acaattatgg cgatcccgaa aaaggagtgc gttcctggac attgctcacc acctcagatg    14940
tcacctgcgg agcagagcag gtctactggt cgcttccaga catgatgaag gatcctgtca    15000 cttttccgctc cactagacaa gtcagtaact accctgtggt gggtgcagag cttatgcccg    15060
tcttctcaaa gagcttctac aacgaacaag ctgtgtactc ccagcagctc cgccagtcca    15120
cctcgcttac gcacgtcttc aaccgctttc ctgagaacca gattttaatc cgtccgccgg    15180
cgcccaccat taccaccgtc agtgaaaacg ttcctgctct cacagatcac gggaccctgc    15240
cgttgcgcag cagtatccgg ggagtccaac gtgtgaccgt tactgacgcc agacgccgca    15300
cctgtcccta cgtgtacaag gcactgggca tagtcgcacc gcgcgtcctt tcaagccgca    15360
ctttctaaaa aaaaaaaaaa tgtccattct tatctcgccc agtaataaca ccggttgggg    15420
tctgcgcgct ccaagcaaga tgtacggagg cgcacgcaaa cgttctaccc aacatcctgt    15480
ccgtgttcgc ggacatttc gcgctccatg gggcgccctc aagggccgca ctcgcgttcg    15540
aaccaccgtc gatgatgtaa tcgatcaggt ggttgccgac gcccgtaatt atactcctac    15600
tgcgcctaca tctactgtgg atgcagttat tgacagtgta gtggctgacg ctcgcaacta    15660
tgctcgacgt aagagccggc gaaggcgcat tgccagacgc caccgagcta ccactgccat    15720
gcgagccgca agagctctgc tacgaagagc tagacgcgtg gggcgaagag ccatgcttag    15780
ggcggccaga cgtgcagctt cgggcgccag cgccggcagg tcccgcaggc aagcagccgc    15840
tgtcgcagcg gcgactattg ccgacatggc ccaatcgcga agaggcaatg tatactgggt    15900
gcgtgacgct gccaccggtc aacgtgtacc cgtgcgcacc cgtcccctc gcacttagaa    15960 gatactgagc agtctccgat gttgtgtccc agcggcgagg atgtccaagc gcaaatacaa    16020
ggaagaaatg ctgcaggtta tcgcacctga agtctacggc caaccgttga aggatgaaaa    16080 aaaacccgc aaaatcaagc gggttaaaaa ggacaaaaaa gaagaggaag atggcgatga    16140
tgggctggcg gagtttgtgc gcgagtttgc cccacggcga cgcgtgcaat ggcgtgggcg    16200
caaagttcga catgtgttga gacctggaac ttcggtggtc tttacacccg gcgagcgttc    16260
aagcgctact tttaagcgtt cctatgatga ggtgtacggg gatgatgata ttcttgagca    16320
ggcggctgac cgattaggcg agtttgctta ggcaagcgt agtagaataa cttccaagga    16380
tgagacagtg tcgatacct tggatcatgg aaatcccacc cctagtctta aaccggtcac    16440
```

```
tttgcagcaa gtgttacccg taactccgcg aacaggtgtt aaacgcgaag gtgaagattt   16500
gtatcccact atgcaactga tggtacccaa acgccagaag ttggaggacg ttttggagaa   16560
agtaaaagtg gatccagata ttcaacctga ggttaaagtg agacccatta agcaggtagc   16620
gcctggtctg ggggtacaaa ctgtagacat taagattccc actgaaagta tggaagtgca   16680
aactgaaccc gcaaagccta ctgccacctc cactgaagtg caaacggatc catggatgcc   16740
catgcctatt acaactgacg ccgccggtcc cactcgaaga tcccgacgaa agtacgtcc   16800 agcaagtctg ttgatgccca attatgttgt acacccatct attattccta ctcctggtta   16860
ccgaggcact cgctactatc gcagccgaaa cagtacctcc cgccgtcgcc gcaagacacc   16920
tgcaaatcgc agtcgtcgcc gtagacgcac aagcaaaccg actcccggcg ccctggtgcg   16980
gcaagtgtac cgcaatggta gtgcggaacc tttgacactg ccgcgtgcgc gttaccatcc   17040
gagtatcatc acttaatcaa tgttgccgct gcctccttgc agatatggcc ctcacttgtc   17100
gccttcgcgt tccatcact ggttaccgag gaagaaactc gcgccgtaga agagggatgt    17160
tgggacgcgg aatgcgacgc tacaggcgac ggcgtgctat ccgcaagcaa ttgcggggtg   17220
gttttttacc agccttaatt ccaattatcg ctgctgcaat tggcgcgata ccaggcatag   17280
cttccgtggc ggttcaggcc tcgcaacgac attgacattg aaaaaaacg tataaataaa    17340 aaaaaaaaaa tacaatggac tctgacactc ctggtcctgt gactatgttt tcttagagat   17400
ggaagacatc aattttcat ccttggctcc gcgacacggc acgaagccgt acatgggcac    17460
ctggagcgac atcggcacga gccaactgaa cggggcgcc ttcaattgga gcagtatctg    17520
gagcgggctt aaaaattttg gctcaaccat aaaaacatac gggaacaaag cttggaacag   17580
cagtacagga caggcgctta gaaataaact taaagaccag aacttccaac aaaaagtagt   17640
cgatgggata gcttccggca tcaatggagt ggtagatttg gctaaccagg ctgtgcagaa   17700
aaagataaac agtcgtttgg acccgccgcc agcaaccca ggtgaaatgc aagtggagga    17760
agaaattcct ccgccagaaa aacgaggcga caagcgtccg cgtcccgatt tggaagagac   17820
gctggtgacg cgcgtagatg aaccgccttc ttatgaggaa gcaacgaagc ttggaatgcc   17880
caccactaga ccgatagccc caatggccac cggggtgatg aaaccttctc agttgcatcg   17940
acccgtcacc ttggatttgc cccctccccc tgctgctact gctgtacccg cttctaagcc   18000
tgtcgctgcc ccgaaaccag tcgccgtagc caggtcacgt cccgggggcg ctcctcgtcc   18060
aaatgcgcac tggcaaaata ctctgaacag catcgtgggt ctaggcgtgc aaagtgtaaa   18120
acgccgtcgc tgcttttaat taaatatgga gtagcgctta acttgcctat ctgtgtatat   18180
gtgtcattac acgccgtcac agcagcagag gaaaaaagga agaggtcgtg cgtcgacgct   18240
gagttacttt caagatggcc accccatcga tgctgcccca atgggcatac atgcacatcg   18300
ccggacagga tgcttcggag tacctgagtc cgggtctggt gcagttcgcc cgcgccacag   18360
acacctactt caatctggga aataagttta gaaatcccac cgtagcgccg acccacgatg   18420
tgaccaccga ccgtagccag cggctcatgt tgcgcttcgt gcccgttgac cgggaggaca   18480
atacatactc ttacaaagtg cggtacaccc tggccgtggg cgacaacaga gtgctggata   18540
tggccagcac gttcttgac attaggggtg tgttggacag aggtcccagt ttcaaaccct    18600
attctggtac ggcttacaac tccctggctc ctaaaggcgc tccaaataca tctcagtgga   18660
ttgcagaagg tgtaaaaaat acaactggtg aggaacacgt aacagaagag gaaaccaata   18720
ctactactta cacttttggc aatgctcctg taaaagctga agctgaaatt acaaaagaag   18780
```

```
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agttttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg ggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacacccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc attttttcaga aacttccagc  20640 ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggccccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
```

```
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt caataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
aggggatca gtatcatctt ggcctgatcc tgtctgattc ctggatacac ggctctcatg  22320
aaagcatcat attgcttgaa agcctgctgg gctttactac cctcggtata aacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct cttctcttct cgctgtcttg actgatgtct  23100
tgcatgggga tatgtttggt cttccttggc ttcttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg ggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
```

```
ttccaccgcc cagtcctgcc accacctcta ccctagaaga taaggaggtc gacgcatctc   23580
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct catagggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tcccccaaa cgtcagccaa    23940
acggcacctg cgagccaaat cctcgcttaa acttttatcc agcttttgct gtgccagaag   24000
tactggctac ctatcacatc ttttttaaaa atcaaaaaat tccagtctcc tgccgcgcta   24060
atcgcacccg cgccgatgcc ctactcaatc tgggacctgg ttcacgctta cctgatatag   24120
cttccttgga agaggttcca aagatcttcg agggtctggg caataatgag actcgggccg   24180
caaatgctct gcaaaaggga gaaaatggca tggatgagca tcacagcgtt ctggtggaat   24240
tggaaggcga taatgccaga ctcgcagtac tcaagcgaag catcgaggtc acacacttcg   24300
catatcccgc tgtcaacctg ccccctaaag tcatgacggc ggtcatggac cagttactca   24360
ttaagcgcgc aagtccccctt tcagaagaca tgcatgaccc agatgcctgt gatgagggta   24420
aaccagtggt cagtgatgag cagctaaccc gatggctggg caccgactct cccagggatt   24480
tggaagagcg tcgcaagctt atgatggccg tggtgctggt taccgtagaa ctagagtgtc   24540
tccgacgttt cttaccgat tcagaaacct tgcgcaaact cgaagagaat ctgcactaca    24600
cttttagaca cggctttgtg cggcaggcat gcaagatatc taacgtggaa ctcaccaacc   24660
tggtttccta catgggtatt ctgcatgaga atcgcctagg acaaagcgtg ctgcacagca   24720
ccctgaaggg ggaagcccgc cgtgattaca tccgcgattg tgtctatctg tacctgtgcc   24780
acacgtggca aaccggcatg ggtgtatggc agcaatgttt agaagaacag aacttgaaag   24840
agcttgacaa gctcttacag aaatctctta aggttctgtg gacagggttc gacgagcgca   24900
ccgtcgcttc cgacctggca gacctcatct tcccagagcg tctcagggtt actttgcgaa   24960
acggattgcc tgacttatg agccagagca tgcttaacaa ttttcgctct ttcatcctgg    25020
aacgctccgg tatcctgccc gccacctgct gcgcactgcc ctccgacttt gtgcctctca   25080
cctaccgcga gtgcccccg ccgctatgga gtcactgcta cctgttccgt ctggccaact   25140
atctctccta ccactcggat gtgatcgagg atgtgagcgg agacggcttg ctggagtgtc   25200
actgccgctg caatctgtgc acgccccacc ggtccctagc ttgcaacccc cagttgatga   25260
gcgaaaccca gataataggc acctttgaat tgcaaggccc cagcagccaa ggcgatgggt   25320
cttctcctgg gcaaagttta aaactgaccc cgggactgtg gacctccgcc tacttgcgca   25380
agtttgctcc ggaagattac caccctatg aaatcaagtt ctatgaggac caatcacagc    25440
ctccaaaggc cgaactttcg gcctgcgtca tcacccaggg ggcaattctg cccaattgc    25500
aagccatcca aaaatcccgc caagaatttc tactgaaaaa gggtaagggg gtctaccttg   25560
accccccagac cggcgaggaa ctcaacacaa ggttccctca ggatgtccca acgacgagaa   25620
aacaagaagt tgaaggtgca gccgccgccc ccagaagata tggaggaaga ttgggacagt   25680
caggcagagg aggcggagga ggacagtctg gaggacagtc tggaggaaga cagtttggag   25740
gaggaaaacg aggaggcaga ggaggtggaa gaagtaaccg ccgacaaaca gttatcctcg   25800
gctgcgagaa caagcaacag cgctaccatc tccgctccga gtcgaggaac ccggcggcgt   25860
cccagcagta gatgggacga gaccggacgc ttcccgaacc caaccagcgc ttccaagacc   25920
```

```
ggtaagaagg atcggcaggg atacaagtcc tggcgggggc ataagaatgc catcatctcc   25980
tgcttgcatg agtgcggggg caacatatcc ttcacgcggc gctacttgct attccaccat   26040
ggggtgaact ttccgcgcaa tgttttgcat tactaccgtc acctccacag cccctactat   26100
agccagcaaa tccggcagt ctcgacagat aaagacagcg gcggcgacct caacagaaa    26160
accagcagcg gcagttagaa aatacacaac aagtgcagca acaggaggat taaagattac   26220
agccaacgag ccagcgcaaa cccgagagtt aagaaatcgg atctttccaa ccctgtatgc   26280
catcttccag cagagtcggg gtcaagagca ggaactgaaa ataaaaaacc gatctctgcg   26340
ttcgctcacc agaagttgtt tgtatcacaa gagcgaagat caacttcagc gcactctcga   26400
ggacgccgag gctctcttca acaagtactg cgcgctgact cttaaagagt aggcagcgac   26460
cgcgcttatt caaaaaaggc gggaattaca tcatcctcga catgagtaaa gaaattccca   26520
cgccttacat gtggagttat caaccccaaa tgggattggc ggcaggcgcc tcccaggact   26580
actccacccg catgaattgg ctcagcgccg ggccttctat gatttctcga gttaatgata   26640
tacgcgccta ccgaaaccaa atactttgg aacagtcagc tcttaccacc acgccccgcc    26700
aacaccttaa tcccagaaat tggcccgccg ccctagtgta ccaggaaagt cccgctccca   26760
ccactgtatt acttcctcga gacgcccagg ccgaagtcca aatgactaat gcaggtgcgc   26820
agttagctgg cggctccacc ctatgtcgtc acaggcctcg gcataatata aaacgcctga   26880
tgatcagagg ccgaggtatc cagctcaacg acgagtcggt gagctctccg cttggtctac   26940
gaccagacgg aatctttcag attgccggct gcgggagatc ttccttcacc cctcgtcagg   27000
ctgttctgac tttggaaagt tcgtcttcgc aaccccgctc gggcggaatc gggaccgttc   27060
aatttgtgga ggagtttact ccctctgtct acttcaaccc cttctccgga tctcctgggc   27120
attacccgga cgagttcata ccgaacttcg acgcgattag cgagtcagtg gacggctacg   27180
attgatgtct ggtgacgcgg ctgagctatc tcggctgcga catctagacc actgccgccg   27240
cttccgctgc tttgcccggg aactcattga gttcatctac ttcgaactcc ccaaggatca   27300
ccctcaaggt ccggcccacg gagtgcggat ttctatcgaa ggcaaaatag actctcgcct   27360
gcaacgaatt ttctcccagc ggcccgtgct gatcgagcga gaccagggaa acaccacggt   27420
ttccatctac tgcatttgta atcaccccgg attgcatgaa agcctttgct gtcttatgtg   27480
tactgagttt aataaaaact gaattaagac tctcctacgg actgccgctt cttcaacccg   27540
gattttacaa ccagaagaac gaaactttc ctgtcgtcca ggactctgtt aacttcacct    27600
ttcctactca caaactagaa gctcaacgac tacaccgctt ttccagaagc attttcccta   27660
ctaatactac tttcaaaacc ggaggtgagc tccaaggtct tcctacagaa aacccttggg   27720
tggaagcggg cttgtagtg ctaggaattc ttgcgggtgg gcttgtgatt attctttgct    27780
acctatacac accttgcttc actttcttag tggtgttgtg gtattggttt aaaaaatggg   27840
gcccatacta gtcttgcttg ttttactttc gcttttggaa ccgggttctg ccaattacga   27900
tccatgtcta gacttcgacc cagaaaactg cacacttact tttgcacccg acacaagccg   27960
catctgtgga gttcatcgcc tctcttacga acttggcccc caacgacaaa aatttacctg   28020
catggtggga atcaacccca tagttatcac ccagcaaagt ggagatacta agggttgcat   28080
tcactgctcc tgcgattcca tcgagtgcac ctacaccctg ctgaagaccc tatgcggcct   28140
aagagacctg ctaccaatga attaaaaaat gattaataaa aaatcactta cttgaaatca   28200
gcaataaggt ctctgttgaa attttctccc agcagcacct cacttccctc ttcccaactc   28260
```

```
tggtattcta aaccccgttc agcggcatac tttctccata ctttaaaggg gatgtcaaat    28320
tttagctcct ctcctgtacc cacaatcttc atgtctttct tcccagatga ccaagagagt    28380
ccggctcagt gactccttca accctgtcta ccctatgaa gatgaaagca cctcccaaca    28440
cccctttata aacccagggt ttatttcccc aaatggcttc acacaaagcc caaacggagt    28500
tcttacttta aaatgtttaa ccccactaac aaccacaggc ggatctctac agctaaaagt    28560
gggagggga cttacagtgg atgacaccaa cggttttttg aaagaaaaca taagtgccac    28620
cacaccactc gttaagactg gtcactctat aggtttacca ctaggagccg gattgggaac    28680
gaatgaaaat aaactttgta tcaaattagg acaaggactt acattcaatt caaacaacat    28740
ttgcattgat gacaatatta acaccttatg gacaggagtc aaccccaccg aagccaactg    28800
tcaaatcatg aactccagtg aatctaatga ttgcaaatta attctaacac tagttaaaac    28860
tggagcacta gtcactgcat tgtttatgt tataggagta tctaacaatt ttaatatgct    28920
aactacacac agaaatataa atttactgc agagctgttt ttcgattcta ctggtaattt    28980
actaactaga ctctcatccc tcaaaactcc acttaatcat aaatcaggac aaaacatggc    29040
tactggtgcc attactaatg ctaaaggttt catgcccagc acgactgcct atcctttcaa    29100
tgataattct agagaaaaag aaaactacat ttacggaact tgttactaca cagctagtga    29160
tcgcactgct tttcccattg acatatctgt catgcttaac cgaagagcaa taaatgacga    29220
gacatcatat tgtattcgta taacttggtc ctggaacaca ggagatgccc cagaggtgca    29280
aacctctgct acaaccctag tcacctcccc atttacctt tactacatca gagaagacga    29340
ctgacaaata aagtttaact tgtttatttg aaaatcaatt cacaaaatcc gagtagttat    29400
tttgcctccc ccttcccatt taacagaata caccaatctc tccccacgca cagctttaaa    29460
catttggata ccattagata tagacatggt tttagattcc acattccaaa cagtttcaga    29520
gcgagccaat ctggggtcag tgatagataa aaatccatcg ggatagtctt ttaaagcgct    29580
ttcacagtcc aactgctgcg gatgcgactc cggagtctgg atcacggtca tctggaagaa    29640
gaacgatggg aatcataatc cgaaaacggt atcggacgat tgtgtctcat caaacccaca    29700
agcagccgct gtctgcgtcg ctccgtgcga ctgctgttta tgggatcagg gtccacagtg    29760
tcctgaagca tgattttaat agcccttaac atcaactttc tggtgcgatg cgcgcagcaa    29820
cgcattctga tttcactcaa atctttgcag taggtacaac acattattac aatattgttt    29880
aataaaccat aattaaaagc gctccagcca aaactcatat ctgatataat cgcccctgca    29940
tgaccatcat accaaagttt aatataaatt aaatgacgtt ccctcaaaaa cacactaccc    30000
acatacatga tctcttttgg catgtgcata ttaacaatct gtctgtacca tggacaacgt    30060
tggttaatca tgcaacccaa tataaccttc cggaaccaca ctgccaacac cgctccccca    30120
gccatgcatt gaagtgaacc ctgctgatta caatgacaat gaagaaccca attctctcga    30180
ccgtgaatca cttgagaatg aaaaatatct atagtggcac aacatagaca taatgcatg    30240
catcttctca taattttaa ctcctcagga tttagaaaca tatcccaggg aataggaagc    30300
tcttgcagaa cagtaaagct ggcagaacaa ggaagaccac gaacacaact tacactatgc    30360
atagtcatag tatcacaatc tggcaacagc gggtggtctt cagtcataga agctcggtt    30420
tcattttcct cacaacgtgg taactgggct ctggtgtaag ggtgatgtct ggcgcatgat    30480
gtcgagcgtg cgcgcaacct tgtcataatg gagttgcttc ctgacattct cgtattttgt    30540
atagcaaaac gcggccctgg cagaacacac tcttcttcgc cttctatcct gccgcttagc    30600
gtgttccgtg tgatagttca agtacaacca cactcttaag ttggtcaaaa gaatgctggc    30660
```

```
ttcagttgta atcaaaactc catcgcatct aatcgttctg aggaaatcat ccacggtagc    30720
atatgcaaat cccaaccaag caatgcaact ggattgtgtt tcaagcagga gaggagaggg    30780
aagagacgga agaaccatgt taattttat tccaaacgat ctcgcagtac ttcaaattgt    30840
agatcgcgca gatggcatct ctcgccccca ctgtgttggt gaaaaagcac agctagatca    30900
aaagaaatgc gattttcaag gtgctcaacg gtggcttcca gcaaagcctc cacgcgcaca    30960
tccaagaaca aagaatacc aaagaagga gcattttcta actcctcaat catcatatta    31020
cattcctgca ccattcccag ataattttca gctttccagc cttgaattat tcgtgtcagt    31080
tcttgtggta aatccaatcc acacattaca aacaggtccc ggagggcgcc ctccaccacc    31140
attcttaaac acaccctcat aatgacaaaa tatcttgctc ctgtgtcacc tgtagcgaat    31200
tgagaatggc aacatcaatt gacatgccct tggctctaag ttcttcttta agttctagtt    31260
gtaaaaactc tctcatatta tcaccaaact gcttagccag aagcccccg ggaacaagag    31320 caggggacgc tacagtgcag tacaagcgca gacctcccca attggctcca gcaaaaacaa    31380
gattggaata agcatattgg gaaccgccag taatatcatc gaagttgctg gaaatataat    31440
caggcagagt ttcttgtaaa aattgaataa agaaaaatt tgccaaaaaa acattcaaaa    31500
cctctgggat gcaaatgcaa taggttaccg cgctgcgctc caacattgtt agttttgaat    31560
tagtctgcaa aaataaaaaa aaaaacaagc gtcatatcat agtagcctga cgaacagatg    31620
gataaatcag tctttccatc acaagacaag ccacagggtc tccagctcga ccctcgtaaa    31680
acctgtcatc atgattaaac aacagcaccg aaagttcctc gcggtgacca gcatgaataa    31740
ttcttgatga agcatacaat ccagacatgt tagcatcagt taacgagaaa aaacagccaa    31800
catagccttt gggtataatt atgcttaatc gtaagtatag caaagccacc cctcgcggat    31860
acaaagtaaa aggcacagga gaataaaaaa tataattatt tctctgctgc tgttcaggca    31920
acgtcgcccc cggtccctct aaatacacat acaaagcctc atcagccatg cttaccaga    31980 caaagtacag cgggcacaca aagcacaagc tctaaagtga ctctccaacc tctccacaat    32040
atatatatac acaagcccta aactgacgta atgggagtaa agtgtaaaaa atcccgccaa    32100
acccaacaca caccccgaaa ctgcgtcacc agggaaaagt acagtttcac ttccgcaatc    32160
ccaacaggcg taacttcctc tttctcacgg tacgtgatat cccactaact tgcaacgtca    32220
ttttcccacg gtcgcaccgc ccctttagc cgttaacccc acagccaatc accacacgat    32280
ccacactttt taaaatcacc tcatttacat attggcacca ttccatctat aaggtatatt    32340
atatagatag a                                                        32351
```

<210> SEQ ID NO 29
<211> LENGTH: 32326
<212> TYPE: DNA
<213> ORGANISM: Artificial Sequence
<220> FEATURE:
<223> OTHER INFORMATION: NG-186 Genome Sequence (EnAd genome with Ad11p E2B region)

<400> SEQUENCE: 29

```
tctatctata taatatacct tatagatgga atggtgccaa tatgtaaatg aggtgatttt      60
aaaaagtgtg gatcgtgtgg tgattggctg tggggttaac ggctaaaagg ggcggtgcga     120
ccgtgggaaa atgacgtttt gtggggggtgg agttttttg caagttgtcg cgggaaatgt     180
gacgcataaa aaggcttttt tctcacggaa ctacttagtt ttcccacggt atttaacagg     240
aaatgaggta gttttgaccg gatgcaagtg aaaattgttg attttcgcgc gaaaactgaa     300
```

| | |
|---|---|
| tgaggaagtg tttttctgaa taatgtggta tttatggcag ggtggagtat tgttcaggg | 360 |
| ccaggtagac tttgacccat tacgtggagg tttcgattac cgtgtttttt acctgaattt | 420 |
| ccgcgtaccg tgtcaaagtc ttctgttttt acgtaggtgt cagctgatcg ctagggtatt | 480 |
| tatacctcag ggtttgtgtc aagaggccac tcttgagtgc cagcgagaag agttttctcc | 540 |
| tctgcgccgg cagtttaata ataaaaaaat gagagatttg cgatttctgc ctcaggaaat | 600 |
| aatctctgct gagactggaa atgaaatatt ggagcttgtg gtgcacgccc tgatgggaga | 660 |
| cgatccggag ccacctgtgc agcttttttga gcctcctacg cttcaggaac tgtatgattt | 720 |
| agaggtagag ggatcggagg attctaatga ggaagctgta aatggctttt ttaccgattc | 780 |
| tatgcttttta gctgctaatg aagggttaga attagatccg cctttggaca cttttgatac | 840 |
| tccaggggta attgtggaaa gcggtacagg tgtaagaaaa ttacctgatt tgagttccgt | 900 |
| ggactgtgat ttgcactgct atgaagacgg gtttcctccg agtgatgagg aggaccatga | 960 |
| aaaggagcag tccatgcaga ctgcagcggg tgagggagtg aaggctgcca atgttggttt | 1020 |
| tcagttggat tgcccggagc ttcctggaca tggctgtaag tcttgtgaat tcacaggaa | 1080 |
| aaatactgga gtaaaggaac tgttatgttc gctttgttat atgagaacgc actgccactt | 1140 |
| tatttacagt aagtgtgttt aagttaaaat ttaaggaat atgctgtttt tcacatgtat | 1200 |
| attgagtgtg agttttgtgc ttcttattat aggtcctgtg tctgatgctg atgaatcacc | 1260 |
| atctcctgat tctactacct cacctcctga gattcaagca cctgttcctg tggacgtgcg | 1320 |
| caagcccatt cctgtgaagc ttaagcctgg gaaacgtcca gcagtggaaa aacttgagga | 1380 |
| cttgttacag ggtggggacg gacctttgga cttgagtaca cggaaacgtc caagacaata | 1440 |
| agtgttccat atccgtgttt acttaaggtg acgtcaatat ttgtgtgaca gtgcaatgta | 1500 |
| ataaaaatat gttaactgtt cactggtttt tattgctttt tgggcgggga ctcaggtata | 1560 |
| taagtagaag cagacctgtg tggttagctc ataggagctg gctttcatcc atggaggttt | 1620 |
| gggccatttt ggaagacctt aggaagacta ggcaactgtt agagaacgct tcggacggag | 1680 |
| tctccggttt ttggagattc tggttcgcta gtgaattagc tagggtagtt tttaggataa | 1740 |
| aacaggacta taaacaagaa tttgaaaagt tgttggtaga ttgcccagga cttttttgaag | 1800 |
| ctcttaattt gggccatcag gttcacttta aagaaaaagt tttatcagtt ttagacttt | 1860 |
| caaccccagg tagaactgct gctgctgtgg cttttcttac ttttatatta gataaatgga | 1920 |
| tcccgcagac tcatttcagc aggggatacg ttttggattt catagccaca gcattgtgga | 1980 |
| gaacatggaa ggttcgcaag atgaggacaa tcttaggtta ctggccagtg cagcctttgg | 2040 |
| gtgtagcggg aatcctgagg catccaccgg tcatgccagc ggttctggag gaggaacagc | 2100 |
| aagaggacaa cccgagagcc ggcctggacc ctccagtgga ggaggcggag tagctgactt | 2160 |
| gtctcctgaa ctgcaacggg tgcttactgg atctacgtcc actggacggg ataggggcgt | 2220 |
| taagagggag agggcatcta gtggtactga tgctagatct gagttggctt taagtttaat | 2280 |
| gagtcgcaga cgtcctgaaa ccatttggtg gcatgaggtt cagaaagagg gaagggatga | 2340 |
| agtttctgta ttgcaggaga aatattcact ggaacaggtg aaaacatgtt ggttggagcc | 2400 |
| tgaggatgat tgggaggtgg ccattaaaaa ttatgccaag atagctttga ggcctgataa | 2460 |
| acagtataag attactagac ggattaatat ccggaatgct tgttacatat ctggaaatgg | 2520 |
| ggctgaggtg gtaatagata ctcaagacaa ggcagttatt agatgctgca tgatggatat | 2580 |
| gtggcctggg gtagtcggta tggaagcagt aacttttgta aatgttaagt ttaggggaga | 2640 |

```
tggttataat ggaatagtgt ttatggccaa taccaaactt atattgcatg gttgtagctt    2700
ttttggtttc aacaatacct gtgtagatgc ctggggacag gttagtgtac ggggatgtag    2760
tttctatgcg tgttggattg ccacagctgg cagaaccaag agtcaattgt ctctgaagaa    2820
atgcatattt caaagatgta acctgggcat tctgatgaa ggcgaagcaa gggtccgcca    2880
ctgcgcttct acagatactg gatgttttat tttgattaag ggaaatgcca gcgtaaagca    2940
taacatgatt tgcggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgatga cgaagtgtac catgcatgca ggtgggcgta gaggaatgtt    3120
tatgccttac cagtgtaaca tgaatcatgt gaaagtgttg ttggaaccag atgccttttc    3180
cagaatgagc ctaacaggaa ttttgacat gaacatgcaa atctggaaga tcctgaggta    3240
tgatgatacg agatcgaggg tacgcgcatg cgaatgcgga ggcaagcatg ccaggttcca    3300
gccggtgtgt gtagatgtga ctgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gttttttctg tcttgcagct    3480
gtcatgagtg gaaacgcttc ttttaagggg ggagtcttca gcccttatct gacagggcgt    3540
ctcccatcct gggcaggagt tcgtcagaat gttatgggat ctactgtgga tggaagaccc    3600
gtccaacccg ccaattcttc aacgctgacc tatgctactt taagttcttc acctttggac    3660
gcagctgcag ctgccgccgc cgcttctgtt gccgctaaca ctgtgcttgg aatgggttac    3720 tatgaagca tcatgctaa ttccacttcc tctaataacc cttctaccct gactcaggac    3780
aagttacttg tccttttggc ccagctggag gctttgaccc aacgtctggg tgaacttctt    3840
cagcaggtgg tcgagttgcg agtacaaact gagtctgctg tcggcacggc aaagtctaaa    3900
taaaaaaatc ccagaatcaa tgaataaata acaagcttg ttgttgattt aaaatcaagt    3960
gtttttattt catttttcgc gcacggtatg ccctagacca ccgatctcta tcattgagaa    4020
ctcggtggat tttttccagg atcctataga ggtgggattg aatgtttaga tacatgggca    4080
ttaggccgtc tttggggtgg agatagctcc attgaaggga ttcatgctcc ggggtagtgt    4140
tgtaaatcac ccagtcataa caaggtcgca gtgcatggtg ttgcacaata tcttttagaa    4200
gtaggctgat tgccacagat aagcccttgg tgtaggtgtt tacaaaccgg ttgagctggg    4260
atgggtgcat tcggggtgaa attatgtgca ttttggattg gattttttaag ttggcaatat    4320 tgccgccaag atcccgtctt gggttcatgt tatgaaggac caccaagacg gtgtatccgg    4380
tacatttagg aaatttatcg tgcagcttgg atggaaaagc gtggaaaaat ttggagacac    4440
ccttgtgtcc tccaagattt tccatgcact catccatgat aatagcaatg gggccgtggg    4500
cagcggcgcg ggcaaacacg ttccgtgggt ctgacacatc atagttatgt tcctgagtta    4560
aatcatcata agccatttta atgaatttgg ggcggagagt accagattgg ggtatgaatg    4620
ttccttcggg ccccggagca tagttcccct cacagatttg catttcccaa gctttcagtt    4680
ccgagggtgg aatcatgtcc acctgggggg ctatgaaaaa caccgtttct ggggcggggg    4740
tgattaattg tgatgatagc aaatttctga gcaattgaga tttgccacat ccggtggggc    4800
cataaatgat tccgattacg ggttgcaggt ggtagtttag ggaacggcaa ctgccgtctt    4860
ctcgaagcaa gggggccacc tcgttcatca tttcccttac atgcatattt tcccgcacca    4920
aatccattag gaggcgctct cctcctagtg atagaagttc ttgtagtgag gaaaagtttt    4980
tcagcggttt cagaccgtca gccatgggca ttttggagag agtttgctgc aaaagttcta    5040
```

```
gtctgttcca cagttcagtg atgtgttcta tggcatctcg atccagcaga cctcctcgtt     5100
tcgcgggttt ggacggctcc tggaataggg tatgagacga tgggcgtcca gcgctgccag     5160
ggttcggtcc ttccagggtc tcagtgttcg agtcagggtt gtttccgtca cagtgaaggg     5220
gtgtgcgcct gcttgggcgc ttgccagggt gcgcttcaga ctcatcctgc tggtcgaaaa     5280
cttctgtcgc ttggcgccct gtatgtcggc caagtagcag tttaccatga gttcgtagtt     5340
gagcgcctcg gctgcgtggc ctttggcgcg agcttacct ttggaagttt tcttgcatac      5400
cgggcagtat aggcatttca gcgcatacaa cttgggcgca aggaaaacgg attctgggga     5460
gtatgcatct gcgccgcagg aggcgcaaac agtttcacat tccaccagcc aggttaaatc     5520
cggttcattg gggtcaaaaa caagttttcc gccatatttt ttgatgcgtt tcttacctt     5580
ggtctccatg agttcgtgtc ctcgttgagt gacaaacagg ctgtccgtgt ccccgtagac     5640
tgattttaca ggcctcttct ccagtggagt gcctcggtct tcttcgtaca ggaactctga     5700
ccactctgat acaaaggcgc gcgtccagcc cagcacaaag gaggctatgt gggaggggta     5760
gcgatcgttg tcaaccaggg ggtccacctt ttccaaagta tgcaaacaca tgtcaccctc     5820
ttcaacatcc aggaatgtga ttggcttgta ggtgtatttc acgtgacctg ggtccccgc     5880
tgggggggta taaaaggggg cggttctttg ctcttcctca ctgtcttccg gatcgctgtc     5940
caggaacgtc agctgttggg gtaggtattc cctctcgaag gcgggcatga cctctgcact     6000
caggttgtca gtttctaaga acgaggagga tttgatattg acagtgccgg ttgagatgcc     6060
tttcatgagg ttttcgtcca tttggtcaga aaacacaatt tttttattgt caagtttggt     6120
ggcaaatgat ccatacaggg cgttggataa aagtttggca atggatcgca tggtttggtt     6180
cttttccttg tccgcgcgct ctttggcggc gatgttgagt tggacatact cgcgtgccag     6240
gcacttccat tcggggaaga tagttgttaa ttcatctggc acgattctca cttgccaccc     6300
tcgattatgc aaggtaatta aatccacact ggtggccacc tcgcctcgaa ggggttcatt     6360
ggtccaacag agcctacctc ctttcctaga acagaaaggg ggaagtgggt ctagcataag     6420
ttcatcggga gggtctgcat ccatggtaaa gattcccgga agtaaatcct tatcaaaata     6480
gctgatggga gtggggtcat ctaaggccat ttgccattct cgagctgcca gtgcgcgctc     6540
atatgggtta aggggactgc cccatggcat gggatgggtg agtgcagagg catacatgcc     6600
acagatgtca tagacgtaga tgggatcctc aaagatgcct atgtaggttg gatagcatcg     6660
cccccctctg atacttgctc gcacatagtc atatagttca tgtgatggcg ctagcagccc     6720
cggacccaag ttggtgcgat tgggtttttc tgttctgtag acgatctggc gaaagatggc     6780
gtgagaattg aagagatgg tgggtctttg aaaaatgttg aaatgggcat gaggtagacc      6840
tacagagtct ctgacaaagt gggcataaga ttcttgaagc ttggttacca gttcggcggt     6900
gacaagtacg tctagggcgc agtagtcaag tgtttcttga atgatgtcat aacctggttg     6960
gttttctttt tcccacagtt cgcggttgag aaggtattct tcgcgatcct tccagtactc     7020
ttctagcgga aacccgtctt tgtctgcacg gtaagatcct agcatgtaga actgattaac     7080
tgccttgtaa gggcagcagc ccttctctac gggtagagag tatgcttgag cagcttttcg     7140
tagcgaagcg tgagtaaggg caaggtgtc tctgaccatg actttgagaa attggtattt      7200
gaagtcgatg tcgtcacagg ctccctgttc ccagagttgg aagtctaccc gtttcttgta     7260
ggcggggttg gcaaagcga aagtaacatc attgaagaga atcttaccgg ctctgggcat      7320
aaaattgcga gtgatgcgaa aaggctgtgg tacttccgct cgattgttga tcacctgggc     7380
```

```
agctaggacg atctcgtcga aaccgttgat gttgtgtcct acgatgtata attctatgaa    7440
acgcggcgtg cctctgacgt gaggtagctt actgagctca tcaaaggtta ggtctgtggg    7500
gtcagataag gcgtagtgtt cgagagccca ttcgtgcagg tgaggatttg catgtaggaa    7560
tgatgaccaa agatctaccg ccagtgctgt ttgtaactgg tcccgatact gacgaaaatg    7620
ccggccaatt gccatttttt ctggagtgac acagtagaag gttctggggt cttgttgcca    7680
tcgatcccac ttgagtttaa tggctagatc gtgggccatg ttgacgagac gctcttctcc    7740
tgagagtttc atgaccagca tgaaaggaac tagttgtttg ccaaaggatc ccatccaggt    7800
gtaagtttcc acatcgtagg tcaggaagag tctttctgtg cgaggatgag agccgatcgg    7860
gaagaactgg atttcctgcc accagttgga ggattggctg ttgatgtgat ggaagtagaa    7920
gtttctgcgg cgcgccgagc attcgtgttt gtgcttgtac agacggccgc agtagtcgca    7980
gcgttgcacg ggttgtatct cgtgaatgag ttgtacctgg cttcccttga cgagaaattt    8040
cagtgggaag ccgaggcctg gcgattgtat ctcgtgctct tctatattcg ctgtatcggc    8100
ctgttcatct tctgtttcga tggtggtcat gctgacgagc ccccgcggga ggcaagtcca    8160
gacctcggcg cgggaggggc ggagctgaag gacgagagcg cgcaggctgg agctgtccag    8220
agtcctgaga cgctgcggac tcaggttagt aggtaggggac agaagattaa cttgcatgat    8280
cttttccagg gcgtgcggga ggttcagatg gtacttgatt tccacaggtt cgtttgtaga    8340
gacgtcaatg gcttgcaggg ttccgtgtcc tttgggcgcc actaccgtac cttgttttt    8400 tcttttgatc ggtggtggct ctcttgcttc ttgcatgctc agaagcggtg acggggacgc    8460
gcgccgggcg gcagcggttg ttccggaccc gagggcatgg ctggtagtgg cacgtcggcg    8520
ccgcgcacgg gcaggttctg gtactgcgct ctgagaagac ttgcgtgcgc caccacgcgt    8580
cgattgacgt cttgtatctg acgtctctgg gtgaaagcta ccggcccgt gagcttgaac     8640 ctgaaagaga gttcaacaga atcaatttcg gtatcgttaa cggcagcttg tctcagtatt    8700
tcttgtacgt caccagagtt gtcctggtag gcgatctccg ccatgaactg ctcgatttct    8760
tcctcctgaa gatctccgcg acccgctctt cgacggtgg ccgcgaggtc attggagata    8820
cggcccatga gttgggagaa tgcattcatg cccgcctcgt tccagacgcg gctgtaaacc    8880 acggcccct cggagtctct tgcgcgcatc accacctgag cgaggttaag ctccacgtgt     8940
ctggtgaaga ccgcatagtt gcataggcgc tgaaaaaggt agttgagtgt ggtggcaatg    9000
tgttcggcga cgaagaaata catgatccat cgtctcagcg gcatttcgct aacatcgccc    9060
agagcttcca agcgctccat ggcctcgtag aagtccacgg caaaattaaa aaactgggag    9120
tttcgcgcgg acacggtcaa ttcctcctcg agaagacgga tgagttcggc tatggtggcc    9180
cgtacttcgc gttcgaaggc tcccgggatc tcttcttcct cttctatctc ttcttccact    9240
aacatctctt cttcgtcttc aggcgggggc ggaggggggca cgcggcgacg tcgacggcgc    9300
acgggcaaac ggtcgatgaa tcgttcaatg acctctccgc ggcggcggcg catggtttca    9360
gtgacggcgc ggccgttctc gcgcggtcgc agagtaaaaa caccgccgcg catctcctta    9420
aagtggtgac tgggaggttc tccgtttggg agggagaggg cgctgattat acattttatt    9480
aattggcccg tagggactgc acgcagagat ctgatcgtgt caagatccac gggatctgaa    9540
aacctttcga cgaaagcgtc taaccagtca cagtcacaag gtaggctgag tacggcttct    9600
tgtgggcggg ggtggttatg tgttcggtct gggtcttctg tttcttcttc atctcgggaa    9660
ggtgagacga tgctgctggt gatgaaatta aagtaggcag ttctaagacg gcggatggtg    9720
gcgaggagca ccaggtcttt gggtccggct tgctggatac gcaggcgatt ggccattccc    9780
```

```
caagcattat cctgacatct agcaagatct ttgtagtagt cttgcatgag ccgttctacg   9840
ggcacttctt cctcacccgt tctgccatgc atacgtgtga gtccaaatcc gcgcattggt   9900
tgtaccagtg ccaagtcagc tacgactctt tcggcgagga tggcttgctg tacttgggta   9960
agggtggctt gaaagtcatc aaaatccaca agcggtggaa agctcctgt attaatggtg    10020
taagcacagt tggccatgac tgaccagtta actgtctggt gaccagggcg cacgagctcg   10080
gtgtatttaa ggcgcgaata ggcgcgggtg tcaaagatgt aatcgttgca ggtgcgcacc   10140
agatactggt accctataag aaaatgcggc ggtggttggc ggtagagagg ccatcgttct   10200
gtagctggag cgccagggc gaggtcttcc aacataaggc ggtgatagcc gtagatgtac    10260
ctggacatcc aggtgattcc tgcggcggta gtagaagccc gaggaaactc gcgtacgcgg   10320
ttccaaatgt tgcgtagcgg catgaagtag ttcattgtag gcacggtttg accagtgagg   10380
cgcgcgcagt cattgatgct ctatagacac ggagaaaatg aaagcgttca gcgactcgac   10440
tccgtagcct ggaggaacgt gaacggggttg gtcgcggtg taccccggtt cgagacttgt    10500
actcgagccg gccggagccg cggctaacgt ggtattggca ctcccgtctc gacccagcct   10560
acaaaaatcc aggatacgga atcgagtcgt tttgctggtt tccgaatggc agggaagtga   10620
gtcctatttt tttttttgc cgctcagatg catcccgtgc tgcgacagat gcgcccccaa    10680
caacagcccc cctcgcagca gcagcagcag caatcacaaa aggctgtccc tgcaactact   10740
gcaactgccg ccgtgagcgg tgcgggacag cccgcctatg atctggactt ggaagagggc   10800
gaaggactgg cacgtctagg tgcgccttca cccgagcggc atccgcgagt tcaactgaaa   10860
aaagattctc gcgaggcgta tgtgccccaa cagaacctat ttagagacag aagcggcgag   10920
gagccggagg agatgcgagc ttcccgcttt aacgcgggtc gtgagctgcg tcacggtttg   10980
gaccgaagac gagtgttgcg ggacgaggat ttcgaagttg atgaaatgac agggatcagt   11040
cctgccaggg cacacgtggc tgcagccaac cttgtatcgg cttacgagca gacagtaaag   11100
gaagagcgta acttccaaaa gtcttttaat aatcatgtgc gaaccctgat tgcccgcgaa   11160
gaagttaccc ttggtttgat gcatttgtgg gatttgatgg aagctatcat tcagaaccct   11220
actagcaaac ctctgaccgc ccagctgttt ctggtggtgc aacacagcag agacaatgag   11280
gctttcagag aggcgctgct gaacatcacc gaacccgagg ggagatggtt gtatgatctt   11340
atcaacattc tacagagtat catagtgcag gagcggagcc tgggcctggc cgagaaggtg   11400
gctgccatca attactcggt tttgagcttg ggaaaatatt acgctcgcaa aatctacaag   11460
actccatacg ttcccataga caaggagtg aagatagatg ggttctacat gcgcatgacg    11520
ctcaaggtct tgaccctgag cgatgatctt ggggtgtatc gcaatgacag aatgcatcgc   11580
gcggttagcg ccagcaggag gcgcgagtta agcgacaggg aactgatgca cagttttgcaa   11640
agagctctga ctggagctgg aaccgagggt gagaattact tcgacatggg agctgacttg   11700
cagtggcagc ctagtcgcag ggctctgagc gccgcgacgg caggatgtga gcttccttac   11760
atagaagagg cggatgaagg cgaggaggaa gagggcgagt acttggaaga ctgatggcac   11820
aacccgtgtt ttttgctaga tggaacagca agcaccggat cccgcaatgc gggcggcgct   11880
gcagagccag ccgtccggca ttaactcctc ggacgattgg acccaggcca tgcaacgtat   11940
catggcgttg acgactcgca accccgaagc ctttagacag caaccccagg ccaaccgtct   12000
atcggccatc atgaagctg tagtgccttc ccgctctaat cccactcatg agaaggtcct   12060
ggccatcgtg aacgcgttgg tggagaacaa agctattcgt ccagatgagg ccggactggt   12120
```

```
atacaacgct ctcttagaac gcgtggctcg ctacaacagt agcaatgtgc aaaccaattt    12180
ggaccgtatg ataacagatg tacgcgaagc cgtgtctcag cgcgaaaggt tccagcgtga    12240
tgccaacctg ggttcgctgg tggcgttaaa tgctttcttg agtactcagc ctgctaatgt    12300
gccgcgtggt caacaggatt atactaactt tttaagtgct ttgagactga tggtatcaga    12360
agtacctcag agcgaagtgt atcagtccgg tcctgattac ttctttcaga ctagcagaca    12420
gggcttgcag acggtaaatc tgagccaagc ttttaaaaac cttaaaggtt tgtggggagt    12480
gcatgccccg gtaggagaaa gagcaaccgt gtctagcttg ttaactccga actcccgcct    12540
attattactg ttggtagctc ctttcaccga cagcggtagc atcgaccgta attcctattt    12600
gggttaccta ctaaacctgt atcgcgaagc catagggcaa agtcaggtgg acgagcagac    12660
ctatcaagaa attcccaag tcagtcgcgc tttgggacag gaagacactg gcagtttgga    12720
agccactctg aacttcttgc ttaccaatcg gtctcaaaag atccctcctc aatatgctct    12780
tactgcggag gaggagagga tccttagata tgtgcagcag agcgtgggat tgtttctgat    12840
gcaagagggg gcaactccga ctgcagcact ggacatgaca gcgcgaaata tggagcccag    12900
catgtatgcc agtaaccgac cttttcattaa caaactgctg gactacttgc acagagctgc    12960
cgctatgaac tctgattatt tcaccaatgc catcttaaac ccgcactggc tgcccccacc    13020
tggtttctac acgggcgaat atgacatgcc cgaccctaat gacggatttc tgtgggacga    13080
cgtggacagc gatgttttt cacctctttc tgatcatcgc acgtggaaaa aggaaggcgg    13140
cgatagaatg cattcttctg catcgctgtc cggggtcatg ggtgctaccg cggctgagcc    13200
cgagtctgca agtccttttc ctagtctacc ctttctcta cacagtgtac gtagcagcga    13260
agtgggtaga ataagtcgcc cgagtttaat gggcgaagag gagtatctaa acgattcctt    13320
gctcagaccg gcaagagaaa aaaatttccc aaacaatgga atagaaagtt tggtggataa    13380
aatgagtaga tggaagactt atgctcagga tcacagagac gagcctggga tcatggggat    13440
tacaagtaga gcgagccgta gacgccacg ccatgacaga cagaggggtc ttgtgtggga    13500
cgatgaggat tcggccgatg atagcagcgt gctggacttg ggtgggagag aaggggcaa    13560 cccgtttgct catttgcgcc ctcgcttggg tggtatgttg taaaaaaaaa taaaaaaaaa    13620
actcaccaag gccatggcga cgagcgtacg ttcgttcttc tttattatct gtgtctagta    13680
taatgaggcg agtcgtgcta ggcggagcgg tggtgtatcc ggagggtcct cctccttcgt    13740
acgagagcgt gatgcagcag cagcaggcga cggcggtgat gcaatcccca ctggaggctc    13800
cctttgtgcc tccgcgatac ctggcaccta cggagggcag aaacagcatt cgttattcgg    13860
aactggcacc tcagtacgat accaccaggt tgtatctggt ggacaacaag tcggcggaca    13920
ttgcttctct gaactatcag aatgaccaca gcaacttctt gaccacgtg gtgcaaaaca    13980 atgactttac ccctacggaa gccagcaccc agaccattaa ctttgatgaa cgatcgcggt    14040
ggggcggtca gctaaagacc atcatgcata ctaacatgcc aaacgtgaac gagtatatgt    14100
ttagtaacaa gttcaaagcg cgtgtgatgg tgtccagaaa acctcccgac ggtgctgcag    14160
ttggggatac ttatgatcac aagcaggata ttttgaaata tgagtggttc gagtttactt    14220
tgccagaagg caactttca gttactatga ctattgattt tgatgaacaat gccatcatag    14280 ataattactt gaaagtgggt agacagaatg gagtgcttga aagtgacatt ggtgttaagt    14340
tcgacaccag gaacttcaag ctgggatggg atcccgaaac caagttgatc atgcctggag    14400
tgtatacgta tgaagccttc catcctgaca ttgtcttact gcctgctgc ggagtggatt    14460 ttaccgagag tcgtttgagc aaccttcttg gtatcagaaa aaaacagcca tttcaagagg    14520
```

```
gttttaagat tttgtatgaa gatttagaag gtggtaatat tccggccctc ttggatgtag    14580
atgcctatga gaacagtaag aaagaacaaa aagccaaaat agaagctgct acagctgctg    14640
cagaagctaa ggcaaacata gttgccagcg actctacaag ggttgctaac gctggagagg    14700
tcagaggaga caattttgcg ccaacacctg ttccgactgc agaatcatta ttggccgatg    14760
tgtctgaagg aacggacgtg aaactcacta ttcaacctgt agaaaaagat agtaagaata    14820
gaagctataa tgtgttggaa gacaaaatca acacagccta tcgcagttgg tatctttcgt    14880
acaattatgg cgatcccgaa aaaggagtgc gttcctggac attgctcacc acctcagatg    14940
tcacctgcgg agcagagcag gtctactggt cgcttccaga catgatgaag gatcctgtca    15000
ctttccgctc cactagacaa gtcagtaact accctgtggt gggtgcagag cttatgcccg    15060
tcttctcaaa gagcttctac aacgaacaag ctgtgtactc ccagcagctc cgccagtcca    15120
cctcgcttac gcacgtcttc aaccgctttc ctgagaacca gattttaatc cgtccgccgg    15180
cgcccaccat taccaccgtc agtgaaaacg ttcctgctct cacagatcac gggaccctgc    15240
cgttgcgcag cagtatccgg ggagtccaac gtgtgaccgt tactgacgcc agacgccgca    15300
cctgtcccta cgtgtacaag gcactgggca tagtcgcacc cgcgcgtcct tcaagccgca    15360
ctttctaaaa aaaaaaaaaa tgtccattct tatctcgccc agtaataaca ccggttgggg    15420
tctgcgcgct ccaagcaaga tgtacggagg cgcacgcaaa cgttctaccc aacatcctgt    15480
ccgtgttcgc ggacattttc gcgctccatg gggcgccctc aagggccgca ctcgcgttcg    15540
aaccaccgtc gatgatgtaa tcgatcaggt ggttgccgac gcccgtaatt atactcctac    15600
tgcgcctaca tctactgtgg atgcagttat tgacagtgta gtggctgacg ctcgcaacta    15660
tgctcgacgt aagagccggc gaaggcgcat tgccagacgc caccgagcta ccactgccat    15720
gcgagccgca agagctctgc tacgaagagc tagacgcgtg gggcgaagag ccatgcttag    15780
ggcggccaga cgtgcagctt cgggcgccag cgccggcagg tcccgcaggc aagcagccgc    15840
tgtcgcagcg gcgactattg ccgacatggc ccaatcgcga agaggcaatg tatactgggt    15900
gcgtgacgct gccaccggtc aacgtgtacc cgtgcgcacc cgtccccctc gcacttagaa    15960
gatactgagc agtctccgat gttgtgtccc agcggcgagg atgtccaagc gcaaatacaa    16020
ggaagaaatg ctgcaggtta tcgcacctga agtctacggc caaccgttga aggatgaaaa    16080 aaaacccgc aaaatcaagc gggttaaaaa ggacaaaaaa gaagaggaag atggcgatga    16140
tgggctggcg gagtttgtgc gcgagtttgc cccacggcga cgcgtgcaat ggcgtgggcg    16200
caaagttcga catgtgttga gacctggaac ttcggtggtc tttacacccg cgagcgttc    16260 aagcgctact tttaagcgtt cctatgatga ggtgtacggg gatgatgata ttcttgagca    16320
ggcggctgac cgattaggcg agtttgctta tggcaagcgt agtagaataa cttccaagga    16380
tgagacagtg tcgataccct tggatcatgg aaatcccacc cctagtctta aaccggtcac    16440
tttgcagcaa gtgttacccg taactccgcg aacaggtgtt aaacgcgaag gtgaagattt    16500
gtatcccact atgcaactga tggtacccaa acgccagaag ttggaggacg ttttggagaa    16560
agtaaaagtg gatccagata ttcaacctga ggttaaagtg agacccatta agcaggtagc    16620
gcctggtctg ggggtacaaa ctgtagacat taagattccc actgaaagta tggaagtgca    16680
aactgaaccc gcaaagccta ctgccacctc cactgaagtg caaacggatc catggatgcc    16740
catgcctatt acaactgacg ccgccggtcc cactcgaaga tcccgacgaa agtacggtcc    16800
agcaagtctg ttgatgccca attatgttgt acacccatct attattccta ctcctggtta    16860
```

```
ccgaggcact cgctactatc gcagccgaaa cagtacctcc cgccgtcgcc gcaagacacc    16920
tgcaaatcgc agtcgtcgcc gtagacgcac aagcaaaccg actcccggcg ccctggtgcg    16980
gcaagtgtac cgcaatggta gtgcggaacc tttgacactg ccgcgtgcgc gttaccatcc    17040
gagtatcatc acttaatcaa tgttgccgct gcctccttgc agatatggcc ctcacttgtc    17100
gccttcgcgt tcccatcact ggttaccgag gaagaaactc gcgccgtaga agagggatgt    17160
tgggacgcgg aatgcgacgc tacaggcgac ggcgtgctat ccgcaagcaa ttgcggggtg    17220
gttttttacc agccttaatt ccaattatcg ctgctgcaat tggcgcgata ccaggcatag    17280
cttccgtggc ggttcaggcc tcgcaacgac attgacattg gaaaaaaacg tataaataaa    17340
aaaaaaaaaa tacaatggac tctgacactc ctggtcctgt gactatgttt tcttagagat    17400
ggaagacatc aattttttcat ccttggctcc gcgacacggc acgaagccgt acatgggcac    17460
ctggagcgac atcggcacga gccaactgaa cgggggcgcc ttcaattgga gcagtatctg    17520
gagcgggctt aaaaattttg gctcaaccat aaaaacatac gggaacaaag cttggaacag    17580
cagtacagga caggcgctta gaaataaact taaagaccag aacttccaac aaaaagtagt    17640
cgatgggata gcttccggca tcaatggagt ggtagatttg gctaaccagg ctgtgcagaa    17700
aaagataaac agtcgtttgg acccgccgcc agcaaccoca ggtgaaatgc aagtggagga    17760
agaaattcct ccgccagaaa aacgaggcga caagcgtccg cgtcccgatt tggaagagac    17820
gctggtgacg cgcgtagatg aaccgccttc ttatgaggaa gcaacgaagc ttggaatgcc    17880
caccactaga ccgatagccc caatggccac cggggtgatg aaaccttctc agttgcatcg    17940
acccgtcacc ttggatttgc cccctccccc tgctgctact gctgtacccg cttctaagcc    18000
tgtcgctgcc ccgaaaccag tcgccgtagc caggtcacgt cccggggcg ctcctcgtcc    18060 aaatgcgcac tggcaaaata ctctgaacag catcgtgggt ctaggcgtgc aaagtgtaaa    18120
acgccgtcgc tgcttttaat taaatatgga gtagcgctta acttgcctat ctgtgtatat    18180
gtgtcattac acgccgtcac agcagcagag gaaaaaagga agaggtcgtg cgtcgacgct    18240
gagttacttt caagatggcc accccatcga tgctgcccca atgggcatac atgcacatcg    18300
ccggacagga tgcttcggag tacctgagtc cgggtctggt gcagttcgcc cgcgccacag    18360
acacctactt caatctggga aataagttta gaaatcccac cgtagcgccg acccacgatg    18420
tgaccaccga ccgtagccag cggctcatgt tgcgcttcgt gcccgttgac cgggaggaca    18480
atacatactc ttacaaagtg cggtacaccc tggccgtggg cgacaacaga gtgctggata    18540
tggccagcac gttctttgac attaggggtg tgttggacag aggtcccagt ttcaaaccct    18600
attctggtac ggcttacaac tccctggctc ctaaaggcgc tccaaataca tctcagtgga    18660
ttgcagaagg tgtaaaaaat acaactggtg aggaacacgt aacagaagag gaaaccaata    18720
ctactactta cacttttggc aatgctcctg taaaagctga agctgaaatt acaaaagaag    18780
gactcccagt aggtttggaa gtttcagatg aagaaagtaa accgattat gctgataaaa    18840 catatcagcc agaacctcag ctgggagatg aaacttggac tgaccttgat ggaaaaaccg    18900
aaaagtatgg aggcagggct ctcaaacccg atactaagat gaaaccatgc tacgggtcct    18960
ttgccaaacc tactaatgtg aaaggcggtc aggcaaaaca aaaacaacg gagcagccaa    19020 atcagaaagt cgaatatgat atcgacatgg agttttttga tgcggcatcg cagaaaacaa    19080
acttaagtcc taaaattgtc atgtatgcag aaaatgtaaa tttggaaact ccagacactc    19140
atgtagtgta caaacctgga acagaagaca caagttccga agctaatttg ggacaacaat    19200
ctatgcccaa cagacccaac tacattggct tcagagataa ctttattgga cttatgtact    19260
```

```
ataacagtac tggtaacatg ggggtgctgg ctggtcaagc gtctcagtta aatgcagtgg   19320
ttgacttgca ggacagaaac acagaacttt cttaccaact cttgcttgac tctctgggcg   19380
acagaaccag atactttagc atgtggaatc aggctgtgga cagttatgat cctgatgtac   19440
gtgttattga aaatcatggt gtggaagatg aacttcccaa ctactgtttt ccactggacg   19500
gcataggtgt tccaacaacc agttacaaat caatagttcc aaatggagac aatgcgccta   19560
attggaagga acctgaagta aatgaacaa gtgagatcgg acagggtaat ttgtttgcca   19620
tggaaattaa ccttcaagcc aatctatggc aagtttcct ttattccaat gtggctctat   19680
atctcccaga ctcgtacaaa tacacccgt ccaatgtcac tcttccagaa aacaaaaaca   19740
cctacgacta catgaacggg cgggtggtgc cgccatctct agtagacacc tatgtgaaca   19800
ttggtgccag gtggtctctg gatgccatgg acaatgtcaa cccattcaac caccaccgta   19860
acgctggctt gcgttaccga tccatgcttc tgggtaacgg acgttatgtg cctttccaca   19920
tacaagtgcc tcaaaaattc ttcgctgtta aaaacctgct gcttctccca ggctcctaca   19980
cttatgagtg gaactttagg aaggatgtga acatggttct acagagttcc ctcggtaacg   20040
acctgcgggt agatggcgcc agcatcagtt tcacgagcat caacctctat gctacttttt   20100
tccccatggc tcacaacacc gcttccaccc ttgaagccat gctgcggaat gacaccaatg   20160
atcagtcatt caacgactac ctatctgcag ctaacatgct ctaccccatt cctgccaatg   20220
caaccaatat tcccatttcc attccttctc gcaactgggc ggctttcaga ggctggtcat   20280
ttaccagact gaaaaccaaa gaaactccct ctttggggtc tggatttgac ccctactttg   20340
tctattctgg ttctattccc tacctggatg gtaccttcta cctgaaccac acttttaaga   20400
aggtttccat catgtttgac tcttcagtga gctggcctgg aaatgacagg ttactatctc   20460
ctaacgaatt tgaaataaag cgcactgtgg atggcgaagg ctacaacgta gcccaatgca   20520
acatgaccaa agactggttc ttggtacaga tgctcgccaa ctacaacatc ggctatcagg   20580
gcttctacat tccagaagga tacaaagatc gcatgtattc attttttcaga aacttccagc   20640 ccatgagcag gcaggtggtt gatgaggtca attacaaaga cttcaaggcc gtcgccatac   20700
cctaccaaca caacaactct ggctttgtgg gttacatggc tccgaccatg cgccaaggtc   20760
aaccctatcc cgctaactat ccctatccac tcattggaac aactgccgta aatagtgtta   20820
cgcagaaaaa gttcttgtgt gacagaacca tgtggcgcat accgttctcg agcaacttca   20880
tgtctatggg ggcccttaca gacttgggac agaatatgct ctatgccaac tcagctcatg   20940
ctctggacat gaccttgag gtggatccca tggatgagcc caccctgctt tatcttctct   21000
tcgaagtttt cgacgtggtc agagtgcatc agccacaccg cggcatcatc gaggcagtct   21060
acctgcgtac accgttctcg gccggtaacg ctaccacgta agaagcttct tgcttcttgc   21120
aaatagcagc tgcaaccatg gcctgcggat cccaaaacgg ctccagcgag caagagctca   21180
gagccattgt ccaagacctg ggttgcggac cctattttt gggaacctac gataagcgct   21240 tcccgggggtt catggcccc gataagctcg cctgtgccat tgtaaatacg gccggacgtg   21300
agacgggggg agagcactgg ttggctttcg gttggaaccc acgttctaac acctgctacc   21360
tttttgatcc tttttggattc tcggatgatc gtctcaaaca gatttaccag tttgaatatg   21420
agggtctcct gcgccgcagc gctcttgcta ccaaggaccg ctgtattacg ctggaaaaat   21480
ctacccagac cgtgcagggt ccccgttctg ccgcctgcgg actttctgc tgcatgttcc   21540 ttcacgcctt tgtgcactgg cctgaccgtc ccatggacgg aaaccccacc atgaaattgc   21600
```

```
taactggagt gccaaacaac atgcttcatt ctcctaaagt ccagcccacc ctgtgtgaca   21660
atcaaaaagc actctaccat tttcttaata cccattcgcc ttattttcgc tcccatcgta   21720
cacacatcga aagggccact gcgttcgacc gtatggatgt tcaataatga ctcatgtaaa   21780
caacgtgttc aataaacatc actttatttt tttacatgta tcaaggctct gcattactta   21840
tttatttaca agtcgaatgg gttctgacga gaatcagaat gacccgcagg cagtgatacg   21900
ttgcggaact gatacttggg ttgccacttg aattcgggaa tcaccaactt gggaaccggt   21960
atatcgggca ggatgtcact ccacagcttt ctggtcagct gcaaagctcc aagcaggtca   22020
ggagccgaaa tcttgaaatc acaattagga ccagtgcttt gagcgcgaga gttgcggtac   22080
accggattgc agcactgaaa caccatcagc gacggatgtc tcacgcttgc cagcacggtg   22140
ggatctgcaa tcatgcccac atccagatct tcagcattgg caatgctgaa cggggtcatc   22200
ttgcaggtct gcctacccat ggcgggcacc caattaggct tgtggttgca atcgcagtgc   22260 aggggggatca gtatcatctt ggcctgatcc tgtctgattc ctggatacac ggctctcatg   22320
aaagcatcat attgcttgaa agcctgctgg gctttactac cctcggtata aaacatcccg   22380
caggacctgc tcgaaaactg gttagctgca cagccggcat cattcacaca gcagcgggcg   22440
tcattgttag ctatttgcac cacacttctg ccccagcggt tttgggtgat tttggttcgc   22500
tcgggattct cctttaaggc tcgttgtccg ttctcgctgg ccacatccat ctcgataatc   22560
tgctccttct gaatcataat attgccatgc aggcacttca gcttgccctc ataatcattg   22620
cagccatgag gccacaacgc acagcctgta cattcccaat tatggtgggc gatctgagaa   22680
aaagaatgta tcattccctg cagaaatctt cccatcatcg tgctcagtgt cttgtgacta   22740
gtgaaagtta actggatgcc tcggtgctcc tcgtttacgt actggtgaca gatgcgcttg   22800
tattgttcgt gttgctcagg cattagttta aaagaggttc taagttcgtt atccagcctg   22860
tacttctcca tcagcagaca catcacttcc atgcctttct cccaagcaga caccagggcc   22920
aagctaatcg gattcttaac agtgcaggca gcagctcctt tagccagagg gtcatctttta   22980 gcgatcttct caatgcttct tttgccatcc ttctcaacga tgcgcacggg cgggtagctg   23040
aaacccactg ctacaagttg cgcctcttct ctttcttctt cgctgtcttg actgatgtct   23100
tgcatgggga tatgtttggt cttccttggc ttctttttgg ggggtatcgg aggaggagga   23160
ctgtcgctcc gttccggaga cagggaggat tgtgacgttt cgctcaccat taccaactga   23220
ctgtcggtag aagaacctga ccccacacgg cgacaggtgt ttctcttcgg gggcagaggt   23280
ggaggcgatt gcgaagggct gcggtccgac ctggaaggcg gatgactggc agaacccctt   23340
ccgcgttcgg gggtgtgctc cctgtggcgg tcgcttaact gatttccttc gcggctggcc   23400
attgtgttct cctaggcaga gaaacaacag acatggaaac tcagccattg ctgtcaacat   23460
cgccacgagt gccatcacat ctcgtcctca gcgacgagga aaaggagcag agcttaagca   23520
ttccaccgcc cagtcctgcc accacctcta ccctagaaga taaggaggtc gacgcatctc   23580
atgacatgca gaataaaaaa gcgaaagagt ctgagacaga catcgagcaa gacccgggct   23640
atgtgacacc ggtggaacac gaggaagagt tgaaacgctt tctagagaga gaggatgaaa   23700
actgcccaaa acaacgagca gataactatc accaagatgc tggaaatagg gatcagaaca   23760
ccgactacct catagggctt gacggggaag acgcgctcct taaacatcta gcaagacagt   23820
cgctcatagt caaggatgca ttattggaca gaactgaagt gcccatcagt gtggaagagc   23880
tcagccgcgc ctacgagctt aacctctttt cacctcgtac tcccccaaa cgtcagccaa   23940 acggcacctg cgagccaaat cctcgcttaa acttttatcc agcttttgct gtgccagaag   24000
```

```
tactggctac ctatcacatc tttttaaaa atcaaaaaat tccagtctcc tgccgcgcta    24060
atcgcacccg cgccgatgcc ctactcaatc tgggacctgg ttcacgctta cctgatatag    24120
cttccttgga agaggttcca aagatcttcg agggtctggg caataatgag actcgggccg    24180
caaatgctct gcaaaaggga gaaaatggca tggatgagca tcacagcgtt ctggtggaat    24240
tggaaggcga taatgccaga ctcgcagtac tcaagcgaag catcgaggtc acacacttcg    24300
catatcccgc tgtcaacctg cccccctaaag tcatgacggc ggtcatggac cagttactca    24360
ttaagcgcgc aagtccccctt tcagaagaca tgcatgaccc agatgcctgt gatgagggta    24420
aaccagtggt cagtgatgag cagctaaccc gatggctggg caccgactct cccagggatt    24480
tggaagagcg tcgcaagctt atgatggccg tggtgctggt taccgtagaa ctagagtgtc    24540
tccgacgttt ctttaccgat tcagaaacct tgcgcaaact cgaagagaat ctgcactaca    24600
cttttagaca cggctttgtg cggcaggcat gcaagatatc taacgtggaa ctcaccaacc    24660
tggtttccta catgggtatt ctgcatgaga atcgcctagg acaaagcgtg ctgcacagca    24720
ccctgaaggg ggaagcccgc cgtgattaca tccgcgattg tgtctatctg tacctgtgcc    24780
acacgtggca aaccggcatg ggtgtatggc agcaatgttt agaagaacag aacttgaaag    24840
agcttgacaa gctcttacag aaatctctta aggttctgtg acagggttc gacgagcgca    24900 ccgtcgcttc cgacctggca gacctcatct tcccagagcg tctcagggtt actttgcgaa    24960
acggattgcc tgactttatg agccagagca tgcttaacaa ttttcgctct ttcatcctgg    25020
aacgctccgg tatcctgccc gccacctgct gcgcactgcc ctccgacttt gtgcctctca    25080
cctaccgcga gtgccccccg ccgctatgga gtcactgcta cctgttccgt ctggccaact    25140
atctctccta ccactcggat gtgatcgagg atgtgagcgg agacggcttg ctggagtgtc    25200
actgccgctg caatctgtgc acgccccacc ggtccctagc ttgcaacccc cagttgatga    25260
gcgaaaccca gataataggc acctttgaat tgcaaggccc cagcagccaa ggcgatgggt    25320
cttctcctgg gcaaagttta aaactgaccc cgggactgtg gacctccgcc tacttgcgca    25380
agtttgctcc ggaagattac caccccctatg aaatcaagtt ctatgaggac caatcacagc    25440
ctccaaaggc cgaactttcg gcctgcgtca tcacccaggg ggcaattctg gcccaattgc    25500
aagccatcca aaaatcccgc caagaatttc tactgaaaaa gggtaagggg gtctaccttg    25560 accccagac cggcgaggaa ctcaacacaa ggttccctca ggatgtccca acgacgagaa    25620
aacaagaagt tgaaggtgca gccgccgccc ccagaagata tggaggaaga ttgggacagt    25680
caggcagagg aggcggagga ggacagtctg gaggacagtc tggaggaaga cagtttggag    25740
gaggaaaacg aggaggcaga ggaggtggaa gaagtaaccg ccgacaaaca gttatcctcg    25800
gctgcgagga caagcaacag cgctaccatc tccgctccga gtcgaggaac ccggcggcgt    25860
cccagcagta gatgggacga gaccggacgc ttcccgaacc caaccagcgc ttccaagacc    25920
ggtaagaagt atcggcaggg atacaagtcc tggcgggggc ataagaatgc catcatctcc    25980
tgcttgcatg agtgcggggg caacatatcc ttcacgcggc gctacttgct attccaccat    26040
ggggtgaact ttccgcgcaa tgttttgcat tactaccgtc acctccacag cccctactat    26100
agccagcaaa tcccggcagt ctcgacagat aaagacagcg gcggcgacct caacagaaa    26160 accagcagcg gcagttagaa aatacacaac aagtgcagca acaggaggat taaagattac    26220
agccaacgag ccagcgcaaa cccgagagtt aagaaatcgg atctttccaa ccctgtatgc    26280
catcttccag cagagtcggg gtcaagagca ggaactgaaa ataaaaaacc gatctctgcg    26340
```

```
ttcgctcacc agaagttgtt tgtatcacaa gagcgaagat caacttcagc gcactctcga    26400
ggacgccgag gctctcttca acaagtactg cgcgctgact cttaaagagt aggcagcgac    26460
cgcgcttatt caaaaaaggc gggaattaca tcatcctcga catgagtaaa gaaattccca    26520
cgccttacat gtggagttat caaccccaaa tgggattggc ggcaggcgcc tcccaggact    26580
actccacccg catgaattgg ctcagcgccg ggccttctat gatttctcga gttaatgata    26640
tacgcgccta ccgaaaccaa atacttttgg aacagtcagc tcttaccacc acgcccgcc    26700
aacaccttaa tcccagaaat tggcccgccg ccctagtgta ccaggaaagt cccgctccca    26760
ccactgtatt acttcctcga gacgcccagg ccgaagtcca aatgactaat gcaggtgcgc    26820
agttagctgg cggctccacc ctatgtcgtc acaggcctcg gcataatata aaacgcctga    26880
tgatcagagg ccgaggtatc cagctcaacg acgagtcggt gagctctccg cttggtctac    26940
gaccagacgg aatctttcag attgccggct gcgggagatc ttccttcacc cctcgtcagg    27000
ctgttctgac tttggaaagt tcgtcttcgc aaccccgctc gggcgaatc gggaccgttc    27060
aatttgtgga ggagtttact ccctctgtct acttcaaccc cttctccgga tctcctgggc    27120
attacccgga cgagttcata ccgaacttcg acgcgattag cgagtcagtg gacggctacg    27180
attgatgtct ggtgacgcgg ctgagctatc tcggctgcga catctagacc actgccgccg    27240
cttttcgctgc tttgcccggg aactcattga gttcatctac ttcgaactcc caaggatca    27300
ccctcaaggt ccggccacg gagtgcggat ttctatcgaa ggcaaaatag actctcgcct    27360
gcaacgaatt ttctcccagc ggccgtgct gatcgagcga gaccagggaa acaccacggt    27420
ttccatctac tgcatttgta atcaccccgg attgcatgaa agcctttgct gtcttatgtg    27480
tactgagttt aataaaaact gaattaagac tctcctacgg actgccgctt cttcaacccg    27540
gattttacaa ccagaagaac gaaacttttc ctgtcgtcca ggactctgtt aacttcacct    27600
ttcctactca caaactagaa gctcaacgac tacaccgctt ttccagaagc attttcccta    27660
ctaatactac tttcaaaacc ggaggtgagc tccaaggtct tcctacagaa aacccttggg    27720
tggaagcggg ccttgtagtg ctaggaattc ttgcgggtgg gcttgtgatt attctttgct    27780
acctatacac accttgcttc actttcttag tggtgttgtg gtattggttt aaaaaatggg    27840
gcccatacta gtcttgcttg ttttactttc gcttttggaa ccgggttctg ccaattacga    27900
tccatgtcta gacttcgacc cagaaaactg cacacttact tttgcacccg acacaagccg    27960
catctgtgga gttcatcgcc tctcttacga acttggcccc caacgacaaa aatttacctg    28020
catggtggga atcaaccca tagttatcac ccagcaaagt ggagatacta agggttgcat    28080
tcactgctcc tgcgattcca tcgagtgcac ctacaccctg ctgaagaccc tatgcggcct    28140
aagagacctg ctaccaatga attaaaaaat gattaataaa aaatcactta cttgaaatca    28200
gcaataaggt ctctgttgaa attttctccc agcagcacct cacttccctc ttcccaactc    28260
tggtattcta aaccccgttc agcggcatac tttctccata cttaaaggg gatgtcaaat    28320
tttagctcct ctcctgtacc cacaatcttc atgtctttct tcccagatga ccaagagagt    28380
ccggctcagt gactccttca accctgtcta ccctatgaa gatgaaagca cctcccaaca    28440
ccccttata acccagggt ttatttccc aaatggcttc acacaaagcc caaacggagt    28500
tcttacttta aaatgtttaa ccccactaac aaccacaggc ggatctctac agctaaaagt    28560
gggagggga cttacagtgg atgacaccaa cggttttttg aaagaaaaca taagtgccac    28620
cacaccactc gttaagactg gtcactctat aggtttacca ctaggagccg gattgggaac    28680
gaatgaaaat aaactttgta tcaaattagg acaaggactt acattcaatt caaacaacat    28740
```

```
ttgcattgat gacaatatta acaccttatg gacaggagtc aaccccaccg aagccaactg   28800
tcaaatcatg aactccagtg aatctaatga ttgcaaatta attctaacac tagttaaaac   28860
tggagcacta gtcactgcat ttgtttatgt tataggagta tctaacaatt ttaatatgct   28920
aactacacac agaaatataa attttactgc agagctgttt ttcgattcta ctggtaattt   28980
actaactaga ctctcatccc tcaaaactcc acttaatcat aaatcaggac aaaacatggc   29040
tactggtgcc attactaatg ctaaaggttt catgcccagc acgactgcct atcctttcaa   29100
tgataattct agagaaaaag aaaactacat ttacggaact tgttactaca cagctagtga   29160
tcgcactgct tttcccattg acatatctgt catgcttaac cgaagagcaa taaatgacga   29220
gacatcatat tgtattcgta taacttggtc ctggaacaca ggagatgccc cagaggtgca   29280
aacctctgct acaaccctag tcacctcccc atttaccttt tactacatca gagaagacga   29340
ctgacaaata aagtttaact tgtttatttg aaaatcaatt cacaaaatcc gagtagttat   29400
tttgcctccc ccttcccatt taacagaata caccaatctc tccccacgca cagctttaaa   29460
catttggata ccattagata tagacatggt tttagattcc acattccaaa cagtttcaga   29520
gcgagccaat ctggggtcag tgatagataa aaatccatcg ggatagtctt ttaaagcgct   29580
ttcacagtcc aactgctgcg gatgcgactc cggagtctgg atcacggtca tctggaagaa   29640
gaacgatggg aatcataatc cgaaaacggt atcggacgat tgtgtctcat caaacccaca   29700
agcagccgct gtctgcgtcg ctccgtgcga ctgctgttta tgggatcagg gtccacagtg   29760
tcctgaagca tgattttaat agcccttaac atcaactttc tggtgcgatg cgcgcagcaa   29820
cgcattctga tttcactcaa atctttgcag taggtacaac acattattac aatattgttt   29880
aataaaccat aattaaaagc gctccagcca aaactcatat ctgatataat cgcccctgca   29940
tgaccatcat accaaagttt aatataaatt aaatgacgtt ccctcaaaaa cacactaccc   30000
acatacatga tctcttttgg catgtgcata ttaacaatct gtctgtacca tggacaacgt   30060
tggttaatca tgcaacccaa tataaccttc cggaaccaca ctgccaacac cgctccccca   30120
gccatgcatt gaagtgaacc ctgctgatta caatgacaat gaagaaccca attctctcga   30180
ccgtgaatca cttgagaatg aaaaatatct atagtggcac aacatagaca taaatgcatg   30240
catcttctca taatttttaa ctcctcagga tttagaaaca tatcccaggg aataggaagc   30300
tcttgcagaa cagtaaagct ggcagaacaa ggaagaccac gaacacaact tacactatgc   30360
atagtcatag tatcacaatc tggcaacagc gggtggtctt cagtcataga agctcgggtt   30420
tcattttcct cacaacgtgg taactgggct ctggtgtaag ggtgatgtct ggcgcatgat   30480
gtcgagcgtg cgcgcaacct tgtcataatg gagttgcttc ctgacattct cgtattttgt   30540
atagcaaaac gcggccctgg cagaacacac tcttcttcgc cttctatcct gccgcttagc   30600
gtgttccgtg tgatagttca agtacaacca cactcttaag ttggtcaaaa gaatgctggc   30660
ttcagttgta atcaaaactc catcgcatct aatcgttctg aggaaatcat ccaagcaatg   30720
caactggatt gtgtttcaag caggagagga gagggaagag acggaagaac catgttaatt   30780
tttattccaa acgatctcgc agtacttcaa attgtagatc gcgcagatgg catctctcgc   30840
ccccactgtg ttggtgaaaa agcacagcta gatcaaaaga aatgcgattt tcaaggtgct   30900
caacggtggc ttccagcaaa gcctccacgc gcacatccaa gaacaaaaga ataccaaaag   30960
aaggagcatt ttctaactcc tcaatcatca tattacattc ctgcaccatt cccagataat   31020
tttcagcttt ccagccttga attattcgtg tcagttcttg tggtaaatcc aatccacaca   31080
```

-continued

```
ttacaaacag gtcccggagg gcgccctcca ccaccattct taaacacacc ctcataatga    31140
caaaatatct tgctcctgtg tcacctgtag cgaattgaga atggcaacat caattgacat    31200
gcccttggct ctaagttctt ctttaagttc tagttgtaaa aactctctca tattatcacc    31260
aaactgctta gccagaagcc ccccgggaac aagagcaggg gacgctacag tgcagtacaa    31320
gcgcagacct ccccaattgg ctccagcaaa aacaagattg gaataagcat attgggaacc    31380
gccagtaata tcatcgaagt tgctggaaat ataatcaggc agagtttctt gtaaaaattg    31440
aataaaagaa aaatttgcca aaaaaacatt caaaacctct gggatgcaaa tgcaataggt    31500
taccgcgctg cgctccaaca ttgttagttt tgaattagtc tgcaaaaata aaaaaaaaaa    31560
caagcgtcat atcatagtag cctgacgaac agatggataa atcagtcttt ccatcacaag    31620
acaagccaca gggtctccag ctcgaccctc gtaaacctg tcatcatgat taaacaacag    31680
caccgaaagt tcctcgcggt gaccagcatg aataattctt gatgaagcat acaatccaga    31740
catgttagca tcagttaacg agaaaaaaca gccaacatag cctttgggta taattatgct    31800
taatcgtaag tatagcaaag ccaccctcg cggatacaaa gtaaaaggca caggagaata    31860
aaaaatataa ttatttctct gctgctgttc aggcaacgtc gccccggtc cctctaaata    31920 cacatacaaa gcctcatcag ccatggctta ccagacaaag tacagcgggc acacaaagca    31980
caagctctaa agtgactctc caacctctcc acaatatata tatacacaag ccctaaactg    32040
acgtaatggg agtaaagtgt aaaaaatccc gccaaaccca acacacaccc cgaaactgcg    32100
tcaccaggga aaagtacagt ttcacttccg caatcccaac aggcgtaact tcctctttct    32160
cacggtacgt gatatcccac taacttgcaa cgtcattttc ccacggtcgc accgcccctt    32220
ttagccgtta accccacagc caatcaccac acgatccaca ctttttaaaa tcacctcatt    32280
tacatattgg caccattcca tctataaggt atattatata gataga                  32326
```

<210> SEQ ID NO 30
<211> LENGTH: 26
<212> TYPE: DNA
<213> ORGANISM: Artificial Sequence
<220> FEATURE:
<223> OTHER INFORMATION: splice acceptor sequence

<400> SEQUENCE: 30
tgctaatctt cctttctctc ttcagg                                          26

<210> SEQ ID NO 31
<211> LENGTH: 14
<212> TYPE: DNA
<213> ORGANISM: Artificial Sequence
<220> FEATURE:
<223> OTHER INFORMATION: splice acceptor sequence

<400> SEQUENCE: 31
tttctctctt cagg                                                       14

GROUP B ADENOVIRUS MODIFIED IN THE E4ORF4 REGION

CROSS REFERENCE TO RELATED APPLICATIONS

The present application is filed under 35 U.S.C. § 371 as the U.S. national phase of International Application No. PCT/EP2015/057994, filed Apr. 13, 2015, which designated the U.S. and claims the benefit of priority to United Kingdom Patent Application No. GB 1406608.8 filed Apr. 12, 2014, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Oct. 10, 2016, is named STPS123_US_SeqListing.txt and is 182 kilobytes in size.

FIELD OF THE INVENTION

The present disclosure relates to a type B adenovirus wherein E4orf4 is deleted or non-functional and generally having a DNA sequence in the E3 region, compositions containing the virus, for example pharmaceutical formulations of the virus, processes for making the viruses and the compositions and use of any one of the same in treatment, particularly in the treatment of cancer, such as colorectal cancer and ovarian cancer.

BACKGROUND

Enadenotucirev (EnAd; formerly called ColoAd1) is a chimeric oncolytic adenovirus with fibre, penton and hexon from Ad11p. It was created by a bioselection process, WO2005/118825, and has a chimeric E2B region. EnAd is currently in development for the treatment of colorectal cancer and it appears to selectively elicit necrotic death of colon cancer cells in vivo.

The advantageous properties of EnAd were thought to be primarily attributable to the chimeric E2B region. However, the present inventors believe that some of the advantageous properties of EnAd, for example the ability of an infected cell to produce intact new virus particles and to selectively induce necrosis of cancer cells is due at least in part to the E4orf4 deletion.

The present inventors believe this significant insight can be employed to genetically engineer alternative oncolytic viruses and viral vectors.

SUMMARY OF INVENTION

The present disclosure provides an adenovirus having a genome comprising the sequence of formula (I):

wherein:
- $B_1$ is bond or comprises: E1A, E1B or E1A-E1B;
- $B_A$ is E2B-L1-L2-L3-E2A-L4;
- $B_2$ comprises a transgene and/or a DNA sequence from an E3 region encoding protein selected from the group consisting of a 12.1K, 16.1K, 18.5K, 20.3K, 20.6K, 10.3K, 15.2K, 15.3K and combinations thereof, for example including all said E3 proteins;
- $B_X$ is a bond or a DNA sequence comprising: a restriction site, one or more transgenes or both;
- $B_B$ is L5;
- $B_Y$ is a bond or a DNA sequence comprising: a restriction site, one or more transgenes or both;
- $B_3$ is an E4 region wherein the region E4orf4 is deleted, for example partially deleted, truncated or non-functional.

In one embodiment the oncolytic virus has a formula (Ia):

wherein:
- $B_1$ is a bond or comprises: E1A, E1B or E1A-E1B;
- $B_A$ is E2B-L1-L2-L3-E2A-L4;
- $B_2$ is a bond or comprises E3;
- $B_B$ comprises L5;
- $B_Y$ comprises a transgene encoding a B7 protein or an active fragment thereof; and
- $B_3$ is an E4 region wherein the region E4orf4 is deleted, for example partially deleted, truncated or non-functional.

In one embodiment the adenovirus of the disclosure does not comprise a transgene.

In one embodiment the adenovirus of the disclosure includes a transgene. Advantageously, arming a virus, with a transgene encoding certain proteins that can be expressed inside the cancer cell, may enable the body's own defences to be employed to combat tumour cells more effectively, for example by making the cells more visible to the immune system or by delivering a therapeutic gene/protein preferentially to target tumour cells.

Furthermore, the ability to insert transgenes that are reporters into the genome can aid clinical or pre-clinical studies.

In one embodiment the transgene is located in $B_2$. In one embodiment the transgene is located in $B_X$, for example under the control of an exogenous promoter. In one embodiment the transgene is located in $B_Y$, for example under the control of an exogenous promoter.

In one embodiment a transgene is located in $B_X$ and $B_Y$, for example the transgenes may be the same or different.

In one embodiment the transgene is part of a transgene cassette comprising at least one coding sequence and optionally one or more elements independently selected from:
- i. a regulator of gene expression, such as an exogenous promoter or splice acceptor;
- ii. an internal ribosome entry (IRES) DNA Sequence;
- iii. a DNA sequence encoding a high self-cleavage efficiency 2A peptide;
- iv. a DNA sequence encoding a polyadenylation sequence; and
- v. a combination thereof.

In one embodiment only the E4orf4 region is deleted, for example partially deleted, truncated or non-functional in the E4 part of the genome. Thus in one embodiment the adenoviruses of the present disclosure comprise at least a functional E4orf1.

Previous studies suggest that adenoviruses express early E4orf1 and E4orf4 proteins that hijack cellular growth regulatory networks to replicate the viral genome and proteins. For example, the gene product of the E4orf1 region has been implicated in the activation of MYC, which in turn promotes increased nucleotide biosynthesis from glucose intermediates and enhances viral replication. Whilst not wishing to be bound by theory the protein encoded by the E4orf4 region in the virus is thought to inactivate the AMPK pathway of energy sensing. Thus viruses of the present disclosure which are deleted, partially deleted, truncated or lack a functional E4orf4 region may not be able to inactivate the AMPK pathway.

As a result, the inventors believe that this may result in the suppression of mTOR. This change is thought to cause conflicting signals between E4orf1 and E4orf4, which may subsequently create a microenvironment in the cancer cell, which is both anabolic and catabolic.

In healthy cells, such a mixed microenvironment may lead to endoplasmic reticulum (ER) stress and consequently apoptosis. In comparison, tumour cells generally have upregulated growth in comparison to healthy cells and tend to continue to replicate in this microenvironment created by the virus. This continued activity may result in ATP loss and ultimately result in necrotic-like death of the cancer cell. Therefore it is now hypothesised that the oncolytic properties of the adenovirus may be derived from or enhanced by the deletion or inactivation of the E4orf4 region.

In addition the E4orf4 modification of the present disclosure appears to a make positive contribution to the generation of viable and appropriately packaged virus. This is particularly true when the virus has a rapid lytic cycle, for example inducing oncolysis in 50 hours or less, such as 40 hours or less. This is because the viral systems are under pressure to package the virus particles. The presence of the full length E4 region appears to restrict the ability of the infected cell to cope with the increased virus genome load resulting in lower amounts of properly packaged virus particles being produced. The latter is likely to reduce the benefits of an oncolytic virus in vivo because rapid virus replication of viral particles may contribute the death of the infected cancer cell and may also be important in establishing levels of virus titre that have a therapeutic effect (i.e. a rate of replication that is faster than the rate of clearance by the hosts immune system).

It may be that the E4orf4 region is a negative regulator of virus genes in the E4 and/or E2 region. Thus removing the restriction exerted by the E4orf4 region allows the viral systems to function at full capacity. Alternatively, E4orf4 acts at the cellular level to restrict virus particle production.

In addition E4orf4 may have role in the inducing death of cancers cells, in particular that is specific to the cancer cells, for example where it induces cancer cell death by apoptosis, whereas when E4orf4 is deleted, partially deleted, truncated or non-functional cell death is via an immunogenic necrosis-like mechanism. It may therefore also have a role to play reducing the immune response to the virus In contrast the presence or absence of the E3 region appears to have little influence on the synthesis of viable virus.

Thus the present disclosure also extends to a process comprising the step of deleting the E4orf4 region or rendering the same non-functional, for example by deleting part of the region or disrupting the region in an adenovirus, in particular to render the virus oncolytic.

Also provided is a composition comprising a virus or vector according to the present disclosure, in particular a pharmaceutical composition for example comprising an adenovirus according to the disclosure and a pharmaceutically acceptable excipient.

The present disclosure further relates to an adenovirus or composition according to the disclosure for use in treatment, for example for use in the treatment of cancer, such as colorectal cancer or ovarian cancer.

The disclosure also relates to a method of treatment comprising administering a therapeutically effective amount of a virus as described herein or a composition comprising the same to a patient in need thereof, in particular a human patient, for example a cancer patient, such as a colorectal cancer or ovarian cancer patient.

Also provided is an adenovirus according to the present disclosure for the manufacture of a medicament for the treatment of cancer, for example colorectal cancer or ovarian cancer.

DETAILED DESCRIPTION

In one embodiment the adenovirus is a human adenovirus.

"Adenovirus" "serotype" or adenoviral serotype" as employed herein refers to any adenovirus that can be assigned to any of the over 50 currently known adenoviral serotypes, which are classified into subgroups A-F, and further extends to any, as yet, unidentified or unclassified adenoviral serotypes. See, for example, Strauss, "Adenovirus infections in humans," in The Adenoviruses, Ginsberg, ea., Plenum Press, New York, N.Y., pp. 451-596 (1984) and Shenk, "Adenoviridae: The Viruses and Their Replication," in Fields Virology, Vol. 2, Fourth Edition, Knipe, 35 ea., Lippincott Williams & Wilkins, pp. 2265-2267 (2001).

In one embodiment there is provided an adenovirus according to the present disclosure, for example a group B virus, wherein the E3 region has a sequence comprising SEQ ID NO: 7, and when the backbone genomic DNA of the virus is from EnAd the E2B is a sequence other than 8.

Subgroup B adenovirus include: Ad3, Ad7, Ad11, Ad14, Ad16, Ad21, Ad34, Ad35 and Ad51. In one embodiment the subgroup B adenovirus is independently selected from the group comprising or consisting of: Ad3, Ad7, Ad11, Ad14, Ad16, Ad21, Ad34 and Ad51, in particular Ad11, such as Ad11a or Ad11p.

In one independent aspect of the invention there is provided an Ad3, Ad7, Ad14, Ad16, Ad21, Ad34, Ad35 and Ad51 adenovirus which is deleted or non-functional in the E4orf4 region of E4 and the E3 is either full-length E3, partially deleted in E3 or fully deleted in E3.

In one independent aspect of the invention there is provided an Ad11 adenovirus, for example Ad11a, Ad11p or EnAd, OvAd1 or OvAd2, non-functional in the E4orf4 region of E4 (e.g. has an E4orf4 sequence that is mutated to render it non-functional in a relevant respect) and in the E3 region is either full-length E3, partially deleted in E3 or fully deleted in E3 or contains a transgene in E3 (with or without part or all of the E3 sequence).

In one embodiment the adenovirus of the disclosure has the capsid, such as the hexon and/or fibre of a subgroup B adenovirus, such as Ad11, in particular Ad11p.

In one embodiment the adenovirus is chimeric. When an adenovirus is chimeric then the characteristics of the outer capsid will be employed to determine the serotype. Thus group B viruses also include chimeric viruses with a group B fibre, hexon and/or penton. Chimeric as employed herein refers to a virus that comprises DNA from at least two different virus serotypes.

In one embodiment a virus of the present disclosure comprises a chimeric E2B region which increases the rate of virus replication in comparison to the parent virus, for example comprises an E2B region of SEQ ID NO: 8, and also E4orf4 is deleted or a non-functional. This combination may be particularly advantageous in providing viruses with oncolytic properties.

In one embodiment the chimeric adenovirus is an Ad11 chimera having at least the fibre and/or hexon and/or penton of Ad11.

EnAd as employed herein refers the chimeric adenovirus of SEQ ID NO: 1 as disclosed in WO2005/118825. EnAd has a chimeric E2B region, which features DNA from Ad11p and Ad3 as shown in SEQ ID NO: 8 herein. The genomic DNA sequence of EnAd is provided in SEQ ID NO: 1. The E3 region of EnAd comprises E3orf1 and E3orf2 identical to Ad11. It also comprises a fusion construct from Ad3 and Ad11 comprising E3orf3 and E3orf8, as shown in SEQ ID NO: 7, which encodes a 109 amino acid protein of about 12 KDa.

All human adenovirus genomes examined to date have the same general organisation i.e., the genes encoding specific functions are located at the same position in the viral genome (referred to herein as structural elements). Each end of the viral genome has a short sequence known as the inverted terminal repeat (or ITR), which is required for viral replication. The viral genome contains five early transcription units (E1A, E1B, E2, E3, and E4), three delayed early units (IX, IVa2 and E2 late) and one late unit (major late) that is processed to generate five families of late mRNAs (L1-L5). Proteins encoded by the early genes are primarily involved in replication and modulation of the host cell response to infection, whereas the late genes encode viral structural proteins. Early genes are prefixed by the letter E and the late genes are prefixed by the letter L.

Unless the context indicates otherwise adenovirus as employ herein refers to a replication competent virus and viral vectors.

In one embodiment the virus is replication competent. Replication competent in the context of the present specification refers to a virus that possesses all the necessary machinery to replicate in vitro and in vivo, i.e. without the assistance of a packaging cell line. A viral vector, for example deleted in the E1 region, capable of replicating in a complementary packaging cell line is not a replication competent virus in the present context.

In one embodiment the virus is replication deficient, for example deleted in the E1 region. Viral vectors are replication deficient and require a packaging cell to provide a complementary gene to allow replication. For replication deficient viral vectors deleting the E4orf4 or rendering same non-functional may increase the yield of vector prepared using a packaging cell line.

In one embodiment the adenovirus of the disclosure is oncolytic. Oncolytic adenovirus as employed herein means an adenovirus that selectively kills cancer cells as compared with non-cancer cells.

Selectively, as employed herein refers to the activity in killing cancer cells is significantly higher than the activity in killing normal, healthy cells, for example the killing activity is 2, 3, 4, 5, 6, 7, 8, 9 or 10 times higher or more in cancer cells in comparison to the killing ability in normal, healthy cells.

In one embodiment the oncolytic virus is apoptotic. That is, it hastens programmed cell death.

In one embodiment the oncolytic virus is cytolytic. The cytolytic activity of oncolytic adenoviruses of the disclosure can be determined in representative tumour cell lines and the data converted to a measurement of potency, for example with an adenovirus belonging to subgroup C, preferably Ad5, being used as a standard (i.e. given a potency of 1). A suitable method for determining cytolytic activity is an MTS assay (see Example 4, FIG. 2 of WO2005/118825 incorporated herein by reference).

In one embodiment the oncolytic virus is necrolytic. That is, it causes or hastens cell necrosis or immunogenic cell death.

In one embodiment the oncolytic virus kills tumour cells by oncosis. That is, it causes or hastens a form of cell death accompanied by cellular swelling, organelle swelling, blebbing, and increased membrane permeability.

Adenovirus genome as employed herein refers to the DNA sequence encoding the structural proteins and elements relevant to the function/life cycle of an adenovirus. Genomic DNA derived from a virus, for example EnAd or Ad11 as employed herein refers to part of all of the DNA from said virus in a contiguous sequence wherein said sequence can be identified as originating from the relevant virus. In one embodiment the genomic DNA may be 30, 40, 50, 60, 70, 80, 90 or 100% from the given the virus. In one embodiment the virus is EnAd the E2B region is other than SEQ ID NO: 8. In one embodiment when EnAd comprises an E2B region with a sequence of SEQ ID NO: 8 then the E3 region is other than SEQ ID NO: 7. In one embodiment when EnAd comprises an E2B region with a sequence of SEQ ID NO: 8, then B2 is a transgene (for example under the control of an exogenous promoter) or an E3 proteins is present or the full E3 region is present including a mutated form thereof which is non-functional. The E3 protein or E3 region may further comprise a transgene, for example inserted at the 3' or 5' end of the sequence or inserted in a disruptive way in the gene relevant coding sequence.

In one embodiment the virus is not OvAd1. In one embodiment the virus is not OvAd2.

A bond refers to a bond connecting the one DNA sequence to another DNA sequence, for example connecting one section of the virus genome to another. Thus when a variable in formula (I) or other formula herein represents a bond the feature or element represented by the bond is absent i.e. deleted.

As the structure of adenoviruses is, in general, similar and the elements below are discussed in terms of the structural elements, which are known to the skilled person. When an element is referred to herein then we refer to the DNA sequence encoding the element or a DNA sequence encoding the same structural protein of the element in an adenovirus, given the redundancy of the DNA code and bearing in mind the viruses' preference for codon usage.

The skilled person will appreciate that the elements in the formulas herein, such as formula (I) and (Ia) are contiguous and may embody non-coding DNA sequences as well as the genes and coding DNA sequences (structural features) mentioned herein. In one or more embodiments the formulas of the present disclosure are attempting to describe a naturally occurring sequence in the adenovirus genome. In this context it will be clear to the skilled person that the formula is referring to the major elements characterising the relevant section of genome and is not intended to be an exhaustive description of the relevant genomic stretch of DNA. Furthermore, the full length of formula (I) and (Ia) is intended to represent the total genomic sequence of the relevant adenovirus with at least E4orf4 deleted and optional sequences of transgenes etc inserted in a limited number of places.

Any structural element from an adenovirus employed in the viruses of the present disclosure may comprise or consist of the natural sequence or may have similarity over the given length of at least 95%, such as 96%, 97%, 98%, 99% or 100%. The original sequence may be modified to omit 10%, 9%, 8%, 7%, 6%, 5%, 4%, 3%, 2% or 1% of the genetic material. The skilled person is aware that when making changes the reading frames of the virus must be not disrupted such that the expression of structural proteins is disrupted.

In one embodiment the element is a full-length sequence i.e. the full-length gene.

In one embodiment the element is less than a full-length and retains the same or corresponding function as the full-length sequence.

The structural genes encoding structural or functional proteins of the adenovirus are generally linked by non-coding regions of DNA. Thus there is some flexibility about where to "cut" the genomic sequence of the structural element of interest for inclusion into the viruses of the present disclosure. Thus for the purposes of the present specification, the element will be considered a structural element of reference to the extent that it is fit for purpose and does not encode extraneous material. Thus, if appropriate the gene will be associated with suitable non-coding regions, for example as found in the natural structure of the virus.

Below follows a discussion relating to specific structural elements of adenoviruses. The Inverted Terminal Repeat (ITR) sequences are common to all known adenoviruses and were so named because of their symmetry, and are the viral chromosome origins of replication. Another property of these sequences is their ability to form a hairpin.

The 5'ITR as employed herein refers to part or all of an ITR from 5' end of an adenovirus which retains the function of the ITR when incorporated into an adenovirus in an appropriate location. In one embodiment the 5'ITR has the sequence from about 1 bp to 138 bp of SEQ ID NO: 1.

The 3'ITR as employed herein refers to part or all of an ITR from 3' end of an adenovirus which retains the function of the ITR when incorporated into an adenovirus in an appropriate location. In one embodiment the 3'ITR has the sequence from about 32189 bp to 32326 bp of SEQ ID NO: 1.

$B_1$ as employed herein refers to the DNA sequence encoding: part or all of an E1A from an adenovirus, part or all of the E1B region of an adenovirus, or independently a part or all of E1A and E1B region of an adenovirus.

In one embodiment $B_1$ is represents a full-length sequence of the E1 region (i.e. E1A and E1B), and for example does not comprise a transgene.

When $B_1$ is a bond then E1A and E1B sequences will be omitted from the virus. In one embodiment $B_1$ is a bond and thus the virus is a vector.

In one embodiment $B_1$ further comprises a transgene. It is known in the art that the E1 region can accommodate a transgene which may be inserted in a disruptive way into the E1 region (i.e. in the "middle" of the sequence) or part or all of the E1 region may be deleted to provide more room to accommodate genetic material.

E1A as employed herein refers to the DNA sequence encoding the part of an adenovirus E1 region designated as E1A or a fragment thereof. It may be mutated such that the protein encoded by the E1A gene has conservative or non-conservative amino acid changes, such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same, as appropriate.

E1B as employed herein refers to the DNA sequence encoding the relevant part an adenovirus E1 region designated as E1B or a fragment thereof, it may be mutated such that the protein encoded by the E1B gene has conservative or non-conservative amino acid changes, such that it has: the same function as wild-type (i.e. the corresponding non-mutated protein); increased function in comparison to wild-type protein; decreased function, such as no function in comparison to wild-type protein; or has a new function in comparison to wild-type protein or a combination of the same as appropriate.

Thus $B_1$ can be modified or unmodified relative to a wild-type E1 region, such as a wild-type E1A and/or E1B. The skilled person can easily identify whether E1A and/or E1B are present or (part) deleted or mutated.

In one embodiment a full length unmodified E1 region is employ in $B_1$. This is particular relevant to replication competent viruses because the E1 region is essential for replication.

Wild-type as employed herein refers to a known adenovirus or fragment thereof. A known adenovirus is one that has been identified and named, regardless of whether the sequence is available. In one embodiment the adenovirus is one disclosed herein, for example a group B virus, such as Ad3, Ad11 or even EnAd.

In one embodiment $B_1$ has the sequence from 139 bp to 3932 bp of SEQ ID NO: 1.

$B_A$ as employed herein refers to the DNA sequence encoding the E2B-L1-L2-L3-E2A-L4 regions including any non-coding sequences, as appropriate. Generally this sequence will not comprise a transgene. In one embodiment the sequence is substantially similar or identical to a contiguous sequence from a known adenovirus, for example an adenovirus disclosed herein, such as a group B virus, in particular Ad11 or EnAd. Thus the elements E2B, L1, L2, L3, E2A and L4 will be in an uninterrupted sequence where the relative relationship of the elements is as written in the formula.

In one embodiment the E2B region is chimeric. That is, comprises DNA sequences from two or more different adenoviral serotypes. In one embodiment the E2B region has the sequence from 5068 bp to 10355 bp of SEQ ID NO: 1. In one embodiment the E2B is non-chimeric. In one embodiment the E2B region is a sequence other than 5068 bp to 10355 bp of SEQ ID NO: 1.

In one embodiment $B_A$ has the sequence from 3933 bp to 27184 bp of SEQ ID NO: 1.

E3 as employed herein refers to the DNA sequence encoding part or all of an adenovirus E3 region, it may be mutated such that the protein encoded by the E3 gene has conservative or non-conservative amino acid changes, such that it has the same function as wild-type (the corresponding wild-type protein); increased function in comparison to wild-type protein; decreased function, such as no function in comparison to wild-type protein or has a new function in comparison to wild-type protein or a combination of the same as appropriate. In one embodiment the E3 region is partially deleted. In one embodiment the E3 region can be replaced or interrupted by a transgene.

In one embodiment the E3 region in the viruses of the present disclosure comprise proteins independently selected from a human adenovirus or a combination of human adenoviruses, for example 1, 2, 3 or more.

In one embodiment the E3 proteins are selected from a group B virus, for example a group B virus independently selected from Ad11, Ad3 and combinations thereof.

E3 proteins in Ad11 include: 12.1K, 16.1K, 18.5K, 20.3K, 20.6K, 10.3K, 15.2K, 15.3K. In Ad11 the E3 region can be described as follows (no of nucleotides/ % of the whole genome; ORE; Position of ORF [nt] respectively):

| 26867-30625 (77.2-88) | 3759/10.8 | 12.1K | 27185-27502 |
| --- | --- | --- | --- |
| | | 16.1K | 27456-27851 |
| | | 18.5K | 27836-28336 |
| | | 20.3K | 28356-28901 |
| | | 20.6K | 28919-29482 |
| | | 10.3K | 29526-29801 |
| | | 15.2K | 29806-30210 |
| | | 15.3K | 30203-30610 |

The E3 proteins and structures of other group B viruses can readily be established or are already known to person skilled in the relevant art.

In one embodiment the E3 region corresponds to Ad11, in particular the full-length sequence from Ad11 E3 region.

Group C adenoviruses, for example Ad5 comprise a sequence in their E3 region encoding the adenovirus death protein (ADP) which is about 11.6 KDa. This protein is thought to have a function in cell lysis to allow the escape of the virus from the infected cell. Group B viruses do not use this mechanism to escape the cell.

In one embodiment an adenovirus according to the present disclosure, for example a group B virus, such as Ad11 or EnAd, comprises in the E3 region a sequence encoding an adenovirus death protein. Whilst not wishing to be bound by theory this protein may further augment the virus's ability to lyse cancer cells.

In one embodiment the adenovirus of the present disclosure is EnAd comprising a transgene in the E3 region. In one embodiment a transgene in the E3 region is under the control of an exogenous promoter. Exogenous promoters are discussed below.

In one embodiment where the genomic DNA is derived from Ad11 then where all E3 proteins are present then at least one protein encoded by that region will be from an adenovirus of a different serotype i.e. non-identical to an Ad11 E3 protein and/or the region will comprise further coding sequences.

In one embodiment the adenovirus of the present disclosure is EnAd, with an E3 region encoding one or more E3 proteins, for example a full-length E3 region encoding all the E3 proteins. In particular when the EnAd E3 region comprises orf1 and orf2 then the E3orf3 and orf8 fusion is absent or further genes/sequences are also present in the E3 region such as a transgene and/or at least one further E3 protein, for example a protein described herein.

In one embodiment the adenovirus is OvAd1 or OvAd2, as disclosed in WO2008/080003, with the E4orf4 region deleted and comprising a transgene in the E3 region and/or with an E3 region encoding one or more E3 proteins, for example a full-length E3 region encoding all the E3 proteins, for example all the E3 proteins from Ad11.

In one embodiment an adenovirus of the present disclosure (for example with a genomic sequence from Ad11, EnAd, OvAd1 and OvAd2) does not comprising E3orf1 and/or E3orf2 in the E3 region.

In one embodiment an adenovirus of the present disclosure (for example with a genomic sequence from Ad11, EnAd, OvAd1 and OvAd2) comprises an E3orf3 and orf8 fusion protein as shown in SEQ ID NO: 7.

In one embodiment an adenovirus of the present disclosure (for example with a genomic sequence from Ad11, EnAd, OvAd1 and OvAd2) does not comprise an E3orf3 and orf8 fusion protein as shown in SEQ ID NO: 7.

In one embodiment the $B_2$ comprises or consists of a DNA sequence encoding a 12.1K protein. In one embodiment the $B_2$ comprises or consists of a DNA sequence encoding a 16.1K protein. In one embodiment the $B_2$ comprises or consists of a DNA sequence encoding an 18.5K protein. In one embodiment the $B_2$ comprises or consists of a DNA sequence encoding a 20.3K protein. In one embodiment the $B_2$ comprises or consists of a DNA sequence encoding a 20.6K protein. In one embodiment the $B_2$ comprises or consists of a DNA sequence encoding a 10.3K protein. In one embodiment the $B_2$ comprises or consists of a DNA sequence encoding a 15.2K protein. In one embodiment the $B_2$ comprises or consists of a DNA sequence encoding a 15.3K protein. In one embodiment the $B_2$ comprises or consists of a DNA sequence encoding a 12.1K protein and one of 16.1K, 18.5K, 20.3K, 20.6K, 10.3K, 15.2K and 15.3K. In one embodiment the $B_2$ comprises or consists of a DNA sequence encoding a 16.1K protein and 18.5K, 20.3K, 20.6K, 10.3K, 15.2K and 15.3K. In one embodiment the $B_2$ comprises or consists of a DNA sequence encoding an 18.5K protein and any one of 20.3K, 20.6K, 10.3K, 15.2K, 15.3K. In one embodiment the $B_2$ comprises or consists of a DNA sequence encoding a 20.3K protein and any one of 20.6K, 10.3K, 15.2K and 15.3K. In one embodiment the $B_2$ comprises or consists of a DNA sequence encoding a 20.6K protein and any one of 10.3K, 15.2K and 15.3K. In one embodiment the $B_2$ comprises or consists of a DNA sequence encoding a 10.3K protein and any one of 15.2K and 15.3K. In one embodiment the $B_2$ comprises or consists of a DNA sequence encoding a 15.2K protein and 15.3K. In one embodiment $B_2$ comprises or consists of a DNA sequence encoding 1, 2, 3, 4, 5, 6, 7 or 8 E3 proteins.

Non-functional is defined below. In one embodiment non-functional in the E3 region as employed herein refers to an region or fragment, wherein a relevant function, for example down regulation of surface expression of MHC I molecules or inhibition of TNF-α-induced MCP-1 and/or IL-8 mRNA in U373 cells (see for example Lesokhin et al Journal of Virology August 2002 pa 8236-8243).

DNA sequence in relation to $B_X$ as employed herein refers to the DNA sequence in the vicinity of the 5' end of the L5 gene encoded in $B_B$. In the vicinity of or proximal to the 5' end of the L5 gene as employed herein refers to: adjacent (contiguous) to the 5' end of the L5 gene or a non-coding region inherently associated herewith i.e. abutting or contiguous to the 5' prime end of the L5 gene or a non-coding region inherently associated therewith. Alternatively, in the vicinity of or proximal to may refer to being close the L5 gene, such that there are no coding sequences between the $B_X$ region and the 5' end of L5 gene.

In one embodiment $B_X$ comprises the sequence of SEQ ID NO: 2. This sequence is a non-coding sequence wherein a DNA sequence, for example comprising a transgene (or transgene cassette), a restriction site or a combination thereof may be inserted therein. The insert(s) can occur anywhere within SEQ ID NO: 2 from the 5' end, the 3' end or at any point between bp 1 to 201.

In one embodiment $B_X$ comprises SEQ ID NO: 2 with a DNA sequence inserted, for example in equivalent or corresponding to an insert between positions 28192 bp & 28193 bp of SEQ ID NO: 1.

In one embodiment the insert is a restriction site insert. In one embodiment the restriction site insert comprises one or two restriction sites. In one embodiment the restriction site is a 19 bp restriction site insert comprising 2 restriction sites. In one embodiment the restriction site insert is a 9 bp restriction site insert comprising 1 restriction site. In one embodiment the restriction site insert comprises one or two restriction sites and at least one transgene, for example one or two transgenes. In one embodiment the restriction site is a 19 bp restriction site insert comprising 2 restriction sites and at least one transgene, for example one or two transgenes. In one embodiment the restriction site insert is a 9 bp restriction site insert comprising 1 restriction site and at least one transgene, for example one, two or three transgenes, such as one or two. In one embodiment the restriction site insert is SEQ ID NO: 5.

In one embodiment $B_X$ has the sequence from 28166 bp to 28366 bp of SEQ ID NO: 1. In one embodiment $B_X$ is a bond.

$B_B$ as employed herein refers to the DNA sequence encoding the L5 region. As employed herein the L5 region refers to the DNA sequence containing the gene encoding the fibre gene. The fibre gene encodes the fibre protein which is a major capsid component of adenoviruses. The fibre functions in receptor recognition and contributes to adenovirus' ability to selectively bind and infect cells.

The fibre can be from any adenovirus serotype and adenoviruses which are chimeric as result of changing the fibre for one of a different serotype are known. In present disclosure the fibre is from a group B virus, in particular Ad11, such as Ad11p.

In one embodiment $B_B$ has the sequence from 28367 bp to 29344 bp of SEQ ID NO: 1.

DNA sequence in relation to $B_Y$ as employed herein refer to the DNA sequence in the vicinity of the 3' end of the L5 gene encoded in $B_B$. In the vicinity of or proximal to the 3' end of the L5 gene as employed herein refers to: adjacent (contiguous) to the 3' end of the L5 gene or a non-coding region inherently associated herewith i.e. abutting or contiguous to the 3' prime end of the L5 gene or a non-coding region inherently associated therewith. Alternatively, in the vicinity of or proximal to may refer to being close the L5 gene, such that there are no coding sequences between the $B_Y$ region and the 3' end of the L5 gene.

In one embodiment $B_Y$ is located between the stop codon and polyA recognition site of gene L5 and the stop codon and polyA recognition site of the gene E4 represented by B3 in formula (I) and (Ia).

In one embodiment $B_Y$ comprises the sequence of SEQ ID NO: 3. This sequence is a non-coding sequence wherein a DNA sequence, for example of comprising a transgene (or transgene cassette), a restriction site or a combination thereof may be inserted. The insert(s) can occur anywhere within SEQ ID NO: 3 from the 5' end, the 3' end or at any point between bp 1 to 35.

In one embodiment $B_Y$ comprises SEQ ID NO: 3 with a DNA sequence inserted between positions bp 12 and 13 or a place corresponding to 29356 bp and 29357 bp in SEQ ID NO: 1. In one embodiment the insert is a restriction site insert. In one embodiment the restriction site insert comprises one or two restriction sites. In one embodiment the restriction site is a 19 bp restriction site insert comprising 2 restriction sites. In one embodiment the restriction site insert is a 9 bp restriction site insert comprising 1 restriction site. In one embodiment the restriction site insert comprises one or two restriction sites and at least one transgene, for example one or two or three transgenes, such as one or two. In one embodiment the restriction site is a 19 bp restriction site insert comprising 2 restriction sites and at least one transgene, for example one or two transgenes. In one embodiment the restriction site insert is a 9 bp restriction site insert comprising 1 restriction site and at least one transgene, for example one or two transgenes. In one embodiment the restriction site insert is SEQ ID NO: 4.

In one embodiment By has the sequence from 29345 bp to 29379 bp of SEQ ID NO: 1. In one embodiment $B_Y$ is a bond.

E4 as employed herein refers to the DNA sequence encoding part or all of an adenovirus E4 region, it may be mutated such that the protein encoded by the E4 gene has conservative or non-conservative amino acid changes, and has the same function as wild-type (the corresponding non-mutated protein); increased function in comparison to wild-type protein; decreased function, such as no function in comparison to wild-type protein or has a new function in comparison to wild-type protein or a combination of the same as appropriate.

The following is the open reading frame positions for Ad11p:

| | | | | | | |
|---|---|---|---|---|---|---|
| 34493-31808 | 2686/7.7 | ORF1 | 125R | | | 34413-34036 |
| (99.1-91.4) | | | 130R | ORF2 | | 33990-33601 |
| | | ORF3 | 117R | | | 33604-33251 |
| | | | 122R | ORF4 | | 33242-32874 |
| | | ORF5 | 299R | | | 32971-32072 |
| | | | 90R | ORF6 | | 32100-31825 |

In one embodiment the E4 region comprises a sequence independently selected from E4orf1, E4orf2, E4orf3, E4orf5, E4orf6 and combinations thereof including E4orf1 to E4orf6. In one embodiment the virus of the disclosure also comprises an E4orf4 region which consists of from 32188 bp to 29380 bp of SEQ ID NO: 1.

In the context of the present disclosure a characterising feature is lack of a functional E4orf4 region. Therefore, unless the context indicates otherwise use of E4 herein may refer to E4 with E4orf4 deleted or rendered non-functional. Deleted E4orf4 as employed herein refers to a deletion in part or all of the E4 region, for example comprising a deletion of at least 25 base pairs.

Non-functional as employed herein refers to a region that is at least partly present or, for example present in two or more non-continuous fragments, which do not have the same activity/functionality in the relevant respect as the "wild-type" full-length sequence.

Sequences with 10% or less function in comparison to the "wild-type" sequence will be considered non-function in the context of disclosures of the present application.

There are a number of routine ways to render E4orf4 non-functional, for example part of the region may be deleted to render it non-functional, the region may be disrupted by inserted a DNA sequence, and/or the region can be mutated to render it non-functional.

In one embodiment the lack of functionality refers to the inability to inactivate the AMPK pathway of energy sensing in a cancer cell. In one embodiment only E4orf4 is deleted in the E4 region. In one embodiment the E4 region has the sequence from 32188 bp to 29380 bp of SEQ ID NO: 1. In one embodiment $B_3$ has the sequence from 32188 bp to 29380 bp of SEQ ID NO: 1. E1A, E1B, E3 and E4 as employed herein each independently refer to the wild-type and equivalents thereof, mutated or partially deleted forms of each region as described herein.

Insert as employed herein refers to a DNA sequence that occurs either at the 5' end, the 3' end or within a given sequence such that it interrupts the sequence. In the context of the present disclosure inserts generally occur within either SEQ ID NO: 2 or SEQ ID NO: 3. An insert can be either a restriction site insert or a transgene cassette. When the sequence is interrupted the virus will still comprise the original sequence, but generally it will be as two fragments sandwiching the insert.

In one embodiment the insert is after bp 12 in SEQ ID NO: 3. In one embodiment the insert is at about position 29356 bp of SEQ ID NO: 1. In one embodiment the insert is a transgene cassette comprising one or more transgenes.

Transgenes

A DNA sequence may comprise one or more transgenes, for example, 1, 2, 3, 4 or 5 transgenes, such as 1 or 2. Transgene as employed herein refers to a gene that has been inserted into the genome sequence, which is a gene that is unnatural to the virus or not normally found in that particular location in the virus. Examples of transgenes are given below. Transgene as employed herein also includes a functional fragment of the gene that is a portion of the gene which when inserted is suitable to perform the function or most of the function of the full-length gene, such as at least 50% of the function.

Transgene and coding sequence are used interchangeably herein, unless the context indicates otherwise. Coding sequence as employed herein means a DNA sequence encoding a functional RNA, peptide, polypeptide or protein. Typically the coding sequence is cDNA of the transgene that encodes the functional RNA, peptide or protein of interest. Functional RNA, peptides and proteins of interest are described below. In one embodiment the transgene inserted encodes a human or humanised protein, polypeptide or peptide. In one embodiment the transgene inserted encodes a non-human protein, polypeptide or peptide (such as a non-human mammalian protein, polypeptide or peptide) and/or RNA molecule, for example from a mouse, rat, rabbit, camel, llama or similar.

In one embodiment transgene as employed herein refers to a segment of DNA containing a gene or cDNA sequence that has been isolated from one organism and is introduced into a different organism in this instance the adenovirus of the present disclosure. In one embodiment this non-native segment of DNA may retain the ability to produce functional RNA, peptide, polypeptide and/or protein.

A transgene cassette may comprise one or more transgenes, for example, 1, 2, 3, 4 or 5 transgenes, such as 1 or 2. Transgene cassette as employed herein refers to a DNA sequence encoding one or more transgenes in the form of one or more coding sequences and one or more regulatory elements.

A transgene cassette may encode one or more monocistronic and/or polycistronic mRNA sequences. In one embodiment the cassette encodes a monocistronic or polycistronic mRNA, for example the cassette is suitable for insertion into the adenovirus genome at a location under the control of an endogenous promoter or exogenous promoter or a combination thereof. Monocistronic mRNA as employed herein means an mRNA molecule encoding a single functional RNA, peptide, polypeptide or protein. In one embodiment the transgene cassette encodes monocistronic mRNA.

In one embodiment the transgene cassette in the context of a cassette encoding monocistronic mRNA refers to a segment of DNA optionally containing an exogenous promoter, which is a regulatory sequence that will determine where and when the transgene is active, or a splice site which is a regulatory sequence determining when an mRNA molecule will be cleaved by the spliceosome, a coding sequence (i.e. the transgene), usually derived from the cDNA for the protein of interest, optionally containing a polyA signal sequence and a terminator sequence.

In one embodiment the transgene cassette may encode one or more polycistronic mRNA sequences. Polycistronic mRNA as employed herein refers to an mRNA molecule encoding two or more functional RNA, peptides, polypeptides, proteins or a combination thereof. In one embodiment the transgene cassette encodes polycistronic mRNA.

Transgene cassette in the context of a cassette encoding polycistronic mRNA includes a segment of DNA optionally containing an exogenous promoter, which is a regulatory sequence that will determine where and when the transgene is active, or a splice site which is a regulatory sequence determining when a mRNA molecule will be cleaved by the spliceosome, two or more coding sequences (i.e. the transgenes), usually derived from the cDNA for the protein of interest. Generally each coding sequence is separated by either an IRES or a 2A peptide. Following the last coding sequence to be transcribed, the cassette may optionally contain a polyA sequence and a terminator sequence.

In one embodiment the transgene cassette encodes a monocistronic mRNA followed by a polycistronic mRNA. In another embodiment the transgene cassette encodes a polycistronic mRNA followed by a monocistronic mRNA.

In one embodiment the transgene cassette comprises a restriction site at each terminus. A restriction site is a location in a DNA sequence that can be cut by a restriction enzyme, usually an enzyme specific to the sequence.

In one embodiment the cassette is in the sense orientation. That is, is transcribed in a 5' to 3' direction. In one embodiment the cassette in the antisense orientation. That is, transcribed in the 3' to 5' orientation.

In one embodiment the transgene or transgene cassette does not comprise a non-biased inserting transposon, such as a TN7 transposon. In one embodiment the insert (or transgene) does not comprise a Tn7 transposon or part thereof. Tn7 transposon as employed herein refers to a non-biased insertion transposon as described in WO2008/080003.

Advantageously the transgene can be delivered intracellularly and can subsequently be transcribed and if appropriate translated. In one embodiment the entity encoded by the transgene when transcribed or translated in a cell, such as a cancer cell, increases danger signals on the cell. "Danger signals" as employed herein refers to a variety of molecules produced by cells undergoing injury, stress or non-apoptotic death which act as alarm signals by stimulating cells of the innate immune system to respond directly as well as serving to enhance activation of cells of the adaptive immune system.

It is known that the microenvironment of tumours often changes such that natural human immune responses are down regulated. Thus the ability to re-start the immune responses from within the tumour is potentially very interesting in the treatment of cancer. In one embodiment the coding sequence encodes a therapeutic RNA, therapeutic peptide, therapeutic polypeptide or therapeutic protein (i.e. is a therapeutic gene).

Therapeutic gene as employed herein means a gene that encodes an entity that may be useful in the treatment, amelioration or prevention of disease, for example the gene expresses a therapeutic protein, polypeptide, peptide and/or RNA, which at least slows down, halts or reverses the progression of a disease, such as cancer.

In one embodiment the transgene or transgenes encode a protein, polypeptide, peptide, RNA molecule. In one embodiment the functional RNA, peptide or protein, such as the antibody is released from the cell infected by the adenovirus, for example by active secretion or when cell lysis occurs.

In one embodiment the adenovirus lyses the cell, thereby releasing the functional RNA, peptide or protein, such as the antibody.

Advantageously, functional RNA, peptide or protein, such as antibodies expressed by adenoviruses of the present disclosure can be detected in tissue in vivo as both mRNA and antibody protein. Furthermore, the expressed functional RNA, peptide, polypeptide or protein, such as the antibody can bind its ligand in ELISA. Yet further, the functional RNA, peptide, polypeptide or protein, such as the antibody is detectable early (within 3 days of infection) and the expression is sustained over several weeks.

Advantageously, functional RNA, peptide or protein expression, such as antibody expression is sufficiently high to be able to detect the functional RNA, peptide or protein, such as the antibody in the blood.

In one embodiment adenoviruses of the present disclosure express functional RNA, peptide, polypeptide and/or protein, such as antibodies within about 3 days or more of infection, such as within about 36, 48, 60 or 72 hours, or such as 2, 3, 4, 5 or 6 days.

In one embodiment the encoded therapeutic peptide or protein is designed to be secreted into the extracellular environment. In one embodiment the functional RNA, peptide, polypeptide or protein, such as the antibody is released into the external microenvironment of the cell, for example into the culture supernatant, or in vivo: tissue, stroma, circulation, blood and/or lymphatic system. Leader sequence as employed herein refers to a polynucleotide sequence located between the promoter sequence and the coding region which can regulate gene expression at the level of transcription or translation.

In one embodiment the peptide, polypeptide or protein, encoded by the transgene, comprises a signal sequence. Signal peptide as employed herein refers to a short 13-36 residue peptide sequence located at the N-terminal of secretory proteins which is necessary for the entry of the protein into the secretory pathway for secretion or membrane expression.

In one embodiment, functional RNA, peptide, polypeptide or protein, such as antibodies expressed by the adenovirus of the present disclosure enter the blood stream.

In another embodiment the encoded therapeutic peptide or protein is designed to be expressed as a membrane-anchored form in the surface membrane of the cell, for example by including encoding a transmembrane domain in the protein or a site for attachment of a lipid membrane anchor.

In another embodiment the encoded therapeutic functional RNA, peptide or protein, such as an antibody is designed to be retained within the intact cell.

In one embodiment adenoviruses of the present disclosure express functional RNA, peptide or protein, such as antibodies for several weeks, for example about 1, 2, 3, 4, 5 or 6 weeks, such as 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41 or 42 days.

In one embodiment the encoded therapeutic proteins, polypeptides or peptides are target specific proteins or peptides.

Target specific proteins, polypeptides or peptides as employed herein refers to either the target proteins themselves, or different proteins, polypeptides or peptides that directly bind (for example are specific to the target) to or otherwise modify the levels of the target proteins or peptides. An example of the former would be a cytokine, whilst an example of the latter would be an antibody against that cytokine.

Target, depending on the context, also relates to mRNA or similar transcribed from the gene encoding the protein or polypeptide, which for example can be inhibited by RNAi type technology. Thus in the context of RNA, such as RNAi technology the target is the mRNA which is encoded by the gene of the target.

In one embodiment target refers to the protein or entity which is subject to biological intervention.

Targets of interest generally relate to particular cells, cellular products, antigens or signalling pathways associated with disease, particularly cancer.

Examples of targets of interest include, but are not limited to, stimulatory T-cell co-receptors and ligands thereto, checkpoint inhibitory T-cell co-receptor molecules and ligands thereto, receptors and ligands thereto expressed by regulatory T-cells, myeloid derived suppressor cells and immunosuppressive immune cells, dendritic cell and antigen-presenting cell receptors and ligands thereto, antigen processing and presentation mediators, cytokines and cytokine receptors, chemokines and chemokine receptors, transcription factors and regulators of transcription, intracellular trafficking molecules and regulators of cell function, tumour cell and tumour microenvironmental receptors and products, intracellular tumour cell enzymes such as IDO, antigens for recognition by immune cells.

Thus in one embodiment target as employed herein refers to a protein or polypeptide which can, for example be inhibited, neutralised or activated by, for example an antibody or binding fragment there, as appropriate. Target in the context of cytokines refers to a cytokine per se or an antibody or binding fragment thereof specific to the cytokine. Thus, the virus may encode and express the cytokine itself as release of thereof may stimulate "host" immune responses. In the context of ligands, mutated forms of the ligand can be encoded by the virus which compete with the natural ligand to bind the receptor. The mutated ligand may have increased binding affinity for the receptor, for example such that it has a slow off-rate thereby occupying the receptor and increasing or decreasing signalling therefrom. Alternatively, the activity of the mutated ligand may be reduced in comparison to the wild-type ligand, thereby reducing the binding and overall activity through the receptor from the natural ligand.

Examples of genetic material encoded by a transgene are DNA sequences capable of being expressed to provide various entities such as antibodies or binding fragments thereof, chemokines, cytokines, immunomodulators, enzymes for example capable of converting pro-drug in the active agent, or a DNA sequence capable of being transcribed into an RNAi molecule.

In one embodiment the coding sequence encodes functional RNA, for example therapeutic RNA. Functional RNA as employed herein refers to RNA which has a function other than to encode a protein or peptide and includes for examples include RNAi, such as shRNA and miRNA. shRNA as employed herein refers to short hairpin RNA which is a sequence of RNA that makes a tight hairpin turn that can be used to silence target gene expression via RNA interference (RNAi).

miRNA (microRNA) as employed herein refers to a small non-coding RNA molecule (containing about 22 nucleotides) which functions, via base-pairing with complementary sequences within mRNA molecules, to regulate gene expression at the transcriptional or post-transcriptional level. mRNA strands bound by miRNA are silenced because they can no longer be translated into proteins by ribosomes, and such complexes are often actively disassembled by the cell.

Functional RNA as employed herein refers to RNA which has a function other than to encode a protein or peptide and includes for examples include RNA constructs suitable for inhibiting or reducing gene activity, including RNAi, such as shRNA and miRNA. shRNA as employed herein refers to short hairpin RNA which is a sequence of RNA that makes a tight hairpin turn that can be used to silence target gene expression via RNA interference (RNAi). miRNA (micro-RNA) as employed herein refers to a small non-coding RNA molecule (containing about 22 nucleotides) which functions, via base-pairing with complementary sequences within mRNA molecules, to regulate gene expression at the transcriptional or post-transcriptional level. mRNA strands bound by miRNA are silenced because they can no longer be translated into proteins by ribosomes, and such complexes are often actively disassembled by the cell.

In one embodiment the virus or construct according to the present disclosure encodes a pro-drug, an immunomodulator and/or an enzyme.

Pro-drug as employed herein refers to a molecule that is administered as an inactive (or less than fully active) derivative that is subsequently converted to an active pharmacological agent in the body, often through normal metabolic processes. A pro-drug serves as a type of precursor to the intended drug. A pro-drug converting enzyme serves as the enzyme that converts a pro-drug to its pharmacologically active form.

Immunomodulator as employed herein refers to a modulator of immune response. Immunomodulators function in adjustment of the immune response to a desired level, as in immunopotentiation, immunosuppression, or induction of immunologic tolerance.

In one embodiment the protein encoded is an enzyme, for example a collagenase, a matrix metalloproteinase (such as MMP2 or 14), L-asparaginase or similar. Enzyme as employed herein refers to a substance that acts as a catalyst in living organisms, regulating the rate at which chemical reactions proceed without itself being altered in the process.

In one embodiment the peptide, polypeptide or protein encoded by a transgene is a mimotope. As employed herein a mimotope is a molecule, often a peptide, which mimics the structure of an epitope. The latter property causes an antibody response similar to the one elicited by the epitope. An antibody for a given epitope antigen will recognize a mimotope which mimics that epitope. Mimotopes are commonly obtained from phage display libraries through biopanning. Vaccines utilizing mimotopes are being developed. Thus antibodies of known specificity may be used to screen libraries (e.g peptide libraries in phage display—for example Ab sequence libraries or non-antibody peptide libraries, particularly those optimized for producing peptides with more stable 3D conformations)—Generation of mimotopes is well described in the art (see Tribbick G, Rodda S. Combinatorial methods for discovery of peptide ligands which bind to antibody-like molecules. J Mol Recognit. 2002 15(5):306-10; Masuko T, Ohno Y, Masuko K, Yagi H, Uejima S, Takechi M, Hashimoto Y. Towards therapeutic antibodies to membrane oncoproteins by a robust strategy using rats immunized with transfectants expressing target molecules fused to green fluorescent protein. Cancer Sci. 2011 102(1):25-35).

In one embodiment a mimotope or other designed vaccine antigens are encoded by a transgene and expressed in order to induce an antibody response in the recipient patient, wherein the antibodies induced have the desired therapeutic effect. In one embodiment GFP-peptide fusion proteins, with peptide sequences from desired human ligand, are used to induce anti-self target antibody responses, for example a peptide region of PD-L1 that is known to be important for binding to target molecule PD-1 may be genetically linked with GFP or other highly immunogenic foreign carrier proteins such that an immune antibody response to the peptide includes antibodies that cross-react with the native PDL1 molecule and thus serve to block PD-L1:PD-1 interactions in the same way as directly encoding an anti-PDL1 antibody would. Concepts for vaccines inducing ant-self therapeutic antibody responses are well described in the art (see Spohn G, Bachmann M F. Therapeutic vaccination to block receptor-ligand interactions. Expert Opin Biol Ther. 2003 3(3):469-76; Link A, Bachmann M F. Immunodrugs: breaking B- but not T-cell tolerance with therapeutic anticytokine vaccines. Immunotherapy 2010 2(4):561-74; Delavallee L, Assier E, Semerano L, Bessis N, Boissier M C. Emerging applications of anticytokine vaccines. Expert Rev Vaccines. 2008 7(10):1507-17).

The following is a non-exhaustive discussion of exemplary target specific peptides and proteins.

In one embodiment the target is one or more independently selected from the group comprising: OX40, OX40 ligand, CD27, CD28, CD30, CD40, CD40 ligand, CD70, CD137, GITR, 4-1 BB, ICOS or ICOS ligand, for example CD40 and CD40 ligand. In one embodiment the therapeutic intervention is achieved by an antibody or binding fragment specific to the target.

In one embodiment the transgene cassette encodes a ligand comprising CD40 or CD40 ligand, or an antibody, antibody fragment or shRNA targeted to CD40 or CD40 ligand. In one embodiment the adenovirus expresses a ligand comprising CD40 or CD40 ligand, or an antibody, antibody fragment or shRNA targeted to CD40 or CD40 ligand.

In one embodiment the target is one or more independently selected from the group comprising: CTLA-4, PD-1, PD-L1, PD-L2, VISTA, B7-H3, B7-H4, HVEM, ILT-2, ILT-3, ILT-4, TIM-3, LAG-3, BTLA, LIGHT or CD160, for example CTLA-4, PD-1, PD-L1 and PD-L2.

In one embodiment the transgene cassette encodes an antibody or antibody fragment specific to CTLA-4, PD-1, PD-L1 or PD-L2.

In one embodiment the adenovirus expresses an antibody or antibody fragment specific to CTLA-4, PD-1, PD-L1 or PD-L2.

In one embodiment the target is one or more independently selected from the group comprising CD16, CD25, CD33, CD332, CD127, CD31, CD43, CD44, CD162, CD301a, CD301b and Galectin-3. In one embodiment there is provided an antibody or binding fragment thereof specific thereto, for example a full-length antibody or a scFv.

In one embodiment the target is one or more independently selected from the group comprising: FLT-3, FLT-3 ligand, TLRs, TLR ligands, CCR7, CD1a, CD1c, CD11b, CD11c, CD80, CD83, CD86, CD123, CD172a, CD205, CD207, CD209, CD273, CD281, CD283, CD286, CD289, CD287, CXCR4, GITR Ligand, IFN-α2, IL-12, IL-23, ILT1, ILT2, ILT3, ILT4, ILT5, ILT7, TSLP Receptor, CD141, CD303, CADM1, CLEC9a, XCR1 and CD304. Certain TLR ligands have the ability to stimulate immune responses and, for example are employed as adjuvants. In one embodiment the virus encodes and secretes a TRL ligand. In one embodiment the target is CTIIA or GILT. In one embodiment the target is one or more independently selected from the group comprising: IL-1α, IL-1β, IL-6, IL-9, IL-12, IL-13, IL-17, IL-18, IL-22, IL-23, IL-24, IL-25, IL-26, IL-27, IL-33, IL-35. Interleukin-2 (IL-2), IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF.

In one embodiment the transgene cassette encodes an antibody or antibody fragment specific to IL-12, IL-18, IL-22, IL-7, IL-15, IL-21, IFNα, IFNγ, TNFα, TGFβ or lymphotoxin α (LTA). In one embodiment the adenovirus expresses IL-12, IL-18, IL-22, IL-7, IL-15, IL-21, IFNα, IFNγ, TNFα, TGFβ or lymphotoxin α (LTA).

In one embodiment the target is a chemokine, for example one or more independently selected from the group comprising: IL-8, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and CRTH2.

In one embodiment the transgene cassette encodes an antibody or antibody fragment specific to CCL5, CXCL9, CXCL12, CCL2, CCL19, CCL21, CXCR2, CCR2, CCR4 or CXCR4. In one embodiment the adenovirus expresses an antibody or antibody fragment specific to CCL5, CXCL9, CXCL12, CCL2, CCL19, CCL21, CXCR2, CCR2, CCR4 or CXCR4.

In one embodiment the target is one or more independently selected from the group comprising: STAT3, STAT1, STAT4, STAT6, CTIIA, MyD88 and NFκB family members.

In one embodiment the target is HSp70 or a regulator of cell survival and death such as survivin, for example the protein is targeted with an inhibitor, for example an antibody or bind fragment thereof, or mRNA transcribed from the relevant gene is inhibited by a mechanism, such as RNAi.

In one embodiment the target is one or more independently selected from the group comprising: amphiregulin, BTC, NRG1a, NRG1b, NRG3, TGFα, LRIG1, LRIG3, EGF, EGF-L6, Epigen, HB-EGF, EGFR, Her2, Her3 and Her4, for example the protein is targeted with an inhibitor, for example an antibody or bind fragment thereof, or mRNA transcribed from the relevant gene is inhibited by a mechanism, such as RNAi. In one embodiment the target is a ligand or receptor for one or more independently selected from the group comprising: hedgehog, FGF, IGF, Wnt, VEGF, TNF, TGFβ, PDGF and Notch.

In one embodiment the adenovirus expresses an antibody or antibody fragment specific to VEGF. In one embodiment the adenovirus expresses full length anti-human VEGF antibody. In one embodiment the expression of full length anti-human VEGF antibody is under the control of an endogenous promoter, such as the Major late promoter (MLP), in particular in position $B_Y$. In one embodiment the adenovirus expresses the scFv form of anti-human VEGF antibody. In one embodiment the expression of the scFv form of anti-human VEGF antibody is under the control of an endogenous promoter, such as the Major late promoter, in particular in position BY.

In one embodiment the target is IDO (Indoleamine-2,3-dioxygenase an immunosuppressive enzyme capable of inhibiting a destructive maternal T cell response).

In one embodiment the target is an antigen for recognition by immune cells for one or more proteins or peptides independently selected from the group comprising: immunogenic proteins from infectious organisms, such as cytomegalovirus antigens, influenza antigens, hepatitis B surface and core antigens, diphtheria toxoid, Crm197, tetanus toxoid; peptides derived from such antigens which are known T-cell or antibody epitopes, or genetically engineered composites or multimers of such antigens; tumour-derived proteins as antigens; peptides derived from such antigens which are known T-cell or antibody epitopes; and genetically engineered composites or multimers of such antigens for example WT1, MUC1, LMP2, idiotype, HPV E6&E7, EGFRvIII, HER-2/neu, MAGE A3, p53 nonmutant, p53 mutant, NY-ESO-1, GD2, PSMA, PCSA, PSA, gp100, CEA, MelanA/MART1, Ras mutant, proteinase3 (PR1), bcr-abl, tyrosinase, survivin, PSA, hTERT, particularly WT1, MUC1, HER-2/neu, NY-ESO-1, survivin or hTERT.

Protein ligand as employed herein refers to cell surface membrane or secreted proteins binding fragments thereof, that bind to or otherwise engage with the cellular receptors to influence the function of the cell, for example by stimulating intracellular signalling and modulating gene transcription within the cell. In one embodiment the protein expressed is engineered to be expressed on the surface of the cell and/or secreted from the cell.

In one embodiment the coding sequence encodes a reporter gene. Reporter gene or reporter sequence as employed herein means a gene or DNA sequence that produces a product easily detected in eukaryotic cells and may be used as a marker to determine the activity of another gene with which its DNA has been closely linked or combined. Reporter genes confer characteristics on cells or organisms expressing them that are easily identified and measured, or are selectable markers. Reporter genes are often used as an indication of whether a certain gene has been taken up by or expressed in the cell or organism population. Examples of common reporter genes include, but are not limited to, LacZ, luciferase, GFP, eGFP, neomycin phosphotransferase, chloramphenicol acetyltransferase, sodium iodide symporter, intracellular metalloproteins, HSV1-tk or oestrogen receptor.

In one embodiment the transgene is a reporter gene encoding, for example an imaging agent, such as luciferase, GFP or eGFP. In one embodiment the genetic material (in particular the transgene) does not encode or express a reporter gene such as an imaging agent, luciferase, GFP or eGFP.

The skilled person will appreciate that many possibilities exist for nucleic acid sequences that encode a given amino acid sequence due to codon redundancy, that silent nucleic acid base pair mutations are tolerated and all nucleic acid sequences that encode a given amino acid sequence as defined in any of the SEQ ID NO's are envisioned by the present disclosure.

In one or more embodiments the transgene employed encodes a sequence shown in any one of SEQ ID NO: 9 to 24, & 25-27.

In one embodiment the coding sequence encodes a peptide. Peptides as employed herein refers to an amino acid sequence of 50 amino acids or less, for example 5 to 20 amino acids, such as 6, 7, 8, 9, 10, 11, 12, 13, 14, 15, 16, 17, 18 and 19 amino acids, in particular a linear epitope which may be 7 or 8 amino acids in length.

In one embodiment the transgene encodes a protein. Protein and polypeptide as employed interchangeably herein and generally refer to an amino acid sequence of more than 50 amino acids. Generally proteins have a more complication secondary and tertiary structure than a polypeptide. Protein as employed herein includes a protein ligand, a protein receptor, or an antibody molecule.

As used herein "antibody molecule" includes antibodies and binding fragments thereof. Antibody as employed herein generally refers to a full length antibody and bispecific or multi-specific formats comprising the same.

Antibody-binding fragments includes an antibody fragment able to target the antigen with the same, similar or better specificity to the original "antibody" from which it was derived. Antibody fragments include: Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9): 1126-1136; Adair and Lawson, 2005, Drug Design Reviews-Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in international patent applications WO2005/003169, WO2005/003170 and WO2005/003171. Multi-valent antibodies may comprise multiple specificities e.g. bispecific or may be monospecific (see for example WO 92/22853, WO05/113605, WO2009/040562 and WO2010/035012).

Therapeutic antibody or antibody-binding fragment as employed herein refers to antibody or antibody-binding fragment which, when inserted in to the oncolytic virus, has a beneficial impact on a pathology in the patient, for example on the cancer being treated. Beneficial impact as employed herein refers to a desirable and/or advantageous effect of the antibody being expressed in vivo.

Suitable antibodies and antibody fragments may be agonistic or antagonistic and include those with anticancer activity and those which modify host cell responses to the cancer. For example, an antagonistic antibody or antibody fragment may increase or normalise vascularization of the tumour, whilst agonistic antibodies may render the host cell more visible to the host's innate and adaptive immune responses, for example by expressing antigens, danger signals, cytokines or chemokines to attract and activate the same, or by binding to co-stimulatory or checkpoint pathway molecules to enhance adaptive immune responses.

Classes of therapeutic antibodies and antibody-binding fragments include: anti-EGF antibodies, anti-VEGF antibodies, anti-PDGF antibodies and anti-FGF antibodies.

Registered therapeutic antibodies suitable for incorporation into viruses of the present disclosure include: abciximab, adalimumab, alemtzumab, basiliximab, belimumab, bevacizumab, brentuximab vedotin, canakinumab, cetuximab, certolzumab, daclizumab, denosumab, eculzumab, efalixumab, gemtuzumab, golimumab, ibritumomab tiuxetan, infliximab, ipilimumab, muromonab-CD3, ofatumumab, palivizumab, panitumumab, ranibizumab, rituximab, tocilizumab, tositumomab and trastuzumab.

In one embodiment antibodies of interest include those which are approved or in development for a cancer indication, for example trastuzumab, tositumomab, rituximab, panitumumab, ofatumumab, ipilimumab, ibritumomab tiuxetan, gemtuzumab, denosumab, cetuximab, brentuximab vedotin, avastin and adalimumab.

Specific as employed herein is intended to refer to an antibody or fragment that only recognises the antigen to which it is specific or to an antibody or fragment that has significantly higher binding affinity to the antigen to which is specific in comparison to its binding affinity to antigens to which it is not specific, for example 5, 6, 7, 8, 9, 10 times higher binding affinity.

Advantageously, the adenoviruses of the present disclosure can express full length and ScFv forms of antibodies.

In one embodiment the adenovirus expresses full length anti-human VEGF antibody.

In one embodiment the expression of full length anti-human VEGF antibody is under the control of an endogenous promoter, such as the Major late promoter (MLP).

In one embodiment the adenovirus expresses the ScFv form of anti-human VEGF antibody.

In one embodiment the expression of the ScFv form of anti-human VEGF antibody is under the control of an endogenous promoter, such as the Major late promoter.

In one embodiment the adenovirus expresses full length anti-human PD-L1 antibody.

In one embodiment the expression of full length anti-human PD-L1 antibody is under the control of an endogenous promoter, such as the Major late promoter (MLP).

In one embodiment the adenovirus expresses the ScFv form of anti-human PD-L1 antibody.

In one embodiment the expression of the ScFv form of anti-human PD-L1 antibody is under the control of an endogenous promoter, such as the Major late promoter. In one embodiment the sequence encoding the antibody or antibody fragment comprise or further comprises an internal ribosome entry sequence. Internal ribosome entry sequence (IRES) as employed herein means a nucleotide sequence that allows for translation initiation in the middle of a messenger RNA (mRNA) sequence.

In one embodiment the sequence encoding the antibody or antibody fragment further comprises a polyadenylation signal.

In one embodiment the antibody light chain comprises a CL domain, either kappa or lambda.

In one embodiment the coding sequence encodes an antibody heavy chain an antibody light chain or an antibody fragment.

In one embodiment the antibody is an anti-VEGF antibody. For example, such as Bevacizumab.

In one embodiment the antibody is a checkpoint inhibitor antibody, for example anti-PD-L1. Heavy chain (HC) as employed herein refers to the large polypeptide subunit of an antibody. Light chain (LC) as employed herein refers to the small polypeptide subunit of an antibody.

Thus in one embodiment the $B_Y$ represents a splice acceptor sequence (such as CAGG), a KOZAK sequence, a gene encoding a heavy chain of an antibody or fragment, a P2A sequence, a gene encoding a light chain sequence of antibody, and polyA tail. Various cassette designs are shown in FIG. 4.

Known antibodies or antibody-binding fragments can be employed to generate alternative antibody formats with the same CDRs or the same variable regions. For example, a full-length antibody can readily be converted into a Fab, Fab' or ScFv fragment.

A wide range of different forms of antibody may be employed in constructs of the present disclosure including antibody molecules from non-human animals, human antibody molecules, humanised antibody molecules and chimeric antibody molecules.

In one embodiment the antibody or binding fragment is monoclonal. Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

In one embodiment the antibody or binding fragment is non-human, i.e. completely from non-human origin. Advantageously, the viruses of the present disclosure allow the transgenes to be transported inside the cancerous cell. Thus, responses generated by the human patient to a non-human sequence (such as a protein) can be minimised by this intra-cellular delivery.

In one embodiment the antibody is chimeric, for example has human constant region(s) and non-human variable regions.

In one embodiment the antibody or binding fragment is human, i.e. from completely human origin.

In one embodiment the antibody or binding fragment is humanised. Humanised antibodies (which include CDR-grafted antibodies) are antibody molecules having one or more complementarity determining regions (CDRs) from a non-human species and a framework region from a human immunoglobulin molecule (see, for example U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply agonising activity or for target neutralization. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment the antibody light chain comprises a CL domain, either kappa or lambda. Antibodies for use in the present disclosure may be obtained using any suitable a method known in the art. The antigen polypeptide/protein including fusion proteins, including cells (recombinantly or naturally) expressing the polypeptide (such as activated T cells) can be used to produce antibodies which specifically recognise the antigen. The polypeptide may be the 'mature' polypeptide or a biologically active fragment or derivative thereof.

Polypeptides, for use to immunise a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The antigen polypeptide may in some instances be part of a larger protein such as a fusion protein for example fused to an affinity tag.

Antibodies generated against the antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunised. However, mice, rabbits, pigs and rats are generally most suitable.

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and International Patent Application number WO2004/106377.

Screening for antibodies can be performed using assays to measure binding to antigen and/or assays to measure the ability to antagonise the receptor. An example of a binding assay is an ELISA, in particular, using a fusion protein (optionally comprising a reporter), which is immobilized on plates, and employing a conjugated secondary antibody to detect anti-antigen antibody bound to the fusion protein.

Regulatory Elements

"Regulator of gene expression" (or regulator/regulatory element) as employed herein refers to a genetic feature, such as a promoter, enhancer or a splice acceptor sequence that plays a role in gene expression, typically by initiating or enhancing transcription or translation.

When under the control of an endogenous promoter, the cassette is inserted in the appropriate orientation to be under the control of said endogenous promoter. That is, where the promoter is generally on the antisense strand, the cassette is inserted in the antisense orientation. The cassette will generally comprise a splice acceptor sequence when under the control of an endogenous promoter.

Promoter as employed herein means a region of DNA that initiates transcription of a particular gene or genes. Promoters are generally located proximal to the genes they transcribe, on the same strand and upstream (i.e. 5') on the DNA. Proximal as employed in this context means sufficiently close to function as a promoter. In one embodiment the promoter is within 100 bp of the transcription start site.

Endogenous promoter as employed herein refers to a promoter that naturally occurs in (is native to) the adenovirus into which the transgene, is being inserted. In one or more embodiments the endogenous promoter employed is the naturally occurring promoter in the virus in its original location in the virus genome, in particular this is the primary or only promoter employed in the expression of the transgene or transgenes. In one embodiment the endogenous promoter used to promote the translation and optionally the transcription of the transgene is one resident, i.e. is one integrated in the genome of the adenovirus and not previously introduced by recombinant techniques.

The endogenous promoters in the virus can, for example, be utilised by employing a gene encoding a transgene and a splice acceptor sequence. Thus in one embodiment the coding sequence, for example the sequence encoding the antibody or antibody binding fragment further comprises a splice acceptor sequence.

In one embodiment an endogenous promoter is introduced into the viral genome at a desired location by recombinant techniques, for example is introduced in the transgene cassette.

In one embodiment the transgene, transgenes, or transgene cassette are under the control of an E4 promoter or a major late promoter.

Under the control of as employed herein means that the transgene is activated, i.e. transcribed, when a particular promoter dictates.

The Major Late Promoter (or MLP) as employed herein refers to the adenovirus promoter that controls expression of the "late expressed" genes, such as the L5 gene. The MLP is a "sense strand" promoter. That is, the promoter influences genes that are downstream of the promoter in the 5'-3' direction. The major late promoter as employed herein refers the original major late promoter located in the virus genome.

E4 promoter as employed herein refers to the adenovirus promoter of the E4 region. The E4 region is an antisense region; therefore the promoter is an antisense promoter. That is, the promoter is upstream of the E4 region in the 3'-5' direction. Therefore any transgene cassette under control of the E4 promoter must be oriented appropriately. In one embodiment the cassette under the control of the E4 promoter is in the antisense orientation. The E4 promoter as employed herein refers to the original E4 promoter located in the virus genome.

Thus in one embodiment there is provided a replication competent oncolytic adenovirus serotype 11 or virus-derivative thereof wherein the fibre, hexon and capsid are serotype 11, wherein the virus genome comprises a DNA sequence encoding a therapeutic antibody or antibody-binding fragment, said DNA sequence under the control of a promoter endogenous to the adenovirus selected from consisting of E4 and the major late promoter (i.e. the E4 promoter or the major late promoter), such that the transgene does not interfere with virus replication, for example located after L5 in the virus genome.

Typically, when under the control of an endogenous promoter, the coding sequence will be immediately preceded by a KOZAK sequence. That is when the coding region initiation codon (AUG) is in the context of the sequence (gcc)gccRccAUGG (SEQ ID NO: 11) that plays a major role in the initiation of translation, wherein a lower case letter denotes the most common base at a position where the base can nevertheless vary; upper case letters indicate highly-conserved bases, i.e. the 'AUGG' sequence (SEQ ID NO: 12) is constant or rarely, if ever, changes; 'R' indicates that a purine (adenine or guanine) is always observed at this position and the sequence in brackets (gcc) is of uncertain significance. Thus in one embodiment the initiation codon AUG is in the context of the consensus KOZAK sequence.

In one embodiment the transgene cassette comprises an exogenous promoter. Exogenous promoter as employed herein refers to a promoter that is not naturally occurring in the adenovirus into which the transgene is being inserted. Typically exogenous promoters are from other viruses or are mammalian promoters. Exogenous promoter as employed herein means a DNA element, usually located upstream of the gene of interest, that regulates the transcription of the gene.

In one embodiment the regulator of gene expression is an exogenous promoter, for example CMV (cytomegalovirus promoter), CBA (chicken beta actin promoter) or PGK (phosphoglycerate kinase 1 promoter), such as CMV.

In one embodiment there is provided a replication competent oncolytic adenovirus serotype 11 or virus-derivative thereof wherein the fibre, hexon and capsid are serotype 11, wherein the virus genome comprises a DNA sequence encoding a therapeutic antibody or antibody-binding fragment located in a part of the virus genome which is expressed late in the virus replication cycle and such that the transgene does not interfere with virus replication, wherein said DNA sequence under the control of a promoter exogenous to the adenovirus (for example the CMV promoter).

In one embodiment the exogenous promoter is an antigen-presenting cell promoter. Antigen-presenting cell promoter as employed herein refers to a promoter for a gene that is selectively expressed by antigen-presenting cells, such as dendritic cells or macrophages. Such genes include but are not limited to: FLT-3, FLT-3 ligand, TLRs, CD1a, CD1c, CD11b, CD11c, CD80, CD83, CD86, CD123, CD172a, CD205, CD207, CD209, CD273, CD281, CD283, CD286, CD289, CD287, CXCR4, GITR Ligand, IFN-α2, IL-12, IL-23, ILT1, ILT2, ILT3, ILT4, ILT5, ILT7, TSLP Receptor, CD141, CD303, CADM1, CLEC9a, XCR1 or CD304; antigen processing and presentation mediators such as CTIIA or GILT. Thus in one embodiment the exogenous promoter is suitable for expression of said genes.

In one embodiment an mRNA or each mRNA is/are terminate in a polyadenylation signal sequence, such as typically terminates an mRNA sequence, for example as shown in SEQ ID NO: 6. Thus one embodiment the transgene or the transgene cassette comprises at least one sequence encoding a polyadenylation signal sequence.

"PolyA", "Polyadenylation signal" or "polyadenylation sequence" as employed herein means a DNA sequence, usually containing an AATAAA site, that once transcribed can be recognised by a multiprotein complex that cleaves and polyadenylates the nascent mRNA molecule. In one embodiment the polyadenylation sequence has the nucleotide sequence of SEQ ID NO: 6.

In one embodiment the construct does not include a polyadenylation sequence. In one embodiment the regulator of gene expression is a splice acceptor sequence.

"Splice acceptor sequence", "splice acceptor" or "splice site" as employed herein refers to a regulatory sequence determining when an mRNA molecule will be recognised by small nuclear ribonucleoproteins of the spliceosome complex. Once assembled the spliceosome catalyses splicing between the splice acceptor site of the mRNA molecule to an upstream splice donor site producing a mature mRNA molecule that can be translated to produce a single polypeptide or protein.

Different sized splice acceptor sequences may be employed in the present invention and these can be described as short splice acceptor (small), splice acceptor (medium) and branched splice acceptor (large).

SSA as employed herein means a short splice acceptor, typically comprising just the splice site. SA as employed herein means a splice acceptor, typically comprising the short splice acceptor and the polypyrimidine tract. bSA as employed herein means a branched splice acceptor, typically comprising the short splice acceptor, polypyrimidine tract and the branch point. In one embodiment the splice acceptor sequence is selected from the group comprising: tgctaatctt cctttctctc ttcagg (SEQ ID NO: 30); tttctctctt cagg (SEQ ID NO: 31), and cagg.

In one embodiment the regulatory element is or comprises a KOZAK sequence, for example a splice site may be immediately proceeded or immediately followed by (i.e. followed in a 5' to 3' direction) by a consensus KOZAK sequence (for example CCACC). In one embodiment the splice site and the Kozak sequence are separated by 100 or less bp, for example 0-50 base pairs, such as 10, 15, 20, 25, 30, 35, 40 or 45 base pairs.

In one embodiment the splice acceptor sequence is followed by the KOZAK sequence, for example the two regulatory elements are in tandem In one embodiment the regulatory element is or comprises an Internal Ribsome Entry sequence. IRES as employed herein means a nucleotide sequence that allows for translation initiation in the middle of a messenger RNA (mRNA) sequence. This is particularly useful when the cassette encodes polycistronic mRNA. Using an IRES results in a polycistronic mRNA that is translated into multiple individual proteins or peptides. In one embodiment a particular IRES is only used once in the genome. This may have benefits with respect to stability of the genome.

In one embodiment the regulatory element is or comprises a "High self-cleavage efficiency 2A peptide" or "2A peptide" which as employed herein refers to a peptide which is efficiently cleaved following translation. Suitable 2A peptides include P2A, F2A, E2A and T2A. The redundancy in the DNA code may be utilised to generate a DNA sequence that is translated into the same 2A peptide. Using 2A peptides is particularly useful when the cassette encodes polycistronic mRNA. Using 2A peptides results in a single polypeptide chain being translated which is modified post-translation to generate multiple individual proteins or peptides.

The skilled person will appreciate that many possibilities exist for nucleic acid sequences that encode a given amino acid sequence due to codon redundancy, that silent nucleic acid base pair mutations are tolerated and all nucleic acid sequences that encode a given amino acid sequence as defined in any of the SEQ ID NO's are envisioned by the present disclosure.

In one embodiment the adenovirus of the present disclosure is an oncolytic virus which has an enhanced therapeutic index for cancer cells.

Viruses according to the present disclosure can be investigated for their preference for a specific tumour type by examination of its lytic potential in a panel of tumor cells, for example colon tumor cell lines include HT-29, DLD-1, LS174T, LS1034, SW403, HCT116, SW48, and Colo320DM. Any available colon tumour cell lines would be equally useful for such an evaluation. Prostate cell lines include DU145 and PC-3 cells. Pancreatic cell lines include Panc-1 cells. Breast tumour cell lines include MDA231 cell line and ovarian cell lines include the OVCAR-3 cell line. Hemopoietic cell lines include, but are not limited to, the Raji and Daudi B-lymphoid cells, K562 erythroblastoid cells, U937 myeloid cells, and HSB2 T-lymphoid cells. Other available tumour cell lines are equally useful.

Formulations

The present disclosure relates also extends to compositions comprising the virus of the disclosure, for example a pharmaceutical formulation of a virus as described herein.

In one embodiment there is provided a liquid parenteral formulation, for example for infusion or injection, of a replication capable oncolytic according to the present disclosure wherein the formulation provides a dose in the range of $1 \times 10^{10}$ to $1 \times 10^{14}$ viral particles per volume of dose. Parenteral formulation means a formulation designed not to be delivered through the GI tract. Typical parenteral delivery routes include injection, implantation or infusion. In one embodiment the formulation is provided in a form for bolus delivery.

In one embodiment the parenteral formulation is in the form of an injection. Injection includes intravenous, subcutaneous, intra-tumoral or intramuscular injection. Injection as employed herein means the insertion of liquid into the body via a syringe. In one embodiment the method of the present disclosure does not involve intra-tumoral injection.

In one embodiment the parenteral formulation is in the form of an infusion.

Infusion as employed herein means the administration of fluids at a slower rate by drip, infusion pump, syringe driver or equivalent device. In one embodiment the infusion is administered over a period in the range of 1.5 minutes to 120 minutes, such as about 3, 4, 5, 6, 7, 8, 9, 10, 11, 12, 13, 14 15, 16, 17, 18, 19 20, 25, 30, 35, 40, 45, 50, 55, 60, 65, 70, 65, 80, 85, 90, 95, 100, 105, 110 or 115 minutes.

In one embodiment one dose of the formulation less than 100 mls, for example 30 mls, such as administered by a syringe driver.

In one embodiment the injection is administered as a slow injection, for example over a period of 1.5 to 30 minutes.

In one embodiment the formulation is for intravenous (i.v.) administration. This route is particularly effective for delivery of oncolytic virus because it allows rapid access to the majority of the organs and tissue and is particular useful for the treatment of metastases, for example established metastases especially those located in highly vascularised regions such as the liver and lungs.

Therapeutic formulations typically will be sterile and stable under the conditions of manufacture and storage. The composition can be formulated as a solution, microemulsion, liposome, or other parenteral formulation suitable for administration to a human and may be formulated as a pre-filled device such as a syringe or vial, particular as a single dose.

The formulation will generally comprise a pharmaceutically acceptable diluent or carrier, for example a non-toxic, isotonic carrier that is compatible with the virus, and in which the virus is stable for the requisite period of time.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a dispersant or surfactant such as lecithin or a non-ionic surfactant such as polysorbate 80 or 40. In dispersions the maintenance of the required particle size may be assisted by the presence of a surfactant. Examples of isotonic agents include sugars, polyalcohols such as mannitol, sorbitol, or sodium chloride in the composition.

In one embodiment parenteral formulations employed may comprise on or more of the following a buffer, for example 4-(2-hydroxyethyl)-1-piperazineethanesulfonic acid, a phosphate buffer and/or a Tris buffer, a sugar for example dextrose, mannose, sucrose or similar, a salt such as sodium chloride, magnesium chloride or potassium chloride, a detergent such as a non-ionic surfactant such as briji, PS-80, PS-40 or similar. The formulation may also comprise a preservative such as EDTA or ethanol or a combination of EDTA and ethanol, which are thought to prevent one or more pathways of possible degradation.

In one embodiment the formulation will comprise purified oncolytic virus according to the present disclosure, for example $1 \times 10^{10}$ to $1 \times 10^{14}$ viral particles per dose, such as $1 \times 10^{10}$ to $1 \times 10^{12}$ viral particles per dose.

In one embodiment the concentration of virus in the formulation is in the range $2 \times 10^{8}$ to $2 \times 10^{14}$ vp/mL, such as $2 \times 10^{12}$ vp/ml.

In one embodiment the parenteral formulation comprises glycerol.

In one embodiment the formulation comprises oncolytic adenovirus as described herein, HEPES (N-2-hydroxyethylpiperazine-N'-2-ethanesulfonic acid), glycerol and buffer.

In one embodiment the parenteral formulation consists of virus HEPES for example 5 mM, glycerol for example 5-20% (v/v), hydrochloric acid, for example to adjust the pH into the range 7-8 and water for injection.

In one embodiment 0.7 mL of ColoAd1 at a concentration of $2\times10^{12}$ vp/mL is formulated in 5 mM HEPES, 20% glycerol with a final pH of 7.8.

A comprehensive discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure will generally contain a virus as described herein with a physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the carrying the virus is of primary importance and thus in one embodiment the virus according to the present disclosure may be adsorbed or absorbed onto a particle, such as a lactose particle of the given size.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The above-mentioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant gas-containing inhalable aerosols may also contain other ingredients, such as cosolvents, stabilisers, surface-active agents (surfactants), antioxidants, lubricants and means for adjusting the pH. All these ingredients are known in the art.

The propellant gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The virus of the invention can be delivered dispersed in a solvent, e.g. in the form of a solution or a suspension, for example as already described above for parenteral formulations. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

In a further aspect the present disclosure extends to a virus or a formulation thereof as described herein for use in treatment, in particular for the treatment of cancer. In one embodiment the method of treatment is for use in the treatment of a tumour.

Tumour as employed herein is intended to refer to an abnormal mass of tissue that results from excessive cell division that is uncontrolled and progressive, also called a neoplasm. Tumours may be either benign (not cancerous) or malignant. Tumour encompasses all forms of cancer and metastases.

In one embodiment the tumour is a solid tumour. The solid tumour may be localised or metastasised.

In one embodiment the tumour is of epithelial origin.

In one embodiment the tumour is a malignancy, such as colorectal cancer, hepatoma, prostate cancer, pancreatic cancer, breast cancer, ovarian cancer, thyroid cancer, renal cancer, bladder cancer, head and neck cancer or lung cancer.

In one embodiment the tumour is a colorectal malignancy. Malignancy as employed herein refers to cancerous cells.

In one embodiment the oncolytic adenovirus is employed in the treatment or prevention of metastasis. In one embodiment the virus or formulation herein is employed in the treatment of drug resistant cancers.

In one embodiment the virus is administered in combination with the administration of a further cancer treatment or therapy.

In one embodiment there is provided a virus or formulation according to the present disclosure for use in the manufacture of a medicament for the treatment of cancer, for example a cancer described above.

In a further aspect there is provide a method of treating cancer comprising administering a therapeutically effective amount of a virus or formulation according to the present disclosure to a patient in need thereof, for example a human patient.

In one embodiment the oncolytic virus or formulation herein is administered in combination with another therapy.

"In combination" as employed herein is intended to encompass where the oncolytic virus is administered before, concurrently and/or post cancer treatment or therapy.

Cancer therapy includes surgery, radiation therapy, targeted therapy and/or chemotherapy. Cancer treatment as employed herein refers to treatment with a therapeutic compound or biological agent, for example an antibody intended to treat the cancer and/or maintenance therapy thereof. In one embodiment the cancer treatment is selected from any other anti-cancer therapy including a chemotherapeutic agent, a targeted anticancer agent, radiotherapy, radio-isotope therapy or any combination thereof.

The oncolytic adenovirus may be used as a pre-treatment to the therapy, such as a surgery (neoadjuvant therapy), to shrink the tumour, to treat metastasis and/or prevent metastasis or further metastasis. The oncolytic adenovirus may be used after the therapy, such as a surgery (adjuvant therapy), to treat metastasis and/or prevent metastasis or further metastasis. Concurrently as employed herein is the administration of the additional cancer treatment at the same time or approximately the same time as the oncolytic adenovirus formulation. The treatment may be contained within the same formulation or administered as a separate formulation.

In one embodiment the virus is administered in combination with the administration of a chemotherapeutic agent.

Chemotherapeutic agent as employed herein is intended to refer to specific antineoplastic chemical agents or drugs that are selectively destructive to malignant cells and tissues. For example, alkylating agents, antimetabolites, anthracyclines, plant alkaloids, topoisomerase inhibitors, and other antitumour agents. Other examples of chemotherapy include doxorubicin, 5-fluorouracil (5-FU), paclitaxel, capecitabine, irinotecan, and platins such as cisplatin and oxaliplatin. The preferred dose may be chosen by the practitioner based on the nature of the cancer being treated.

In one embodiment the therapeutic agent is ganciclovir, which may assist in controlling immune responses and/or tumour vasculation.

In one embodiment one or more therapies employed in the method herein are metronomic, that is a continuous or frequent treatment with low doses of anticancer drugs, often given concomitant with other methods of therapy.

Subgroup B oncolytic adenoviruses, in particular Ad11 and those derived therefrom such as ColoAd1 may be particularly synergistic with chemotherapeutics because they seem to have a mechanism of action that is largely independent of apoptosis, killing cancer cells by a predominantly necrolytic mechanism. Moreover, the immunosuppression that occurs during chemotherapy may allow the oncolytic virus to function with greater efficiency.

Therapeutic dose as employed herein refers to the amount of oncolytic adenovirus that is suitable for achieving the intended therapeutic effect when employed in a suitable treatment regimen, for example ameliorates symptoms or conditions of a disease. A dose may be considered a therapeutic dose in the treatment of cancer or metastases when the number of viral particles may be sufficient to result in the following: tumour or metastatic growth is slowed or stopped, or the tumour or metastasis is found to shrink in size, and/or the life span of the patient is extended. Suitable therapeutic doses are generally a balance between therapeutic effect and tolerable toxicity, for example where the side-effect and toxicity are tolerable given the benefit achieved by the therapy.

Thus there is provided a replication competent oncolytic adenovirus serotype 11 or virus-derivative thereof wherein the fibre, hexon and capsid are serotype 11, wherein the virus genome comprises a DNA sequence encoding a therapeutic antibody or antibody-binding fragment, wherein said DNA sequence is under the control of a promoter endogenous to the adenovirus selected from the group consisting of the E4 and the major late promoter, such that the transgene does not interfere with virus replication.

In one embodiment there is provide a replication competent oncolytic adenovirus serotype 11 or virus-derivative thereof wherein the fibre, hexon and capsid are serotype 11, wherein the virus genome comprises a DNA sequence encoding a therapeutic antibody or antibody-binding fragment located in a part of the virus genome which is expressed late in the virus replication cycle and such that the transgene does not interfere with virus replication, wherein said DNA sequence under the control of a promoter exogenous to the adenovirus.

Advantageously, when under the control of these promoters the virus remains replication competent and is also able to express the antibody as a full length antibody or a suitable binding fragment. Thus the antibody of choice will be expressed inside the cancer cell.

Employing an endogenous promoter may be advantageous because it reduces the size of the transgene cassette that needs to be incorporated to express the antibody or fragment, i.e. the cassette can be smaller because no exogenous promoter needs to be included.

Employing an endogenous promoter in the virus may also be advantageous in a therapeutic context because the transgene is only expressed when the virus is replicating as opposed to a constitutive exogenous promoter which will continually transcribe the transgene and may lead to an inappropriate concentration of the antibody or fragment. The latter may cause undesirable side-effects and therefore may be a safety issue or at least be difficult to control.

In one embodiment expression of the antibody or fragment is under the control of the major late promoter.

In one embodiment the expression of the antibody or fragment is under the control of the E4 promoter.

In one embodiment the DNA sequence encoding the antibody or fragment is located after the L5 gene in the virus sequence.

Employing an exogenous promoter may be advantageous because it can strongly and constitutively express the antibody or fragment, which may be particularly useful in some situations, for example where the patient has very pervasive cancer.

In one embodiment expression of the antibody or fragment is under the control of a CMV promoter.

In one embodiment the DNA sequence encoding the antibody or fragment is located after the L5 gene in the virus sequence. In one embodiment the exogenous promoter is associated with this DNA sequence, for example is part of the expression cassette encoding the antibody or fragment.

In one embodiment the antibody variable regions of an antibody or antibody fragment employed are between 95 and 100% similar or identical to the variable regions of bevacizumab (also known as Avastin®), such as 96, 97, 98 or 99% similar or identical.

The skilled person will appreciate that the armed adenovirus genome can be manufactured by other technical means, including entirely synthesising the genome. The skilled person will appreciate that in the event of synthesising the genome the region of insertion may not comprise the restriction site nucleotides that will be found following insertion of genes using cloning methods.

In one embodiment the armed adenovirus genome is entirely synthetically manufactured.

The disclosure herein further extends to an adenovirus of formula (I) or a subformula thereof, obtained or obtainable from inserting a transgene or transgene cassette. In the context of this specification "comprising" is to be interpreted as "including".

Embodiments of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference. Any embodiments specifically and explicitly recited herein may form the basis of a disclaimer either alone or in combination with one or more further embodiments.

BRIEF DESCRIPTION OF THE FIGURES

FIG. 3 Shows the cytopathic effect in EnAd or NG-184 cell monolayers 48 hrs post-infection with 330 ppc (upper panels). To achieve a similar cytopathic effect to EnAd 1650 ppc of NG-184 were used (lower panel).

FIG. 4 Shows various transgene cassette designs.

SEQUENCES: 1 EnAd genome, 2 A non-coding sequence suitable for inclusion into $B_X$, 3 A non-coding sequence suitable for inclusion into $B_Y$, 4 & 5 A restriction site, 6 A polyadenylation sequence, 7 The E3 region from EnAd, 8 The E2B region from EnAd, 9 Anti-VEGF ab VH chain, 10 Anti-PD-L1 antibody VH chain, 11 Anti-VEGF ab VL chain, 12 Anti-PD-L1 antibody VL chain amino acid sequence, 13 Human IgG1 constant heavy chain, 14 Human IgG1 modified constant heavy chain, 15 Human kappa constant light chain, 16 Anti-VEGF scFv amino acid sequence, 17 Anti-PD-L1 ScFv, 18 GFP, 19 Luciferase, 20 Human Tumour necrosis factor alpha, 21 Human Interferon gamma, 22 Human Interferon alpha, 23 NY-ESO-1, 24 Human MUC-1, 25 Sodium Iodide symporter, 26 Anti-CTLA-4 VH chain, 27 Anti-CTLA-4 VL, 28 NG-184 genome, 29 NG-186 genome, and 30 & 31 splice acceptor.

EXAMPLES

Example 1: Synthesis of Chimeric Ad11p: EnAd Viral Genomes

To investigate the properties of the changes in the E2B and E4 regions of the EnAd genome compared to the parental genome, Ad11p, two chimeric Ad11p:EnAd viral genomes were designed and generated synthetically by Gibson Assembly methods (SGI DNA, La Jolla, Calif.) The first synthetic genome, designated NG-184, consists of the EnAd genome, including the EnAd chimeric E2B region (black), but has the E4 region of the parental virus Ad11p (black with hatched white lines). As such the 25 bp deletion present in EnAd E4orf4 (black) is no longer present in this virus; the virus produces an intact Ad11p E4orf4 protein.

The second synthetic genome, designated NG-186, consists of the EnAd viral genome but has the E2B region of the parental virus Ad11p (black with hatched white lines). As such the chimeric Ad11p/Ad3 E2B gene region of this virus has been entirely replaced with the Ad11p E2B gene region, but this virus retains the 25 bp deletion in E4orf4

Figure 1:
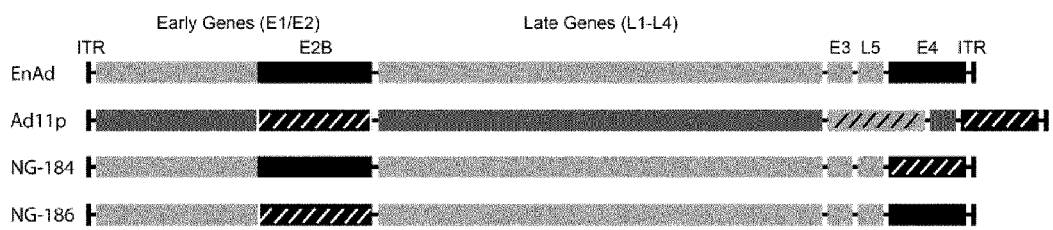
FIG. 1 Shows schematics of EnAd, Ad11p, NG-184 and NG-186 genomes

Schematics of the genomes of EnAd, Ad11p, NG-184 and NG-186 genomes are shown in FIG. 1.

Example 2: Characterisation of the Effect of EnAd E2B and E4 Region Alterations Compared to EnAd or Ad11p on Virus Growth and Particle Production Virus Purification:

EnAd, NG-184 or NG-186 genomes were purified by phenol/chloroform extraction. The extracted DNA was then precipitated for 16 hrs, −20° C. in 300 µl>95% molecular biology grade ethanol and 10 µl 3M Sodium Acetate.

The precipitated DNA was pelleted by centrifuging at 14000 rpm, 5 mins and was washed in 500 µl 70% ethanol, before centrifuging again, 14000 rpm, 5 mins. The clean DNA pellet was air dried, resuspended in 500 µl OptiMEM containing 15 µl lipofectamine transfection reagent and incubated for 30 mins, RT. The transfection mixture was then added to 293 cells which were then incubated at 37° C., 5% $CO_2$.

Figure 2A:
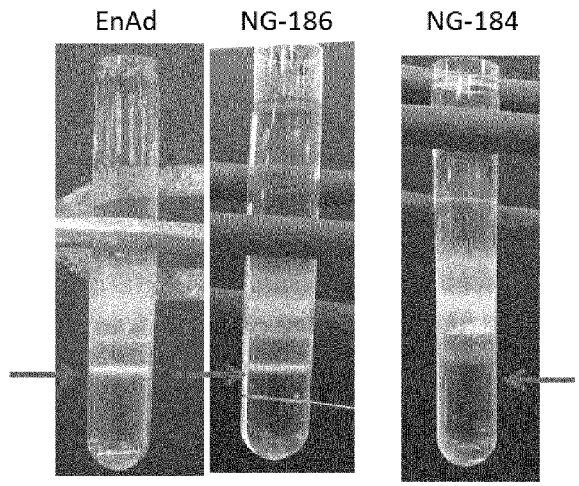
FIG. 2A Shows photographs of complete virus particle bands on a CsCl gradient. The positions of the bands are shown with an arrow, and the expected position of the complete band for NG-184 is also shown.
Figure 2B:
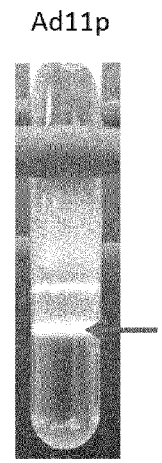
FIG. 2B Shows a photograph of a complete virus particle band on a CsCl gradient for Ad11p.

The production of virus was monitored by observation of a significant cytopathic effect (CPE) in the cell monolayer. Once extensive CPE was observed the virus was harvested from 293 cells by three freeze-thaw cycles. All three viruses, EnAd, NG-184 and NG-186 showed significant CPE within 1-2 weeks post transfection and harvested material was therefore used to re-infect 293 cells in order to amplify the virus stocks. These virus stocks were then used in one further amplification step and purification by caesium chloride banding was attempted. During this final amplification step EnAd, NG-184 and NG-186 showed significant CPE before harvesting, however, complete virus particles could only be detected during CsCL banding for EnAd and NG-186 infected cells (FIG. 2A). Repeat of this process and comparison to historical data to Ad11p (FIG. 2B) confirmed that while EnAd, Ad11p and NG-186 can all yield enough intact virus particles from the virus production process to form a defined band on the gradient, NG-184 infection is unable to do this.

Figure 2C:
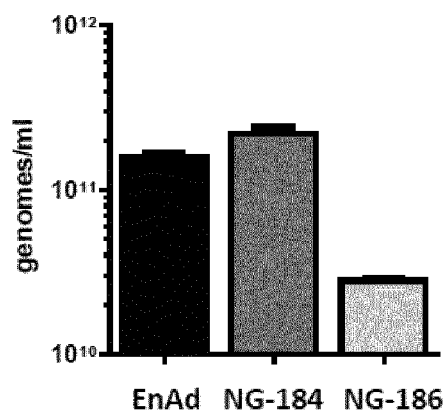
FIG. 2C Shows the total genomes produced/ml of harvested material following infection for 48 hrs of 293 cells with either EnAd, NG-184 or NG-186.
Figure 2D:
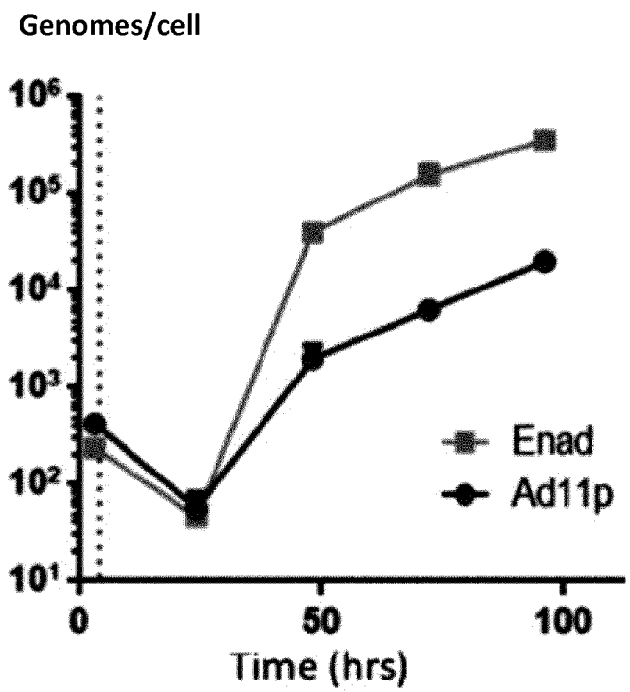
FIG. 2D Shows total genomes produced per cell for EnAd or Ad11p during a tumour cell infection.
Figure 2E:
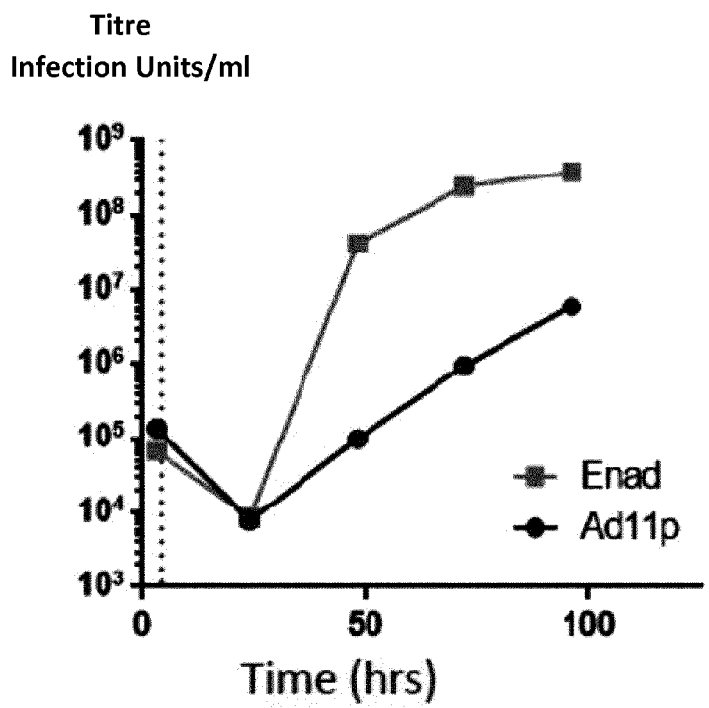
FIG. 2E. Shows relative infectious virus particle titre produced from EnAd or Ad11p infected tumour cells during infection.

Virus Replication (qPCR):

To determine if this difference in ability to produce functional virus particles could be linked to virus replication, EnAd, NG-184 and NG-186 seed stocks were used to infect 293 cells for 48 hrs and then the supernatants and cells harvested to assess total genome production during infection. Virus material was harvested from infected cells and supernatant using three freeze-thaw cycles. Total DNA was then extracted from the lysed stocks using the Sigma Genelute DNA extraction Kit, according to the manufacturer's protocol. A standard curve using EnAd virus particles ($2.5 \times 10^{10}$ to $2.5 \times 10^5$ vp) was also prepared and extracted using the Sigma Genelute Kit. Each extracted sample or standard was analysed by qPCR using an EnAd E3 gene specific primer-probe set Quantification of the number of detected virus genomes per cell demonstrated that viruses encoding the EnAd E2B region (both EnAd and NG-184) produced similar levels of total genomes in the 293 cell line. NG-186, which contains the Ad11p E2B region, produced a lower level of total genomes during the first 48 hrs of infection (FIG. 2C). This data was consistent with a separate experiment in which EnAd and Ad11 p replication was compared by qPCR over a time course of infection, which demonstrated that EnAd produces a higher level of total genomes per cell than parental Ad11 p and a higher number of infectious virus particles (FIGS. 2D and 2E).

These data indicated that the E2B region likely determines the kinetics of virus replication in a cell, as regardless of other genomic changes in the viruses tested, those containing the Ad11p E2B produced lower total genomes in 48 hrs than viruses containing the EnAd E2B. Importantly, these data showed that a defect in the amount of genome replication was not responsible for the lack of NG-184 virus particles detected by CsCl banding.

Virus Amplification:

To investigate if fewer intact virus particles are being produced by NG-184 compared to EnAd during infection we monitored the production of a cytopathic effect in a cell monolayer infected with a high MOI of 330 particles per cell for EnAd or NG-184 or also a 5 fold higher MOI of 1650 ppc for NG-184. These data revealed that the cytopathic effect of the NG-184 virus was diminished compared to EnAd and that an input of ~5 fold higher amounts of NG-184 virus was required to produce a similar cytopathic effect to EnAd (FIG. 3) despite the replication data being equivalent (FIG. 2C). Taking the replication, amplification and purification data together and given that the only genomic difference between EnAd and NG-184 is the E4orf 4 deletion these data indicate that the presence of an intact E4orf4 (from Ad11p) limits the ability of an infected cell to convert replicated virus genomes into intact infectious virus particles, and/or the truncated protein product of the E4orf4 from EnAd containing the 25 bp deletion has an increased ability to drive intact particle production from the increased genome production driven by EnAd's E2B region.

Importantly this implies that there may be an essential balance maintained in EnAd's genome between the E2B and E4 regions, which contributes to its enhanced virus production kinetics and oncolytic activity in cells. An optimised oncolytic virus would therefore preferably contain both a chimeric E2B and deletion/partial deletion/truncation of E4 orf4

These results therefore demonstrate that E4orf4 deletion plays an important role in supporting virus particle production, in particular when the virus comprises a chimeric E2B region, which increases the rate of virus replication relative to the parent virus.

We claim:

1. A group B adenovirus comprising a sequence of formula (I):

5'ITR-$B_1$-$B_A$-$B_2$-$B_X$-$B_B$-$B_Y$-$B_3$-3'ITR wherein:
$B_1$ is bond or comprises: E1A, E1B or E1A-E1B;
$B_A$ is E2B-L1-L2-L3-E2A-L4;
$B_2$ is a DNA sequence from an E3 region encoding protein selected from the group consisting of a 12.1K, 16.1K, 18.5K, 20.3K, 20.6K, 10.3K, 15.2K, 15.3K and combinations thereof including all said E3 proteins;
$B_X$ is a bond or a DNA sequence consisting of at least one of: a restriction site or one or more transgenes, wherein each transgene is under control of an exogenous promoter;
$B_B$ is L5;
$B_Y$ is a bond or a DNA sequence comprising: a restriction site, one or more transgenes, or both;
$B_3$ is an E4 region wherein the E4orf4 is deleted, partially deleted, truncated or non-functional; and wherein a transgene is located in $B_X$, or in both $B_X$ and $B_Y$, wherein the transgene does not comprise a non-biased insertion transposon, and wherein $B_2$ is the only E3 sequence in the adenovirus.

2. An adenovirus according to claim 1, wherein the E2B element of $B_A$ is chimeric.

3. An adenovirus according to claim 1, wherein $B_X$ is a transgene.

4. An adenovirus according to claim 1, wherein $B_Y$ is a transgene and wherein $B_X$ is one or more transgenes, wherein each transgene in $B_X$ is under control of an exogenous promoter.

5. An adenovirus according to claim 1, wherein the one or more transgenes in $B_Y$ is under the control of an endogenous promoter.

6. An adenovirus according to claim 1, wherein the transgene further comprises a splice acceptor sequence.

7. An adenovirus according to claim 1, wherein the transgene further comprises an internal ribosome entry sequence.

8. An adenovirus according to claim 1, wherein the transgene further comprises a Kozak sequence.

9. An adenovirus according to claim 1, wherein the transgene encodes a 2A peptide.

10. An adenovirus according to claim 1, wherein the transgene further comprises a polyadenylation sequence.

11. An adenovirus according to claim 1, wherein at least one transgene encodes monocistronic mRNA.

12. An adenovirus according to claim 1, wherein at least one transgene encodes a polycistronic mRNA.

13. An adenovirus according to claim 1, wherein the transgene encodes an RNAi sequence, a peptide or a protein.

14. An adenovirus according to claim 13, wherein:
  a. the RNAi, peptide or protein targets one or more of the following: stimulatory T-cell co-receptors or ligands thereto, checkpoint inhibitory T-cell co-receptor molecules or ligands thereto, cytokines or cytokine receptors, chemokines or chemokine receptors,
  b. the stimulatory T-cell receptor or ligand thereto is selected from OX40, OX40 ligand, CD27, CD28, CD30, CD40, CD80, CD86, CD40 ligand, CD70, CD137, GITR, 4-1BB, ICOS and ICOS ligand,
  c. the checkpoint inhibitory T-cell co-receptor molecule or ligand thereto is selected from CTLA-4, PD-1, PD-L1, PD-L2, VISTA, B7-H3, B7-H4, HVEM, ILT-2, ILT-3, ILT-4, TIM-3, LAG-3, BTLA, LIGHT and CD160,
  d. the chemokine or chemokine receptor is selected from IL-8, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and CRTH2, and/or
  e. the cytokine or cytokine receptor is selected from IL-1α, IL-1β, IL-6, IL-9, IL-12, IL-13, IL-17, IL-18, IL-22, IL-23, IL-24, IL-25, IL-26, IL-27, IL-33, IL-35, Interleukin-2 (IL-2), IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF.

15. An adenovirus according to claim 1, wherein the transgene is a reporter gene selected from the group comprising sodium iodide symporter, intracellular metalloproteins, HSV1-tk, GFPs, luciferase or oestrogen receptor.

16. An adenovirus according to claim 1, wherein the transgene encodes an antibody or binding fragment thereof.

17. An adenovirus according to claim 1, wherein the adenovirus is:
  a. serotype 11,
  b. is chimeric, and/or
  c. oncolytic.

18. An adenovirus according to claim 1, wherein the adenovirus is replication competent.

19. A pharmaceutical formulation comprising a virus as defined in claim 1, and a pharmaceutically acceptable excipient, diluent and/or carrier.

20. An adenovirus according to claim 1, wherein the E2B element of $B_A$ is an Ad3/Ad11 chimeric sequence.

21. An adenovirus according to claim 20, wherein the Ad3/Ad11 chimeric sequence is given in SEQ ID NO: 8.

22. An adenovirus according to claim 5, wherein the endogenous promoter is a major late promoter.

23. An adenovirus according to claim 6, wherein the splice acceptor sequence is selected from the group comprising SSA, SA or BSA.

24. An adenovirus according to claim 8, wherein the Kozak sequence is at the start of the protein coding sequence.

25. An adenovirus according to claim 5, wherein the transgene further comprises a splice acceptor sequence.

26. An adenovirus according to claim 25, wherein the splice acceptor sequence is selected from the group comprising SSA, SA or BSA.

* * * * *